US010738334B2

(12) United States Patent
Hiller et al.

(10) Patent No.: US 10,738,334 B2
(45) Date of Patent: Aug. 11, 2020

(54) CELLS HAVING REDUCED BCAT1

(71) Applicant: PFIZER INC., New York, NY (US)

(72) Inventors: Gregory Walter Hiller, Wakefield, MA (US); Jeffrey Joseph Mitchell, Nashua, NH (US); Bhanu Chandra Mulukutla, Lawrence, MA (US); Pamela Mary Pegman, Weston, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/762,345

(22) PCT Filed: Sep. 22, 2016

(86) PCT No.: PCT/IB2016/055666
§ 371 (c)(1),
(2) Date: Mar. 22, 2018

(87) PCT Pub. No.: WO2017/051347
PCT Pub. Date: Mar. 30, 2017

(65) Prior Publication Data
US 2018/0265904 A1 Sep. 20, 2018

Related U.S. Application Data

(60) Provisional application No. 62/396,475, filed on Sep. 19, 2016, provisional application No. 62/222,555, filed on Sep. 23, 2015.

(51) Int. Cl.
| | |
|---|---|
| *C12N 15/11* | (2006.01) |
| *C12P 7/62* | (2006.01) |
| *C12P 7/42* | (2006.01) |
| *C12P 7/52* | (2006.01) |
| *C07K 16/00* | (2006.01) |
| *C12P 7/56* | (2006.01) |
| *C12P 7/40* | (2006.01) |
| *C12P 17/18* | (2006.01) |

(52) U.S. Cl.
CPC .............. *C12P 7/62* (2013.01); *C07K 16/00* (2013.01); *C12P 7/40* (2013.01); *C12P 7/42* (2013.01); *C12P 7/52* (2013.01); *C12P 7/56* (2013.01); *C12P 17/182* (2013.01); *C12N 2500/32* (2013.01); *C12N 2500/34* (2013.01); *C12N 2510/00* (2013.01); *C12N 2510/02* (2013.01); *C12N 2511/00* (2013.01)

(58) Field of Classification Search
CPC ............... C12N 15/1187; C12N 15/11; C12Y 206/01042
See application file for complete search history.

(56) References Cited

U.S. PATENT DOCUMENTS 7,294,484 B2  11/2007  Drapeau et al.
2013/0310545 A1*  11/2013  Radlwimmer ......... A61K 31/00
530/389.8

FOREIGN PATENT DOCUMENTS

WO  2004048556     6/2004
WO  2004104186    12/2004
WO  2009/086215 A2  7/2009

OTHER PUBLICATIONS

Ananieva et al. May 20, 2014; Cytosolic branched chain aminotransferase (BCATc) regulates mTORC1 signaling and glycolytic metabolism in CD4+ T cells. J. Biol. Chem. 289(27): 18793-18804.*
Altamirano C, Illanes A, Becerra S, Cairo JJ, Godia F (2006) Considerations on the lactate consumption by CHO cells in the presence of galactose. Journal of biotechnology 125: 547-556.
Bertoni JM (1981) Competitive inhibition of rat brain hexokinase by 2-10 deoxyglucose, glucosamine, and metrizamide. Journal of neurochemistry 37: 1523-1528.
Butler et al, Cytotechnology 15: 87-94, 1994.
Clem B, Telang S, Clem A, Yalcin A, Meier J, Simmons A, Rasku MA, Arumugam S, Dean WL, Eaton J, Lane A, Trent JO, Chesney J (2008) Small-molecule inhibition of 6-phosphofructo-2-kinase activity suppresses glycolytic flux and tumor growth. Molecular cancer therapeutics 7: 110-120.
Duvel K, Yecies JL, Menon S, Raman P, Lipovsky AI, Souza AL, Triantafellow E, Qichen M, Gorski R, Cleaver S, Vander Heiden MG, MacKeigan JP, Finan PM, Clish CB, Murphy LO, Manning BO (2010) Activation of a metabolic gene regulatory network downstream of mTOR complex 1. Molecular cell 39: 171-183.
Gagnon M, Hiller G, Luan YT, Kittredge A, DeFelice J, Drapeau D (2011) High-end pH-controlled delivery of glucose effectively suppresses lactate accumulation in CHO fed-batch cultures. Biotechnology and bioengineering 108: 1328-1337.
Hong et Al, Appl Microbial Biotechnol (2010) 88:869-876.
Kim SH, Lee GM (2007a) Down-regulation of lactate dehydrogenase-A by siRNAs for reduced lactic acid formation of Chinese hamster ovary cells producing thrombopoietin. Applied microbiology and biotechnology 74: 152-159.
Kim SH, Lee GM (2007b) Functional expression of human pyruvate carboxylase for reduced lactic acid formation of Chinese hamster ovary cells (DG44). Applied microbiology and biotechnology 76: 659-665.
Lee HL T, Boccazzi P, Gorret N, Ram RJ, Sinskey AJ (2004) In situ bioprocess monitoring of *Escherichia coli* bioreactions using Raman spectroscopy. Vibrational Spectroscopy 35: 131-137.
Lee JS, Lee GM (2012) Rapamycin treatment inhibits CHO cell death in a serumfree suspension culture by autophagy induction. Biotechnology and bioengineering 109: 3093-3102.
Li B, Ryan PW, Ray BH, Leister KJ, Sirimuthu NM, Ryder AG (2010) Rapid characterization and quality control of complex cell culture media solutions using raman spectroscopy and chemometrics. Biotechnology and bioengineering 107: 290-301.

(Continued)

*Primary Examiner* — Karen Cochrane Carlson
(74) *Attorney, Agent, or Firm* — Stephen E. Moyer

(57) ABSTRACT

The invention relates to a method of cell culture where the cells are modified to reduce the level of synthesis of growth and/or productivity inhibitors by the cell. The invention also relates to a method of cell culture for improving cell growth and productivity, in particular in fed-batch culture of mammalian cells at high cell density. The invention further relates to a method of producing cells with improved cell growth and/or productivity in cell culture and to cells obtained or obtainable by such methods.

12 Claims, 41 Drawing Sheets
Specification includes a Sequence Listing.

(56) References Cited

OTHER PUBLICATIONS

Morgan HP, O'Reilly FJ, Wear MA, O'Neill JR, Fothergill-Gilmore LA, Hupp T, Walkinshaw MD (2013) M2 pyruvate kinase provides a mechanism for nutrient sensing and regulation of cell proliferation. Proceedings of the National Academy of Sciences of the United States of America 110: 5881-5886.

Mulukutla BC, Gramer M, Hu WS (2012) On metabolic shift to lactate consumption in fed-batch culture of mammalian cells. Metabolic engineering 14: 138-149.

Pamiak, M.A., Davis, M.D., and Kaufman, S. (1988) Effect of alkaline pH on the activity of rat liver phenylalanine hydroxylase. The Journal of biological chemistry 263, 1223-1230. Press, 1999.

Whelan J, Craven S, Glennon B (2012) In situ Raman spectroscopy for simultaneous monitoring of multiple process parameters in mammalian cell culture bioreactors. Biotechnology progress 28: 1355-1362.

Whitehouse S, Cooper RH, Randle PJ (1974) Mechanism of activation of pyruvate 15 dehydrogenase by dichloroacetate and other halogenated carboxylic acids. The Biochemical journal 141: 761-774.

Wlaschin KF, Hu WS (2007) Engineering cell metabolism for high-density cell culture via manipulation of sugar transport. Journal of biotechnology 131: 168-176.

Yi W, Clark PM, Mason DE, Keenan MC, Hill C, Goddard WA, 3rd, Peters EC, Driggers EM, Hsieh-Wilson LC (2012) Phosphofructokinase 1 glycosylation regulates cell growth and metabolism. Science 337: 975-980.

Zhou M, Crawford Y, Ng D, Tung J, Pynn AF, Meier A, Yuk IH, Vijayasankaran N, Leach K, Joly J, Snedecor B, Shen A (2011) Decreasing lactate level and increasing antibody production in Chinese Hamster Ovary cells (CHO) by reducing the expression of lactate dehydrogenase and pyruvate dehydrogenase kinases. Journal of biotechnology 153: 27-34.

Zhu G, Zhu X, Fan Q, Wan X (2011) Raman spectra of amino acids and their aqueous solutions. Spectrochimica acta Part A, Molecular and biomolecular spectroscopy 78: 1187-1195.

Wilson et al. J. Biol. Chem. 267:963-967, 1992.

Cary O. Harding et al: "Expression of phenylalanine hydroxylase (PAH) in erythrogenic bone marrow does not correct hyperphenylalaninemia inPahenu2 mice", Journal of Gene Medicine, vol. 5, No. 11, Jan. 1, 2003 (Jan. 1, 2003), pp. 984-993.

A Martinez et al: "Expression of recombinant human phenylalanine hydroxylase as fusion protein in Escherichia coli circumvents proteolytic degradation by host cell proteases. Isolation and characterization of the wild-type enzyme", Biochemical Journal, vol. 306, No. 2, Mar. 1, 1995 (Mar. 1, 1995), pp. 589-597.

Martje Tonjes et al: "BCAT1 promotes cell proliferation through amino acid catabolism in gliomas carrying wild-type IDH1", Nature Medicine, vol. 19, No. 7, Jun. 23, 2013 (Jun. 23, 2013), pp. 901-908.

Zhi-Qiang Wang et al: "BCAT1 expression associates with ovarian cancer progression: possible implications in altered disease metabolism", Oncotarget, Sep. 10, 2015 (Sep. 10, 2015), p. 31522.

Wen Zhou et al: "Over-expression of BCAT1, a c-Myc target gene, induces cell proliferation, migration and invasion in nasopharyngeal carcinoma", Molecular Cancer, Biomed Central, London, GB, vol. 12, No. 1, Jun. 8, 2013 (Jun. 8, 2013), p. 53.

Marte I. Flydal et al: "Phenylalanine hydroxylase: Function, structure, and regulation", IUBMB Life, vol. 65, No. 4, Mar. 4, 2013 (Mar. 4, 2013), pp. 341-349.

Matthew Gagnon et al: "High-End 1-8, pH-controlled delivery of glucose 11-48, effectively suppresses lactate 51-60, accumulation in CHO Fed-batch cultures", Biotechnology and Bioengineering, vol. 108, No. 6, Jun. 24, 2011 (Jun. 24, 2011), pp. 1328-1337.

Zhou, M, et al., "Decreasing lactate level and increasing antibody production in Chinese Hamster Ovary cells (CHO) by reducing the expression of lactate dehydrogenase and pyruvate dehydrogenase kinases", Journal of Biotechnology, vol. 153, No. 1-2, Apr. 20, 2011, pp. 27-34.

\* cited by examiner

| Gene | Ct Value | Δ Ct |
|---|---|---|
| B-Actin (CHO) | 15.9 | |
| Slc2a1 | 21.8 | 5.9 |
| Mif | 16.9 | 1.0 |
| Got2 | 17.7 | 1.8 |
| Dld | 19.2 | 3.8 |
| Got1 | 21.0 | 5.1 |
| Fah | 24.3 | 8.4 |
| Gstz1 | 24.6 | 8.7 |
| Pah | 27.7 | 11.8 |
| Hgd | 35.3 | 19.4 |
| Hpd | 37.0 | 21.1 |

*Overexpression of Pah, Hpd & Hgd can potentially divert the flux away from the inhibitor production*

(C)

(D)

Figure 33A, 33B
(A)
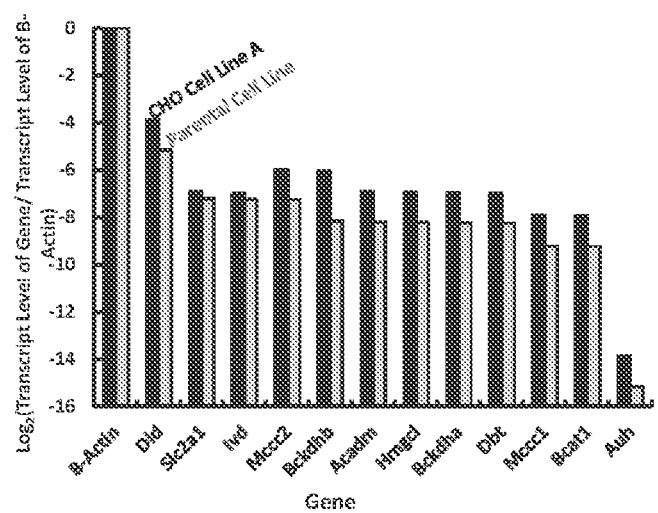
(B)
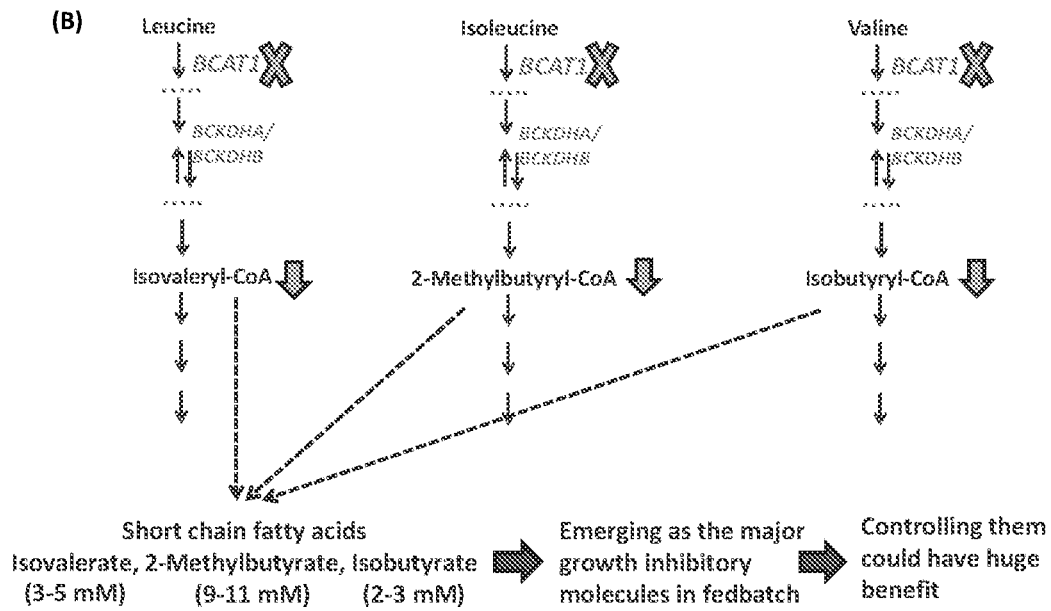
 indicates knockdown or knockout           indicates reduced production B-Actin in CHO Parental Cell Line
Predicted 42kDa B-Actin in CHO Cell Line B
Predicted 42kDa

B-Actin Expression in Stable Knockdown Pools Generated from CHO Parental Cell Line
Predicted 42kDa

BCAT1 Expression in Stable Knockdown Pools Generated from CHO Parental Cell Line
Predicted 43kDa

CELLS HAVING REDUCED BCAT1

This application is a § 371 filing of PCT/IB2016/055666 filed Sep. 22, 2016, which claims the benefit of priority to United States Provisional Application Nos. 62/222,555 filed Sep. 23, 2015 and 62/396,475 filed Sep. 19, 2016; the entire contents of which are incorporated herein by reference.

REFERENCE TO SEQUENCE LISTING

This application was filed electronically via EFS-Web and includes an electronically submitted sequence listing in .txt format. The .txt file contains a sequence listing entitled "PC72254A_SeqListing_ST25.txt" created on Jun. 10, 2020 and having a size of 2 KB. The sequence listing contained in this .txt file is part of the specification and is herein incorporated by reference in its entirety.

FIELD OF THE INVENTION

The invention relates to a method of cell culture where the cells are modified to reduce the level of synthesis of growth and/or productivity inhibitors by the cell. The invention also relates to a method of cell culture for improving cell growth and productivity, in particular in fed-batch culture of mammalian cells at high cell density. The invention further relates to a method of producing cells with improved cell growth and/or productivity in cell culture and to cells obtained or obtainable by such methods.

BACKGROUND OF THE INVENTION

Proteins have become increasingly important as diagnostic and therapeutic agents. In most cases, proteins for commercial applications are produced in cell culture, from cells that have been engineered and/or selected to produce unusually high levels of a particular protein of interest. Optimization of cell culture conditions is important for successful commercial production of proteins. Mammalian cells have inefficient metabolism which causes them to consume large amounts of nutrients and convert a significant amount of them to byproducts. The byproducts are released into the culture and accumulate over the course of the culture. Lactate and ammonia, known to be the conventional inhibitors of cells in culture, are the two major byproducts of cellular metabolism that accumulate to high levels in culture and beyond certain concentrations, they start inhibiting the growth and productivity of cells in culture. Cell culture methods aimed at reducing the amount of lactate and ammonia in the cell culture medium have been developed and can increase the growth and the productivity of mammalian cells. The cell growth, however, still slows down even when concentrations of lactate and ammonia are kept low, thereby limiting the maximum cell density and productivity of the cells.

Therefore, there is a need for the development of improved cell culture systems for optimum production of proteins. In particular there is a need for cell culture methods providing an increased viable cell density and/or titer and in particular for cells which are modified to reduce the level of synthesis of growth and/or productivity inhibitors.

SUMMARY OF THE INVENTION

The invention relates to a method of cell culture comprising (i) providing cells in a cell culture medium to start a cell culture process, wherein the cells are modified to reduce the level of synthesis of growth and/or productivity inhibitors by the cell.

The invention also relates to method of producing cells with improved cell growth and/or productivity in cell culture comprising the steps of:
(i) identification of a cell metabolite or metabolites which are cell growth and/or productivity inhibitors,
(ii) identification of the cell metabolic pathway or pathways resulting in the synthesis of the cell growth and/or productivity inhibitors,
(iii) identification of one or more genes in the cell metabolic pathway or pathways encoding an enzyme which catalyses the synthesis of the cell growth and/or productivity inhibitors or metabolic intermediates thereof, and/or one or more genes encoding an enzyme in a metabolic pathway branching or directly branching therefrom,
(iv) modifying the expression of the one or more genes to reduce the level of synthesis of the cell growth and/or productivity inhibitors.

The invention further relates to a cell comprising one or more modified genes which reduces the level of synthesis of growth and/or productivity inhibitors by the cell, in particular wherein the one or more modified genes is selected from Bcat1, Bcat2, Auh, Mccc1, Mccc2, Ivd, PCDB1, QDPR, Hpd, Hgd and Pah, wherein the modification increases or decreases the gene expression, and the use of the foregoing cells for the expression of a recombinant protein or polypeptide.

BRIEF DESCRIPTION OF DRAWINGS

FIG. 33: Gene expression analysis of leucine pathway genes using RT-qPCR assay. (A) Expression levels of leucine pathway genes in CHO cell line A and CHO parental cell line. Data is plotted as log of the ration of gene of interest transcript level to B-Actin transcript level. Higher value indicates higher expression of gene. (B) Schematic of leucine, isoleucine and valine catabolic pathways. Isovalerate, 2-methylbutyrate and isobutyrate are growth inhibitory byproducts of leucine, isoleucine and valine catabolic pathways, respectively. BCAT1 (BCAT2) and BCKHDA/BCKHDB are shared by all the three catabolic pathways. Knockdown or knockout or inhibition, for example inhibition with a small molecule inhibitor molecule, of enzyme activity of BCAT1 (and/or BCAT2), or BCKDHA/BCKDHB will concurrently reduce the biosynthesis of the three inhibitory metabolites (isovalerate, 2-methylbutyrate and isobutyrate).

DETAILED DESCRIPTION

Figures 1A, 1B:
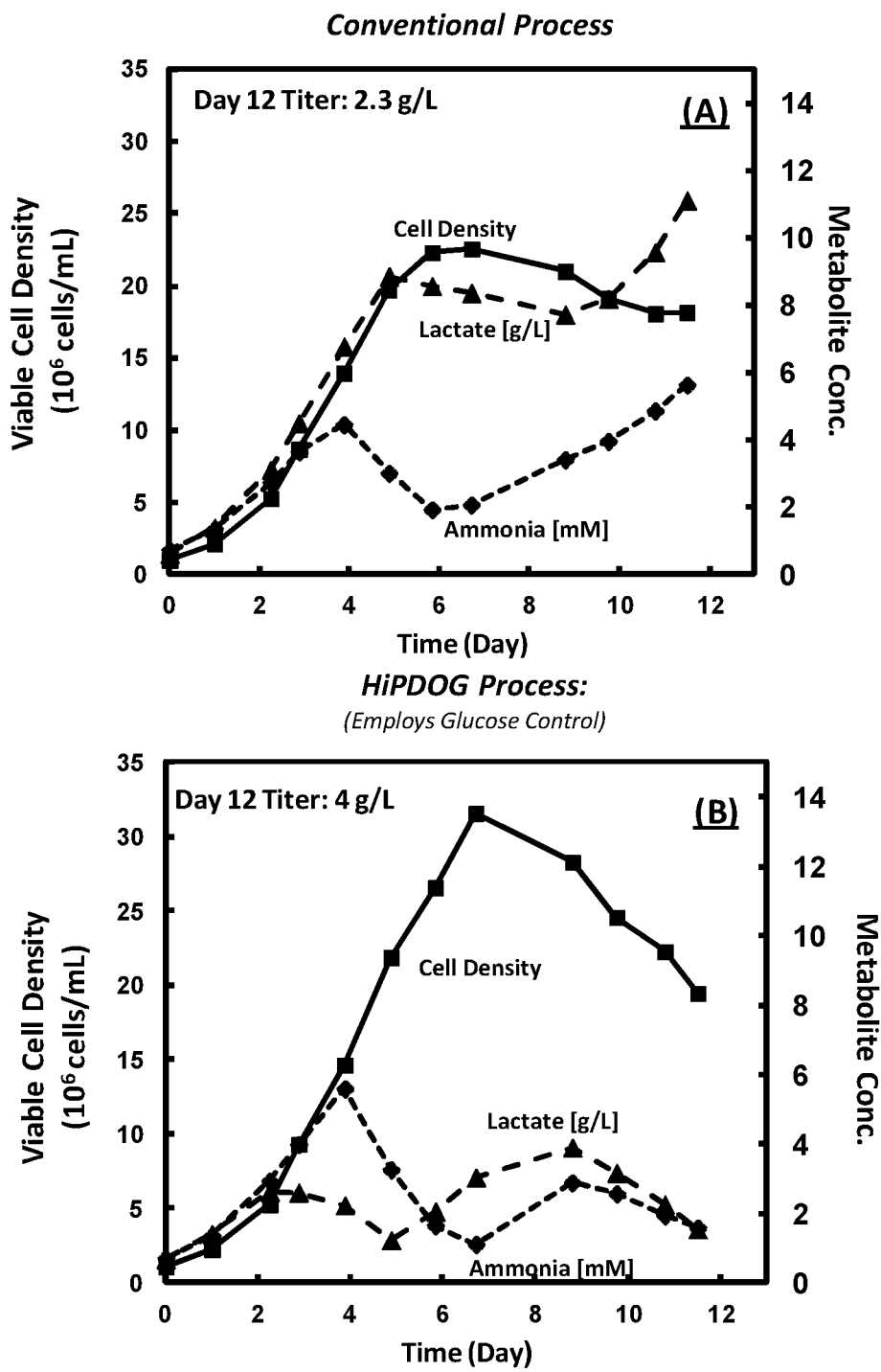
FIG. 1A shows the growth characteristics and metabolic profiles of CHO cells in conventional fed-batch process. Reported data includes viable cell densities (closed squares), culture lactate levels (closed triangles) and ammonia levels (closed diamonds). Also, reported is the harvest titer (day 12 protein concentration).
FIG. 1B shows the growth characteristics and metabolic profiles of CHO cells in a HiPDOG process. Reported data includes viable cell densities (closed squares), culture lactate levels (closed triangles) and ammonia levels (closed diamonds). Also, reported is the harvest titer (day 12 protein concentration).
Figures 2A, 2B, 2C:
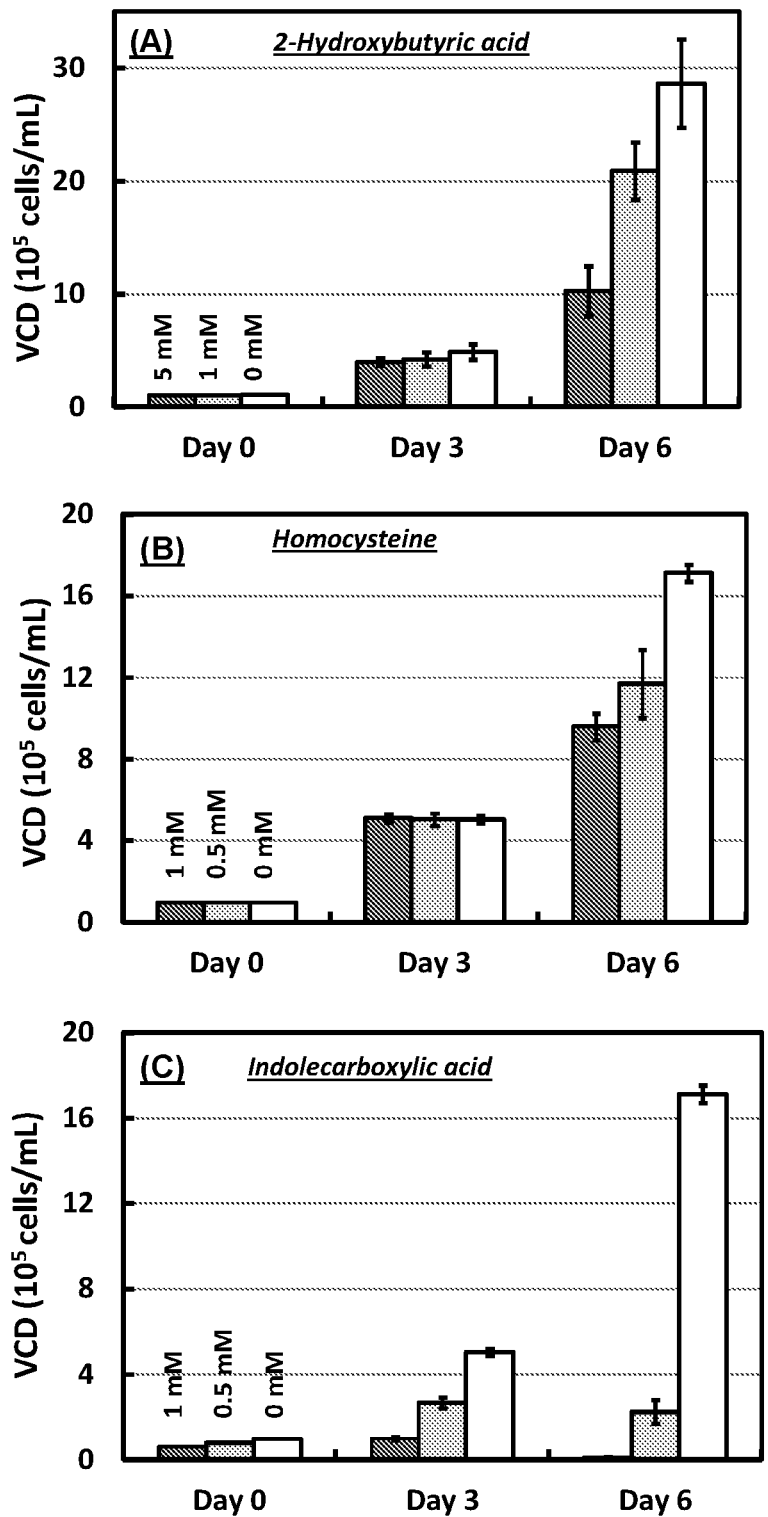
FIG. 2 shows graphs indicating the viable cell density of GS-CHO cells (hereafter GS-CHO, Cell line A) at day 0, Day 3 and Day 6 when exposed to increasing concentrations of 2-hydroxybutyric acid (FIG. 2A), homocysteine (FIG. 2B) or indolecarboxylic acid (FIG. 2C). GS-CHO cells were inoculated in Medium A at low viable cell densities and were treated with reported concentrations of the inhibitors, individually. The effect of the inhibitors on growth of the cells was monitored for 6 days.
Figure 3A:
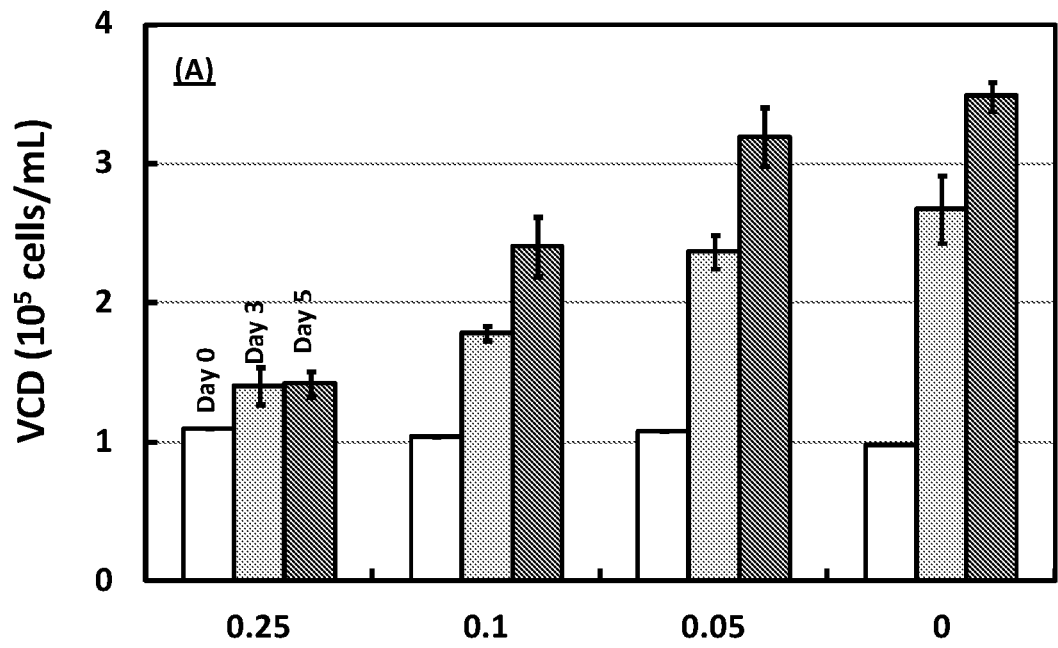
FIG. 3 shows the effect of increasing concentrations of two metabolites, 4-hydroxyphenylpyruvate (FIG. 3A) and phenyllactate (FIG. 3B) on viable cell density of the GS-CHO cells. GS-CHO cells were inoculated in Medium A at low viable cell densities and were treated with reported concentrations of the inhibitors, individually.
Figure 3B:
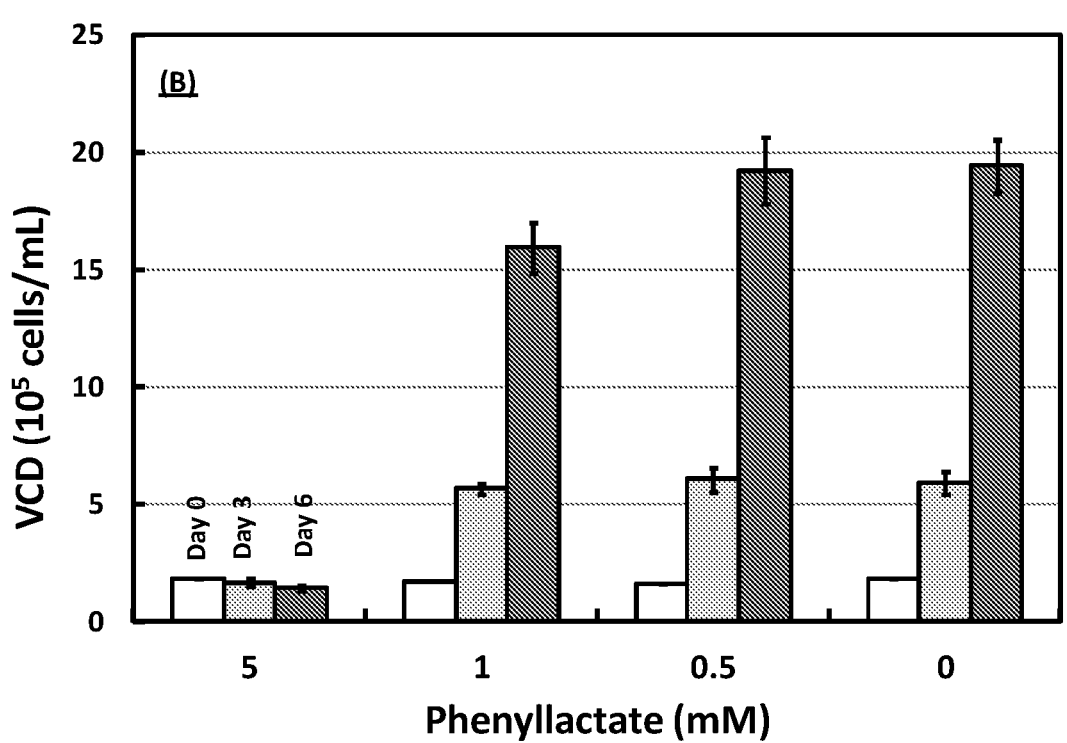
Figures 4A, 4B:
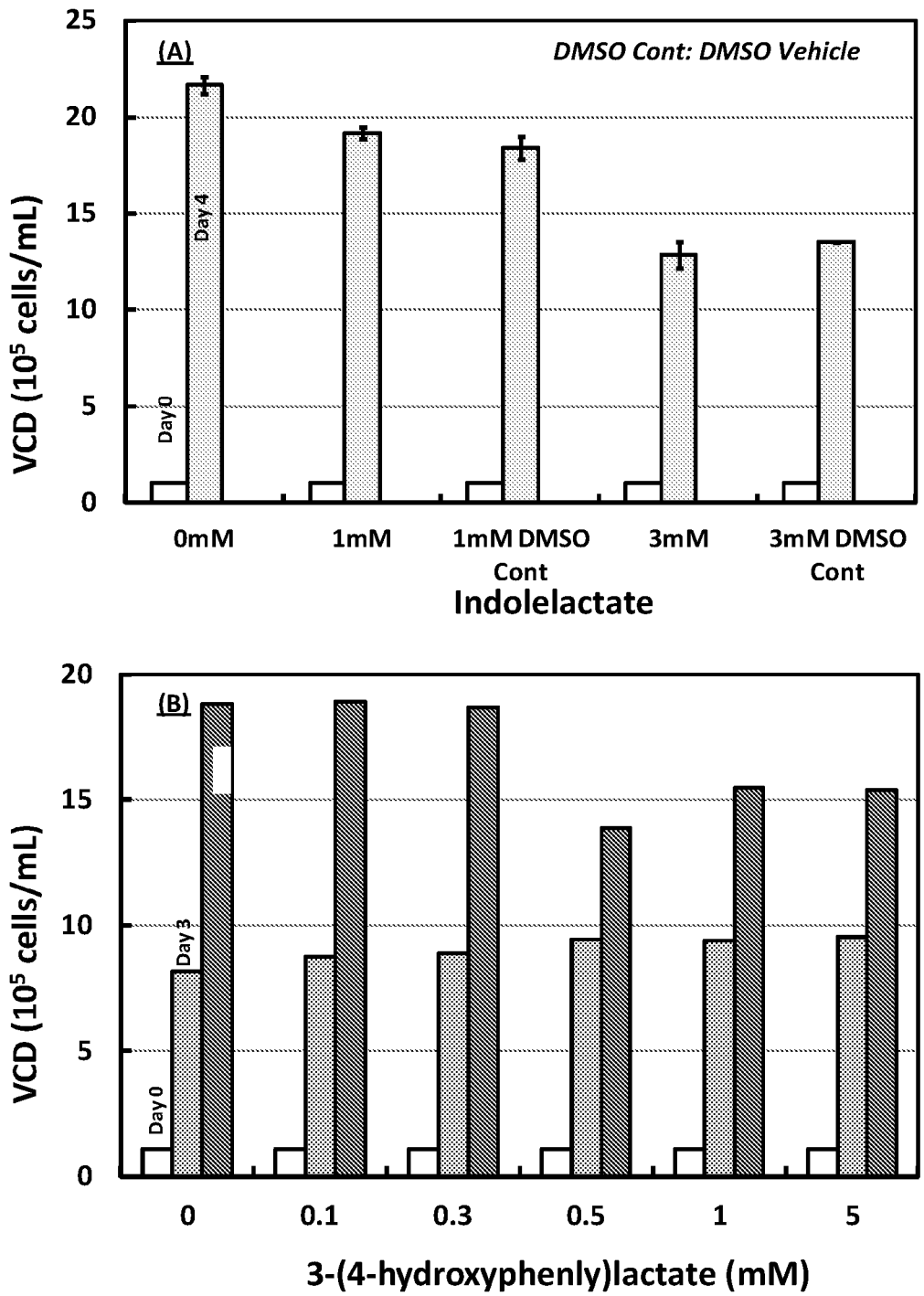
FIGS. 4 and 5 show the effect of increasing concentrations of four metabolites, indolelactate (FIG. 4A), 3-(4-hydroxyphenyl)lactate (FIG. 4B), sodium formate (FIG. 5A) and isovalerate (FIG. 5B), on viable cell density of the GS-CHO cell. GS-CHO cells were inoculated in Medium A at low viable cell densities and were treated with reported concentrations of the inhibitors, individually.
Figures 5A, 5B:
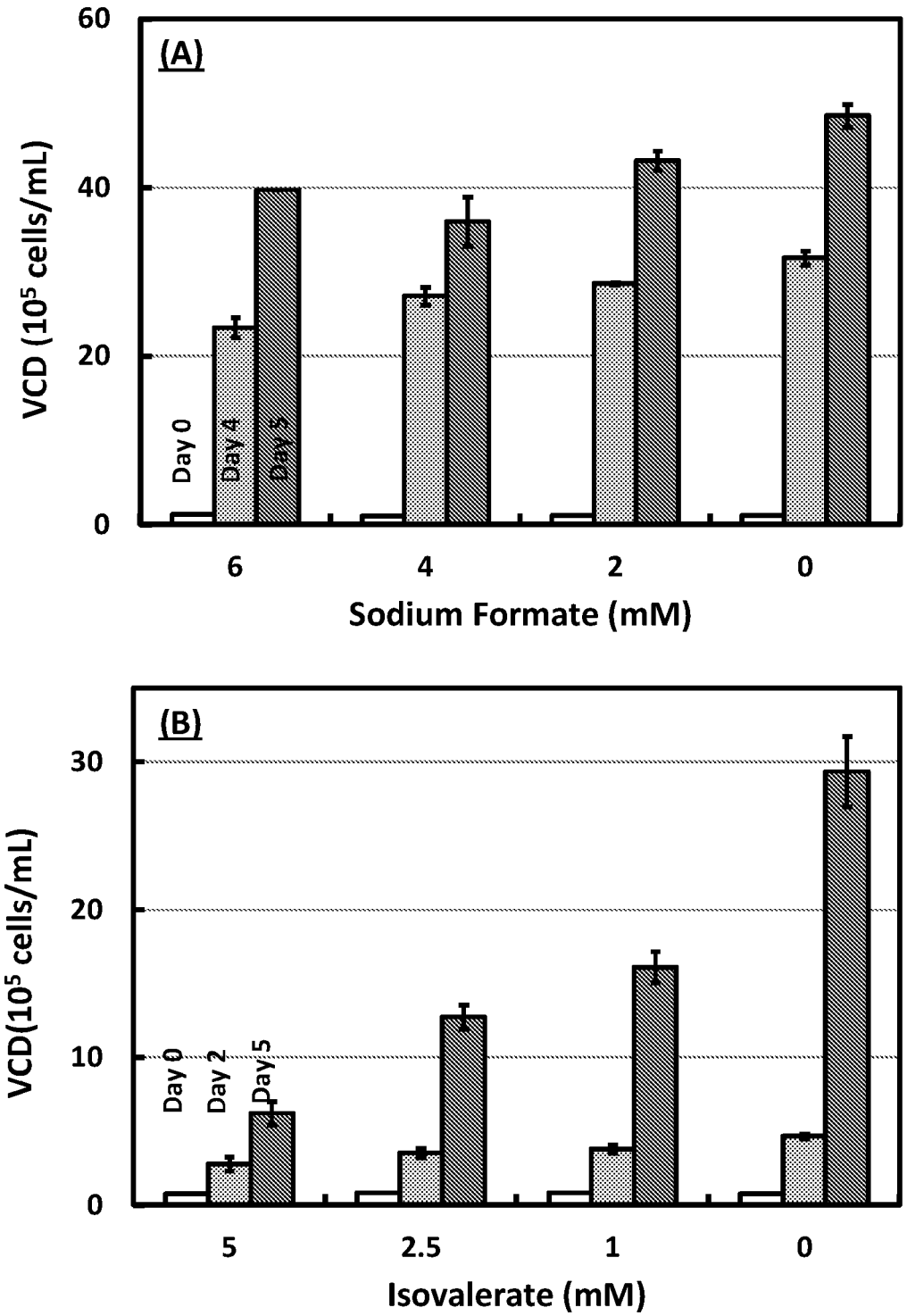

The present invention provides methods and media for cell culture. The present invention provides cell culture methods where the concentration of at least one metabolite selected from 3-(4-hydroxyphenyl)lactate, 4-hydroxyphenylpyruvate, phenyllactate, phenylpyruvate, indolelactate (indole-3-lactate), indolecarboxylic acid (indole-3-carboxylate), homocysteine, 2-hydroxybutyric acid, isovalerate, 2-methyl butyrate, isobutyrate and formate, and/or at least one amino acid selected from phenylalanine, tyrosine, tryptophan, methionine, leucine, serine, threonine and glycine is maintained at low levels in the cell culture medium.

The inventors have unexpectedly discovered that, in cell culture, and in particular in high density cell culture, such as for example fed-batch cell culture aiming at producing high amount of a recombinant protein of interest, the growth of cells was inhibited by the accumulation of metabolites such as 3-(4-hydroxyphenyl)lactate, 4-hydroxyphenylpyruvate, phenyllactate, phenylpyruvate, indolelactate, indolecarboxylic acid, homocysteine, 2-hydroxybutyric acid, isovalerate, 2-methyl butyrate, isobutyrate and formate in the cell culture medium. The inhibitory effect of these metabolites can be limited by maintaining their concentration in the cell culture medium below levels where they inhibit cell growth. The inhibitory effects of these metabolites have also be can be limited by modifying one or more genes in the cell to reduce the level of synthesis of growth and/or productivity inhibitors by the cell, in particular where the one or more modified genes is selected from Bcat1, Bcat2, Auh, Mccc1, Mccc2, Ivd, Hpd, Hgd, Pah, PCBD1, and QDPR.

Methods Comprising Controlling the Metabolite Concentration in the Cell Culture Medium at Low Levels In a first aspect the invention provides a method of cell culture comprising (i) providing cells in a cell culture medium to start a cell culture process, wherein the cells are modified to reduce the level of synthesis of growth and/or productivity inhibitors by the cell.

In some embodiments, the cells are modified to modify expression of one or more genes, in one embodiment the genes are in the cell metabolic pathway or pathways which synthesise the growth inhibitors or metabolic intermediates thereof, or metabolites of growth inhibitors or metabolic intermediates thereof, or metabolite of the metabolic intermediate.

"Metabolic intermediates" are understood to comprise molecules which are the precursors or metabolites required for the synthesis of a cell growth and/or productivity inhibitor and include reactant, product and cofactor molecules of enzymes of the cell metabolic pathway or pathways. Relevant cofactors include for example BH4 (tetrahydrobiopterin), or BH4-4a (carbinolamine), or q-BH2. Metabolic intermediates may be synthesised in the same pathway(s) as the cell metabolic pathway or pathways encoding an enzyme which catalyses the synthesis of the cell growth and/or productivity inhibitor or may be synthesised in a branching pathway. "Metabolites" are understood to comprise the products of metabolic reactions catalysed by the enzymes of the cell metabolic pathway or pathways and include reactant, product and cofactor molecules of said enzymes such as for example BH4 (tetrahydrobiopterin), or BH4-4a (carbinolamine), or q-BH2. Metabolites may arise in the same pathway(s) as the cell metabolic pathway or pathways encoding an enzyme which catalyses the synthesis of the cell growth and/or productivity inhibitor or intermediate thereof or may be synthesised in a branching pathway. The branching pathway may arise at a node situated above or below the one or more one or more genes in the cell metabolic pathway or pathways encoding an enzyme which catalyses the synthesis of the cell growth and/or productivity inhibitor or intermediate thereof.

In some embodiments, the one or more genes modified encodes an enzyme that catalyses the synthesis of 3-(4-hydroxyphenyl)lactate (HPLA), 4-hydroxyphenylpyruvate, phenyllactate (PLA), phenyl pyruvate, indole-3-carboxylate (indolecarboxylic acid), indole-3-lactate (indolelactate), 2-hydroxybutyric acid, homocysteine, isovalerate, 2-methyl butyrate, isobutyrate, butyrate, formate, or a metabolic intermediate thereof or metabolites of said molecules or metabolic intermediates thereof, or metabolite of the metabolic intermediate.

In some embodiments, the one or more genes modified encodes an enzyme that catalyses the synthesis of 4-hydroxyphenylpyruvate or phenyllactate (PLA), metabolite thereof or a metabolic intermediate thereof, or metabolite of the metabolic intermediate.

In some embodiments, the one or more genes modified encodes an enzyme that catalyses the synthesis of isovalerate, 2-methylbutyrate, isobutyrate or butyrate, metabolite thereof or a metabolic intermediate thereof, or metabolite of the metabolic intermediate.

In some embodiments, the one or more genes modified is selected from; PCDB1, QDPR, Pah, Mif, Got1, Got2, Nup62-il4i1, Hpd, Hgd, Gstz1, Fah.

In some embodiments, the one or more genes modified is selected from; PCDB1, QDPR Hpd, Hgd and Pah; in one embodiment wherein the one or more genes modified is selected from; (i) PCDB1, (ii) Pah, (iii) QDPR, (iv) PCBD1 and QDPR, (v) PCBD1 and Pah, (vi) Pah and QDPR, (vii) PCDB1 and Pah, and QDPR, (viii) any of (i) to (vii) and Hpd and/or Hgd.

In some embodiments, the one or more genes modified is selected from; Bcat1, Bcat2, Bckdha/b, Dbt/Dld, Ivd, Acadm, Mccc1, Mccc2, Auh, Hmgcl, Fasn.

In some embodiments, the one or more genes modified is selected from, Bcat1, Bcat2, Auh, Mccc1, Mccc2, Ivd.

In some embodiments, the one or more genes modified is;
(i) Auh,
(ii) Bcat1,
(iii) Bcat2
(iv) one or more of Mccc1, Mccc2 and Ivd,
(v) Bcat1 and/or Bcat2 and/or Auh and one or more Mccc1, Mccc2 and Ivd,
(vi) Pah,
(vii) PCBD1,
(viii) PCBD1 and/or QDPR
(ix) one or more of Hpd and Hgd,
(x) Pah and/or PCBD1 and one or more of Hpd and Hgd.
(xi) Pah and PCBD1, and optionally QDPR
(xii) Pah, PCBD1, Hpd and Hgd, and optionally QDPR
(xiii) Bcat1 and/or Bcat2, Auh, Mccc1, Mccc2 and Ivd or
(ix) Bcat1 and/or Bcat2, Auh, Mccc1, Mccc2, Ivd, Pah, PCBD1, Hpd, Hgd and optionally QDPR.

In some embodiments, the one or more genes are modified to increase or decrease gene expression.

In some embodiments, the one or more genes are modified to increase gene expression, in one embodiment wherein the one or more genes are Pah and/or PCDB1 and/or QDPR and/or Hpd and/or Hgd.

In some embodiments, the one or more genes are modified to decrease gene expression, in one embodiment wherein the one or more genes are Bcat1 and/or Bcat2.

In some embodiments, the one or more genes modified is selected from; (i) PCDB1, (ii) Pah, (iii) QDPR, (iv) PCBD1 and QDPR, (v) PCBD1 and Pah, (vi) Pah and QDPR, (vii) PCDB1 and Pah, and QDPR, (viii) any of (i) to (vii) and Hpd and/or Hgd.

In some embodiments, the cell comprises;
(i) an expressible nucleic acid or vector construct comprising a PCDB1 gene,
(ii) an expressible nucleic acid or vector construct comprising a Pah gene,
(iii) an expressible nucleic acid or vector construct comprising a Pah gene and PCDB1 gene,
(iv) an expressible nucleic acid or vector construct comprising a PCDB1 gene or Pah gene or Pah gene and PCDB1 gene, and additionally a QDPR gene,
(v) an expressible nucleic acid or vector construct of (i) to (iv) further comprising a Hpd gene and/or a Hgd gene.

In some embodiments the method further comprises;
(ii) maintaining at least one metabolite selected from 3-(4-hydroxyphenyl)lactate, 4-hydroxyphenylpyruvate, phenyllactate, indolelactate (indole-3-lactate), indolecarboxylic acid (indole-3-carboxylate), homocysteine, 2-hydroxybutyric acid, isovalerate, 2-methylbutyrate, isobutyrate and formate below a concentration C1 in the cell culture medium, wherein C1 is 3 mM.

In some embodiments, C1 is 2.5 mM, 2 mM, 1.5 mM, 1 mM, 0.9 mM, 0.8 mM, 0.7 mM, 0.6 mM, 0.5 mM, 0.4 mM, 0.3 mM, 0.2 mM or 0.1 mM. In some embodiments, C1 is 1 mM. In some embodiments, C1 is 0.5 mM.

In some embodiments, step (ii) comprises the step of measuring the concentration of said at least one metabolite.

In some embodiments, when the measured concentration is above a predefined value, the concentration of precursor of said at least one metabolite in the cell culture medium is decreased by reducing the amount of precursor provided to the cells. Said predefined value is selected so that the decrease of concentration of said precursor prevents the concentration of metabolite from rising above C1. The predefined value can be equal to C1 or can be a percentage of C1. In some embodiments the percentage is 50, 55, 60, 65, 70, 75, 80, 85, 90 or 95% of C1. In some embodiments the percentage is 80% of C1.

In some embodiments, when the measured concentration of 3-(4-hydroxyphenyl)lactate, 4-hydroxyphenylpyruvate and/or phenyllactate is above said predefined value, the concentration of phenylalanine is decreased in the cell culture medium.

In some embodiments, when the measured concentration of 3-(4-hydroxyphenyl)lactate and/or 4-hydroxyphenylpyruvate is above said predefined value, the concentration of tyrosine is decreased in the cell culture medium.

In some embodiments, when the measured concentration of 3-(4-hydroxyphenyl)lactate, 4-hydroxyphenylpyruvate and/or phenyllactate is above said predefined value, the concentrations of tyrosine and phenylalanine are decreased in the cell culture medium.

In some embodiments, when the measured concentration of indolelactate and/or indolecarboxylic acid is above said predefined value, the concentration of tryptophan is decreased in the cell culture medium.

In some embodiments, when the measured concentration of homocysteine and/or 2-hydroxybutyric acid is above said predefined value, the concentration of methionine is decreased in the cell culture medium.

In some embodiments, when the measured concentration of isovalerate is above said predefined value, the concentration of leucine is decreased in the cell culture medium.

In some embodiments, when the measured concentration of 2-methylbutyrate is above said predefined value, the concentration of isoleucine is decreased in the cell culture medium.

In some embodiments, when the measured concentration of isobutyrate is above said predefined value, the concentration of valine is decreased in the cell culture medium.

In some embodiments, when the measured concentration of formate is above said predefined value, the concentration of serine, threonine and/or glycine is decreased in the cell culture medium.

In some embodiments, when the measured concentration of formate is above said predefined value, the concentration of serine is decreased in the cell culture medium.

In some embodiments, when the measured concentration of formate is above said predefined value, the concentration of threonine is decreased in the cell culture medium.

In some embodiments, when the measured concentration of formate is above said predefined value, the concentration of glycine is decreased in the cell culture medium.

The concentration of precursor in the cell culture medium can be decreased by reducing the amount of precursor provided to the cells, for example by reducing the concentration of said precursor in the feed medium, reducing the feed rate, or reducing the number or volume of feeds. For example, the feed medium can be replaced by a feed medium comprising a lower concentration of precursor.

In some embodiments of the above described methods, step (ii) comprises maintaining 1, 2, 3, 4, 5, 6, 7, 8, 9, 10 or 11 of 3-(4-hydroxyphenyl)lactate, 4-hydroxyphenylpyruvate, phenyllactate, indolelactate (indole-3-lactate), indolecarboxylic acid (indole-3-carboxylate), homocysteine, 2-hydroxybutyric acid, isovalerate, 2-methylbutyrate, isobutyrate and formate below C1 in the cell culture medium.

In some embodiments of the above described methods, step (ii) comprises maintaining 1, 2, 3, 4, 5, 6, or 7 of 3-(4-hydroxyphenyl)lactate, 4-hydroxyphenylpyruvate, phenyllactate, indolelactate, indolecarboxylic acid, homocysteine and 2-hydroxybutyric acid below C1 in the cell culture medium.

In some embodiments of the above described methods, step (ii) comprises maintaining 3-(4-hydroxyphenyl)lactate, 4-hydroxyphenylpyruvate and phenyllactate below C1 in the cell culture medium.

In some embodiments of the above described methods, step (ii) comprises maintaining indolelactate (indole-3-lactate) and indolecarboxylic acid (indole-3-carboxylate) below C1 in the cell culture medium.

In some embodiments of the above described methods, step (ii) comprises maintaining homocysteine and 2-hydroxybutyric acid below C1 in the cell culture medium.

In some embodiments of the above described methods, step (ii) comprises maintaining isovalerate, 2-methylbutyrate, and isobutyrate below C1 in the cell culture medium.

In some embodiments of the above described methods, step (ii) comprises maintaining isobutyrate below C1 in the cell culture medium.

In some embodiments of the above described methods, step (ii) comprises maintaining 2-methylbutyrate below C1 in the cell culture medium.

In some embodiments of the above described methods, step (ii) comprises maintaining isovalerate below C1 in the cell culture medium.

In some embodiments of the above described methods, step (ii) comprises maintaining formate below C1 in the cell culture medium.

In some embodiments of the above described methods, step (ii) comprises maintaining isovalerate and 4-hydroxyphenylpyruvate below C1 in the cell culture medium.

In some embodiments of the above described methods, step (ii) comprises maintaining 3-(4-hydroxyphenyl)lactate, 4-hydroxyphenylpyruvate, phenyllactate, indolelactate (indole-3-lactate), indolecarboxylic acid (indole-3-carboxylate), homocysteine, 2-hydroxybutyric acid isovalerate, 2-methylbutyrate, isobutyrate and formate below C1 in the cell culture medium.

In some embodiments of the above described methods, in step (ii), the concentration of 3-(4-hydroxyphenyl)lactate is maintained below 0.5 mM, 0.4 mM, 0.3 mM, 0.2 mM, or 0.1 mM.

In some embodiments of the above described methods, in step (ii), the concentration of 3-(4-hydroxyphenyl)lactate is maintained below 0.3 mM.

In some embodiments of the above described methods, in step (ii), the concentration of 3-(4-hydroxyphenyl)lactate is maintained below 0.1 mM.

In some embodiments of the above described methods, in step (ii), the concentration of 4-hydroxyphenylpyruvate is maintained below 0.1 mM, 0.08 mM, 0.06 mM, 0.05 mM, 0.04 mM, 0.03 mM or 0.02 mM.

In some embodiments of the above described methods, in step (ii), the concentration of 4-hydroxyphenylpyruvate is maintained below 0.05 mM.

In some embodiments of the above described methods, in step (ii), the concentration of 4-hydroxyphenylpyruvate is maintained below 0.02 mM.

In some embodiments of the above described methods, in step (ii), the concentration of phenyllactate is maintained below 0.5 mM, 0.4 mM, 0.3 mM, 0.2 mM, or 0.1 mM.

In some embodiments of the above described methods, in step (ii), the concentration of phenyllactate is maintained below 0.2 mM.

In some embodiments of the above described methods, in step (ii), the concentration of phenyllactate is maintained below 0.1 mM.

In some embodiments of the above described methods, in step (ii), the concentration of indolelactate (indole-3-lactate), is maintained below 3 mM, 2 mM, 1 mM, 0.5 mM, 0.3 mM or 0.1 mM.

In some embodiments of the above described methods, in step (ii), the concentration of indolelactate is maintained below 1 mM.

In some embodiments of the above described methods, in step (ii), the concentration of indolelactate is maintained below 0.3 mM.

In some embodiments of the above described methods, in step (ii), the concentration of indolelactate is maintained below 0.1 mM.

In some embodiments of the above described methods, in step (ii), the concentration of indolecarboxylic acid (indole-3-carboxylate), is maintained below 1 mM, 0.8 mM, 0.6 mM, 0.4 mM or 0.2 mM.

In some embodiments of the above described methods, in step (ii), the concentration of indolecarboxylic acid is maintained below 0.5 mM.

In some embodiments of the above described methods, in step (ii), the concentration of indolecarboxylic acid is maintained below 0.2 mM.

In some embodiments of the above the above described methods, in step (ii), the concentration of homocysteine is maintained below 0.5 mM, 0.4 mM, 0.3 mM, 0.2 mM, or 0.1 mM.

In some embodiments of the above described methods, in step (ii), the concentration of homocysteine is maintained below 0.3 mM.

In some embodiments of the above described methods, in step (ii), the concentration of homocysteine is maintained below 0.1 mM.

In some embodiments of the above described methods, in step (ii), the concentration of 2-hydroxybutyric acid is maintained below 1 mM, 0.8 mM, 0.6 mM, 0.4 mM or 0.2 mM.

In some embodiments of the above described methods, in step (ii), the concentration of 2-hydroxybutyric acid is maintained below 0.5 mM.

In some embodiments of the above described methods, in step (ii), the concentration of 2-hydroxybutyric acid is maintained below 0.2 mM.

In some embodiments of the above described methods, in step (ii), the concentration of isovalerate and/or, 2-methylbutyrate, and/or isobutyrate is maintained below 2 mM, 1 mM, 0.8 mM, 0.6 mM, 0.4 mM or 0.2 mM.

In some embodiments of the above described methods, in step (ii), the concentration of isovalerate and/or, 2-methylbutyrate, and/or isobutyrate is maintained below 1 mM.

In some embodiments of the above described methods, in step (ii), the concentration of isovalerate and/or, 2-methylbutyrate, and/or isobutyrate is maintained below 0.5 mM.

In some embodiments of the above described methods, in step (ii), the concentration of formate is maintained below 4 mM, 3 mM, 2 mM, 1 mM, 0.5 mM or 0.2 mM.

In some embodiments of the v, in step (ii), the concentration of formate is maintained below 3 mM.

In some embodiments of the above described methods, in step (ii), the concentration of formate is maintained below 1 mM.

Methods Comprising Controlling the Amino Acid Concentration in the Cell Culture Medium at Low Levels In some embodiments, the method of cell culture further comprises;
(iii) maintaining at least one amino acid selected from phenylalanine, tyrosine, tryptophan, methionine, leucine, isoleucine, valine, serine, threonine and glycine below a concentration C2 in the cell culture medium, wherein C2 is 2 mM.

In some embodiments, said concentration is maintained between 0.1 mM and C2, 0.2 mM and C2, 0.3 mM and C2, 0.4 mM and C2, or 0.5 mM and C2. In some embodiments, said concentration is maintained between 0.5 mM and C2.

In some embodiments, C2 is 2 mM, 1.5 mM, 1 mM, 0.9 mM, 0.8 mM, 0.7 mM, 0.6 mM, 0.5 mM, 0.4 mM, 0.3 mM, 0.2 mM, 0.1 mM, 0.05 mM. In some embodiments, C2 is 1 mM.

Methods Comprising Measuring the Amino Acid Concentration in the Cell Culture Medium In some embodiments, step (iii) comprises the step of measuring the concentration of said at least one amino acid. The concentration of amino acid can be measured by any method known to the skilled person, including off line and on line measurement methods.

The concentration of amino acids can be measured once or several times during the cell culture. In some embodiments, the amino acid concentration is measured continuously, intermittently, every 30 min, every hour, every two hours, twice a day, daily, or every two days. In a preferred embodiment, the concentration of amino acid is measured daily.

The concentration of amino acid can be measured by any method known to the skilled person. Preferred methods to measure the concentration of amino acids in online or offline methods include for example Liquid Chromatography such HPLC, UPLC or LCMS, NMR or GCMS.

In some embodiments, the concentration of amino acid is measured off line by taking a sample of the cell culture medium and measuring the concentration of said at least one amino acid in said sample. In some embodiments, the concentration of amino acid is measured as disclosed in Example 4. A preferred method to measure the concentration of amino acids in an off line method is UPLC.

In some embodiments, the concentration of amino acid is measured online. In some embodiments, the concentration of amino acid is measured on-line using Raman spectroscopy. In some embodiments, the concentration of amino acid is measured on-line using Raman spectroscopy as disclosed in Example 7. In some embodiments, the concentration of amino acid is measured online using HPLC or UPLC based technology with an auto-sampler that draws sample from reactor and transfers to the equipment in a programmed manner.

In some embodiments, when the measured concentration is above a predefined value, the concentration of said at least one amino acid in the cell culture medium is decreased. The predefined value can be equal C2 or can be a percentage of C2. In some embodiments the percentage is 50, 55, 60, 65, 70, 75, 80, 85, 90 or 95% of C2. In some embodiments the percentage is 80% of C2.

The concentration of amino acid in the cell culture medium can be decreased by reducing the amount of amino acid provided to the cells, for example by reducing the concentration of said amino acid in the feed medium, reducing the feed rate, or reducing the number or volume of feeds. For example, the feed medium can be replaced by a feed medium comprising a lower concentration of amino acid.

Concentration of Phenylalanine, Tyrosine, Tryptophan Methionine, Leucine, Isoleucine, Valine, Serine, Threonine and Glycine in the Cell Culture Medium In some embodiments, in step (iii), the concentration of phenylalanine is maintained below 2 mM in the cell culture medium. In a preferred embodiment, the concentration of phenylalanine is maintained between 0.1 and 2 mM in the cell culture medium. In a preferred embodiment, the concentration of phenylalanine is maintained between 0.1 and 1 mM in the cell culture medium. In a preferred embodiment, the concentration of phenylalanine is maintained between 0.2 and 1 mM in the cell culture medium. In a preferred embodiment, the concentration of phenylalanine is maintained between 0.5 and 1 mM in the cell culture medium. In some embodiments, in step (iii), the concentration of tyrosine is maintained below 2 mM in the cell culture medium. In a preferred embodiment, the concentration of tyrosine is maintained between 0.1 and 2 mM in the cell culture medium. In a preferred embodiment, the concentration of tyrosine is maintained between 0.1 and 1 mM in the cell culture medium. In a preferred embodiment, the concentration of tyrosine is maintained between 0.2 and 1 mM in the cell culture medium. In a preferred embodiment, the concentration of tyrosine is maintained between 0.5 and 1 mM in the cell culture medium.

In some embodiments, in step (iii), the concentration of tryptophan is maintained below 2 mM in the cell culture medium. In a preferred embodiment, the concentration of tryptophan is maintained between 0.1 and 2 mM in the cell culture medium. In a preferred embodiment, the concentration of tryptophan is maintained between 0.1 and 1 mM in the cell culture medium. In a preferred embodiment, the concentration of tryptophan is maintained between 0.2 and 1 mM in the cell culture medium. In a preferred embodiment, the concentration of tryptophan is maintained between 0.5 and 1 mM in the cell culture medium.

In some embodiments, in step (iii), the concentration of methionine is maintained below 2 mM in the cell culture medium. In a preferred embodiment, the concentration of methionine is maintained between 0.1 and 2 mM in the cell culture medium. In a preferred embodiment, the concentration of methionine is maintained between 0.1 and 1 mM in the cell culture medium. In a preferred embodiment, the concentration of methionine is maintained between 0.2 and 1 mM in the cell culture medium. In a preferred embodiment, the concentration of methionine is maintained between 0.5 and 1 mM in the cell culture medium.

In some embodiments, in step (iii), the concentration of leucine is maintained below 2 mM in the cell culture medium. In a preferred embodiment, the concentration of leucine is maintained between 0.1 and 2 mM in the cell culture medium. In a preferred embodiment, the concentration of leucine is maintained between 0.1 and 1 mM in the cell culture medium. In a preferred embodiment, the concentration of leucine is maintained between 0.2 and 1 mM in the cell culture medium. In a preferred embodiment, the concentration of leucine is maintained between 0.5 and 1 mM in the cell culture medium.

In some embodiments, in step (iii), the concentration of isoleucine is maintained below 2 mM in the cell culture medium. In a preferred embodiment, the concentration of isoleucine is maintained between 0.1 and 2 mM in the cell culture medium. In a preferred embodiment, the concentration of isoleucine is maintained between 0.1 and 1 mM in the cell culture medium. In a preferred embodiment, the concentration of isoleucine is maintained between 0.2 and 1 mM in the cell culture medium. In a preferred embodiment, the concentration of isoleucine is maintained between 0.5 and 1 mM in the cell culture medium.

In some embodiments, in step (iii), the concentration of valine is maintained below 2 mM in the cell culture medium. In a preferred embodiment, the concentration of valine is maintained between 0.1 and 2 mM in the cell culture medium. In a preferred embodiment, the concentration of valine is maintained between 0.1 and 1 mM in the cell culture medium. In a preferred embodiment, the concentration of valine is maintained between 0.2 and 1 mM in the cell culture medium. In a preferred embodiment, the concentration of valine is maintained between 0.5 and 1 mM in the cell culture medium.

In some embodiments, in step (iii), the concentration of serine is maintained below 2 mM in the cell culture medium. In a preferred embodiment, the concentration of serine is maintained between 0.1 and 2 mM in the cell culture medium. In a preferred embodiment, the concentration of serine is maintained between 0.1 and 1 mM in the cell culture medium. In a preferred embodiment, the concentration of serine is maintained between 0.2 and 1 mM in the cell culture medium. In a preferred embodiment, the concentration of serine is maintained between 0.5 and 1 mM in the cell culture medium.

In some embodiments, in step (iii), the concentration of threonine is maintained below 2 mM in the cell culture medium. In a preferred embodiment, the concentration of threonine is maintained between 0.1 and 2 mM in the cell culture medium. In a preferred embodiment, the concentration of threonine is maintained between 0.1 and 1 mM in the cell culture medium. In a preferred embodiment, the concentration of threonine is maintained between 0.2 and 1 mM in the cell culture medium. In a preferred embodiment, the concentration of threonine is maintained between 0.5 and 1 mM in the cell culture medium.

In some embodiments, in step (iii), the concentration of glycine is maintained below 2 mM in the cell culture medium. In a preferred embodiment, the concentration of glycine is maintained between 0.1 and 2 mM in the cell culture medium. In a preferred embodiment, the concentration of glycine is maintained between 0.1 and 1 mM in the cell culture medium. In a preferred embodiment, the concentration of glycine is maintained between 0.2 and 1 mM in the cell culture medium. In a preferred embodiment, the concentration of glycine is maintained between 0.5 and 1 mM in the cell culture medium.

In some embodiments, in step (iii), the concentration of tyrosine, phenylalanine and leucine is maintained below 2 mM, preferably between 0.1 and 2 mM, between 0.1 and 1 mM, between 0.2 and 1 mM or between 0.5 and 1 mM in the cell culture medium.

In some embodiments the cell culture medium comprises 1, 2, 3, 4, 5, 6, 7, 8, 9, or 10, of glycine, proline, serine, threonine, lysine, arginine, histidine, aspartate, glutamate and asparagine at a concentration above 1 mM, 1.5 mM, 2 mM, 3 mM or 5 mM.

In some embodiments, the cell culture medium comprises one of glycine, proline, serine, threonine, lysine, arginine, histidine, aspartate, glutamate and asparagine at a concentration above 2 mM.

In some embodiments, the cell culture medium comprises one of glycine, proline, serine, threonine, lysine, arginine, histidine, aspartate, glutamate and asparagine at a concentration above 5 mM.

In some embodiments, the cell culture medium comprises 1, 2, 3, 4, 5, 6, or 7, of, proline, lysine, arginine, histidine, aspartate, glutamate and asparagine at a concentration above 1 mM, 1.5 mM, 2 mM, 3 mM or 5 mM.

In some embodiments, the cell culture medium comprises one of, proline, lysine, arginine, histidine, aspartate, glutamate and asparagine at a concentration above 2 mM.

In some embodiments, the cell culture medium comprises one of, proline, lysine, arginine, histidine, aspartate, glutamate and asparagine at a concentration above 5 mM.

In some embodiments, the cell culture medium comprises no tyrosine. In some embodiments, the cell culture is a HiPDOG culture wherein the medium comprises no tyrosine. In some embodiments, the cell culture medium is HiPDOG medium, medium used in the HipDOG process, but comprising no tyrosine. In some embodiments the cell culture medium comprises no tyrosine wherein a HiPDOG culture or process is used which comprises no tyrosine.

Concentration of Lactate and Ammonia

In some embodiments of, other metabolites inhibiting growth of cells, such as lactate and ammonia are also maintained at low levels in the cell culture medium. Methods to keep lactate and ammonia at low levels are known to the skilled person.

For example, lactate can be kept at low levels in cell culture by using methods disclosed in WO2004104186, Gagnon et al, Biotechnology and Bioengineering, Vol. 108, No. 6, June, 2011 (Gagnon et Al) or WO2004048556.

Various other strategies can be employed to restrict lactate production and/or induce lactate consumption. These include culturing cells under slightly reduced pH (6.7-7.0), culturing cells at low glucose concentrations by using alternative carbon sources including but not limited to fructose (Wlaschin & Hu, 2007) and galactose (Altamirano et al, 2006), using a cell line that has reduced protein levels of glycolytic enzymes including but not limited to hexose transporter or lactate dehydrogenase (Kim & Lee, 2007a), employing a cell line with suppressed cellular protein levels of both lactate dehydrogenase and pyruvate dehydrogenase kinase (Zhou et al, 2011), or cell line with over-expression of pyruvate carboxylase enzyme (Kim & Lee, 2007b), or with the use of inhibitors (small molecule or protein based) for signaling pathways (such as AKT (Mulukutla et al, 2012), mTOR (Duvel et al, 2010; Lee & Lee, 2012), HIF1a) that regulate the activity of energy metabolism pathways (glycolysis, TCA cycle, and redox pathway).

In some embodiments lactate is maintained at low levels by using the high-end pH-controlled delivery of glucose (HIPDOG process/HIPDOG culture) disclosed in Gagnon et al.

In some embodiments of lactate is maintained at low levels in the cell culture medium. In some embodiments, concentration of lactate in the cell culture medium is maintained below 90 mM. In a preferred embodiment, the concentration of lactate in the cell culture medium is maintained below 70 mM. In some embodiments, the concentration of lactate in the cell culture medium is maintained below 50 mM. In some embodiments, the concentration of lactate in the cell culture medium is maintained below 40 mM. In some embodiments, lactate is maintained at low levels by controlling the amount of glucose provided to the cell culture. In some embodiments, lactate is maintained at low levels by using the HIPDOG process/culture. In some embodiments, a pH sensor is used to monitor pH of the cell culture, and, in response to a rise above a predetermined pH value, glucose is fed to the cell culture. In some embodiments, the predetermined pH value is approximately 7.

Ammonia can be kept at low levels in cell culture by any method known to the skilled person such as for example the methods disclosed in Butler et Al, *Cytotechnology* 15: 87-94, 1994 or Hong et Al, Appl Microbiol Biotechnol (2010) 88:869-876. Alternatively, ammonia can be kept at low levels by using a glutamine synthetase (GS) expression system. Such systems are commercially available (Lonza) and can be used to generate recombinant cell lines. Cell lines using GS expression system demonstrate the gain of function to synthesize glutamine in vivo, thereby completely relieving cellular dependence on the externally supplied glutamine. Since the major fraction of ammonia produced in culture is from the catabolysis of externally supplied glutamine, such a gain of metabolic function reduces the levels of ammonia produced in culture.

In some embodiments of any of the ammonia is maintained at low levels in the cell culture medium. In a preferred embodiment, concentration of ammonia in the cell culture medium is maintained below 20 mM. In a preferred embodiment, the concentration of ammonia in the cell culture medium is maintained below 10 mM. In a preferred embodiment, the concentration of ammonia in the cell culture medium is maintained below 8 mM.

Cell Culture Methods

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended. In some embodiments, the cells of the cell culture comprise mammalian cells.

The present invention may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, a cell culture suitable for the present invention is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media.

Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10,000, 12,000, 15000, 20000 or 25000 liters or more, or any volume in between.

The temperature of a cell culture will be selected based primarily on the range of temperatures at which the cell culture remains viable and the range in which a high level of desired product (e.g., a recombinant protein) is produced. In general, most mammalian cells grow well and can produce desired products (e.g., recombinant proteins) within a range of about 25° C. to 42° C., although methods taught by the present disclosure are not limited to these temperatures. Certain mammalian cells grow well and can produce desired products (e.g., recombinant proteins or antibodies) within the range of about 35° C. to 40° C. In certain embodiments, a cell culture is grown at a temperature of 20, 21, 22, 23, 24, 25, 26, 27, 28, 29, 30, 31, 32, 33, 34, 35, 36, 37, 38, 39, 40, 41, 42, 43, 44 or 45° C. at one or more times during the cell culture process. Those of ordinary skill in the art will be able to select appropriate temperature or temperatures in which to grow cells, depending on the particular needs of the cells and the particular production requirements of the practitioner. The cells may be grown for any amount of time, depending on the needs of the practitioner and the requirement of the cells themselves. In some embodiment, the cells are grown at 37° C. In some embodiments, the cells are grown at 36.5° C.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

The cell culture may be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc.

At the end of the initial growth phase, at least one of the culture conditions may be shifted so that a second set of culture conditions is applied and a metabolic shift occurs in the culture. A metabolic shift can be accomplished by, e.g., a change in the temperature, pH, osmolality or chemical inductant level of the cell culture. In one non-limiting embodiment, the culture conditions are shifted by shifting the temperature of the culture. However, as is known in the art, shifting temperature is not the only mechanism through which an appropriate metabolic shift can be achieved. For example, such a metabolic shift can also be achieved by shifting other culture conditions including, but not limited to, pH, osmolality, and sodium butyrate levels. The timing of the culture shift will be determined by the practitioner of the present invention, based on protein production requirements or the needs of the cells themselves.

When shifting the temperature of the culture, the temperature shift may be gradual. For example, it may take several hours or days to complete the temperature change. Alternatively, the temperature shift may be abrupt. For example, the temperature change may be complete in less than several hours. Given the appropriate production and control equipment, such as is standard in the commercial large-scale production of polypeptides or proteins, the temperature change may even be complete within less than an hour.

In some embodiments, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture may be shifted by shifting one or more of a number of culture conditions including, but not limited to, temperature, pH, osmolality, and sodium butyrate levels. In some embodiments, the temperature of the culture is shifted. According to this embodiment, during the subsequent production phase, the culture is maintained at a temperature or temperature range that is lower than the temperature or temperature range of the initial growth phase. As discussed above, multiple discrete temperature shifts may be employed to increase cell density or viability or to increase expression of the recombinant protein.

In some embodiments, the cells may be maintained in the subsequent production phase until a desired cell density or production titer is reached. In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

The cell culture may be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc.

In some embodiments, the cells express a recombinant protein and the cell culture method of the invention comprises a growth phase and a production phase.

In some embodiments of the method of cell culture, step (ii) and/or (iii) is applied during the totality of the cell culture method. In some embodiments step (ii) and/or (iii) is applied during a part of the cell culture method. In some embodiments, step (ii) and/or (iii) is applied until a predetermined viable cell density is obtained.

In some embodiments, the cell culture method of the invention comprises a growth phase and a production phase and step (ii) and/or (iii) is applied during the growth phase. In some embodiments, the cell culture method of the invention comprises a growth phase and a production phase and step (ii) and/or (iii) is applied during a part of the growth phase. In some embodiments, the cell culture method of the invention comprises a growth phase and a production phase and step (ii) and/or (iii) is applied during the growth phase and the production phase.

In step (ii) and/or (iii), the term "maintaining" can refer to maintaining the concentration of amino acid or metabolite below C1 or C2 for the entire culture process (until harvesting) or for a part of the culture process such as for example the growth phase, a part of the growth phase or until a predetermined cell density is obtained.

The present invention also provides a method of producing cells with improved cell growth and/or productivity in cell culture comprising the steps of:
(i) identification of a cell metabolite or metabolites which are cell growth and/or productivity inhibitors,
(ii) identification of the cell metabolic pathway or pathways resulting in the synthesis of the cell growth and/or productivity inhibitors,
(iii) identification of one or more genes in the cell metabolic pathway or pathways encoding an enzyme which catalyses the synthesis of the cell growth and/or productivity inhibitors or a metabolic intermediates thereof, or one or more genes encoding an enzyme in metabolic pathways branching from or directly branching therefrom, and/or
(iv) Identification of one or more genes in the cell metabolic pathway or pathways encoding an enzyme which catalyses the synthesis of the cell growth and/or productivity inhibitors, or metabolites of the cell growth and/or productivity inhibitors or metabolic intermediate(s) of the cell growth and/or productivity inhibitors, or metabolite of the metabolic intermediate(s), or cofactors in the cell metabolic pathway or pathways or BH4 (tetrahydrobiopterin), or BH4-4a (carbinolamine), or q-BH2, and (v) modifying the expression of the one or more genes to reduce the level of synthesis of the cell growth and/or productivity inhibitors.

In some embodiments the identification of cell metabolites which are cell growth and/or productivity inhibitors comprises;

(i) measuring the concentration/level of measurable cell metabolites produced during cell culture up to maximum viable cell density, (ii) identifying the cell metabolites which are highly expressed metabolites or metabolites that accumulate to high levels/concentrations and/or which demonstrate an increased rate of metabolite production or an increased level/concentration of metabolite production during the cell culture relative to other metabolites.

Identification of cell metabolites which are highly expressed metabolites or are metabolites that accumulate to high levels/concentrations can be performed using methods for identifying and/or measuring the metabolite concentration in the cell culture medium or in the cells, for example in the cell pellet for example using one or more of or a combination of NMR, LC/MS and GC/MS techniques. For metabolomic analysis, spent media samples and the cell pellet samples can be collected and analyzed for example from single or from duplicate reactors runs, performed for each condition taken at time points throughout culture, for example up to and/or including maximum viable cell density, for example at time points of days selected from 0, 1, 2, 3, 4, 5, 7, 8, 9, 11, and 12. The relative levels (fold changes) of all measurable metabolites are measured and calculated. The relative levels are determined in both the spent media and/or cell pellet samples, and are calculated based on fold changes compared to the level of the metabolite when first detected until the desired time endpoint, usually maximum viable cell density. Metabolites accumulating to high levels are judged from a fold change cut-off of any one of greater than or equal to 10, 15, 20, 25, 30, 35, 40, 45, 50, 60, 70, 80 90 or 100 fold between the first time point the metabolite was measured and the desired time endpoint, for example maximum viable cell density. In some embodiments it is greater than or equal to 20 fold.

In some embodiments the increase in rate of metabolite production or the increased level/concentration of metabolite production is greater than or equal 2, 3, 4, 5, 6, 7, 8, 9, or 10 fold or more increased during cell culture up to maximum viable cell density. In some embodiments it is greater than or equal to 15, 20, 25, 30, 35, 40, 45 or 50 fold. In some embodiments it is greater than or equal to 40 fold. In some embodiments it is greater than or equal to 50 fold.

In some embodiments the identification of cell metabolites which are cell growth (productivity) inhibitors further comprises (i) quantifying the highly expressed metabolite production/concentration at maximum viable cell density, (ii) culturing cells with and without the presence of the quantity of highly expressed metabolite in (i), (iii) comparing maximum viable cell density or productivity during cell culture and/or maximum viable cell density and or productivity for each cell population in (ii) and determining the effect of the highly expressed metabolite on cultured cell growth and/or productivity.

Quantifying the highly expressed metabolite production/concentration at maximum viable cell density can be performed using methods for identifying and/or measuring the metabolite concentration in the cell culture medium or in the cells. In some embodiments the measurement of and/or the quantification of the metabolites, including highly expressed metabolites, is performed using liquid chromatography with mass spectrometry (LC/MS), gas chromatography with mass spectrometry (GC/MS), or nuclear magnetic resonance (NMR). In some embodiments the cell metabolites and/or highly expressed metabolites are identified from samples of the culture medium or from the culture cells during cell culture.

The measurement of and/or the quantification of metabolites or highly expressed metabolites can be carried out by using obtained purified compound forms of the metabolite or highly expressed metabolite. These compounds can be used to prepare calibration curves for the compounds at known concentrations in order to precisely correlate the measurements obtained from the methods used with the concentrations of metabolite. In this way a precise measurement of the concentration of the metabolite is determinable at any given time point in the cell culture, for example at maximum viable cell density.

The effect of quantified concentrations of highly expressed metabolite can be determined on the cell growth and/or productivity of cells in cell culture by introduction of the determined concentration into a culture of cells and comparing the effect on the cell growth and/or productivity with an otherwise identical culture lacking the introduced metabolite. For example cells, which can be cells producing a recombinant protein, can be inoculated into a culture medium spiked-in with different selected concentrations of a highly expressed metabolite, either alone or in combination with other different highly expressed metabolites at selected concentrations, these concentrations can be for example the determined concentration at maximum viable cell density or serial dilutions thereof. The pH of the culture medium may also be adjusted to 7 before inoculating the cells. The comparison can determine the existence of a negative effect of a metabolite on cell growth and/or productivity, and/or the existence of synergistic effect between metabolites on the same measures and thereby such highly expressed metabolites can be determined to be inhibitors of cell growth and/or productivity.

In some embodiments of the method of producing cells, the cell metabolic pathway or pathways is determined from the nutrient source or component of the culture medium of the highly expressed metabolite or cell metabolite or metabolites which are cell growth and/or productivity inhibitors, these fall broadly into amino acids, vitamins, inorganic salts, trace elements, vitamins, energy sources, lipids, and nucleotides, further disclosure is provided herein. The skilled person possessing the knowledge of the identity of a highly expressed metabolite which is an inhibitory metabolite and knowledge of the nutrient sources for the metabolite can apply biochemical knowledge of metabolic pathways common to the cell to deduce the relevant cell metabolic pathway or pathways which contribute to the synthesis of the growth and/or productivity inhibitors and which can include pathways leading to intermediates of the metabolite as well as pathways branching therefrom.

In some embodiments the identification of one or more genes in the cell metabolic pathway or pathways encoding an enzyme which catalyses the synthesis of the cell growth and/or productivity inhibitors or metabolic intermediates or one or more genes encoding an enzyme in metabolic pathways branching therefrom further comprises;

(i) determining the relative gene expression levels in the cell metabolic pathway or pathways, and identifying genes which are expressed at an increased or decreased level, and/or (ii) identifying genes in the cell metabolic pathway or pathways which comprise a mutation.

In some embodiments the identification of one or more genes in the cell metabolic pathway or pathways encoding an enzyme which catalyses the synthesis of the cell growth and/or productivity inhibitors or metabolic intermediates thereof or one or more genes encoding an enzyme in a metabolic pathway branching therefrom, or identification of one or more genes in the cell metabolic pathway or pathways encoding an enzyme which catalyses the synthesis of the cell growth and/or productivity inhibitors, or metabolites of the cell growth and/or productivity inhibitors or metabolic intermediate(s) of the cell growth and/or productivity inhibitors, or metabolite of the metabolic intermediate(s), or cofactors in the cell metabolic pathway or pathways for example BH4 (tetrahydrobiopterin), or BH4-4a (carbinolamine), or q-BH2, and further comprises modifying the one or more genes. In some embodiments the identification of the one or more genes comprises gene expression analysis, in some embodiments it comprises gene expression analysis of one or more genes in the identified pathway or pathways, in some embodiments it comprises gene expression analysis of all the genes in the identified pathway or pathways. In some embodiments it comprises gene expression analysis by measuring transcript abundance, in some embodiments it comprises real time quantitative PCR assay or RT-qPCR assay. RT qPCR can measure transcript abundance by amplifying a target cDNA sequence using PCR in combination with a detection reagent, for example SYBR Green. Relative gene expression levels can be determined by measuring the number of PCR cycles required for the signal from detection reagent to surpass the background and increase logarithmically. This cycle number is commonly referred to as the $C_T$ (Threshold Cycle). Low abundance transcripts have a high $C_T$ values in comparison to known control standards of transcript abundance, such as beta-actin, and vice-versa.

In some embodiments the relative gene expression level is determined by real time quantitative PCR, RT-qPCR, In some embodiments the identification of gene mutation is determined by mRNA sequencing.

In some embodiments the identified gene is expressed at an increased or decreased level higher or lower than the expression levels of a control gene, in some embodiments the level is greater than or equal to any one of 5, 10, 15, 20, 25, 30, 35, 40, 45, 50, 55, 60, 65 70, 75, 80, 85 90 or 95 percent higher or lower than the expression levels of a control gene, for example as judged by Ct value or dCt value. In some embodiments the identified gene is expressed 10% higher or lower than the expression levels of a control gene, in some embodiments 15% higher or lower, in some embodiments 20% higher or lower than the expression levels of a control gene. In some embodiments the control gene has a Ct value of equal to or between 14 and 17 and or has a Ct value of equal to or between 15 and 16 as measured by RT-qPCR, in some embodiments the control gene is beta actin. In some embodiments the identified gene has a Ct value of greater than or equal to any one of 23, 24, 25, 26, 27, 28, 29, 30 or greater than 30 as measured by RT-qPCR, in some embodiments the identified gene has a Ct value of less than or equal to any one of 14, 13, 12, 11, 10, 9, 8, 7, 6, 5, 4, 3, 2, 1 or less than 14 as measured by RT-qPCR. In some embodiments the identified gene has a dCt value of less than or equal to −1 less than or equal to 0 or less than or equal to 1 or more than or equal to any one of 1, 2, 3, 4, 5, 6, 7, 8, 9, 10 or 11 or more than or equal to 11 as measured by RT-qPCR.

In some embodiments the identification of one or more genes in the cell metabolic pathway or pathways encoding an enzyme which catalyses the synthesis of the cell growth and/or productivity inhibitors or metabolic intermediates thereof or one or more genes encoding an enzyme in a metabolic pathway branching therefrom, additionally or alternatively comprises gene mutation analysis of one or more genes in the identified pathway or pathways. In some embodiments it comprises gene mutation analysis of all the genes in the identified pathway or pathways.

In some embodiments where the one or more genes in the cell metabolic pathway or encoding an enzyme which catalyses the synthesis of the cell growth and/or productivity inhibitors or metabolic intermediates thereof or one or more genes encoding an enzyme in a metabolic pathway branching therefrom is expressed at an increased or decreased level higher or lower than the expression levels of a control gene and/or is mutated, the expression of the one or more genes is/may be modified.

In some embodiments the expression of the one or more one or more genes in the cell metabolic pathway or pathways encoding an enzyme which catalyses the synthesis of the cell growth and/or productivity inhibitor or metabolic intermediates thereof is modified.

In some embodiments one or more genes encoding an enzyme in a metabolic pathway branching from the cell metabolic pathway or pathways comprising the one or more one or more genes encoding an enzyme which catalyses the synthesis of the cell growth and/or productivity inhibitor or metabolic intermediates thereof is modified.

In some embodiments the branch arises in a node situated above the one or more one or more genes in the cell metabolic pathway or pathways encoding an enzyme which catalyses the synthesis of the cell growth and/or productivity inhibitor or metabolic intermediate thereof. In some embodiments the branch arises in a node situated below.

In some embodiments the branch arises in a node situated above the one or more one or more gene in the cell metabolic pathway or pathways encoding an enzyme which catalyses the synthesis of the cell growth and/or productivity inhibitor, in some embodiments the branch arises in a node situated below.

Figure 24:
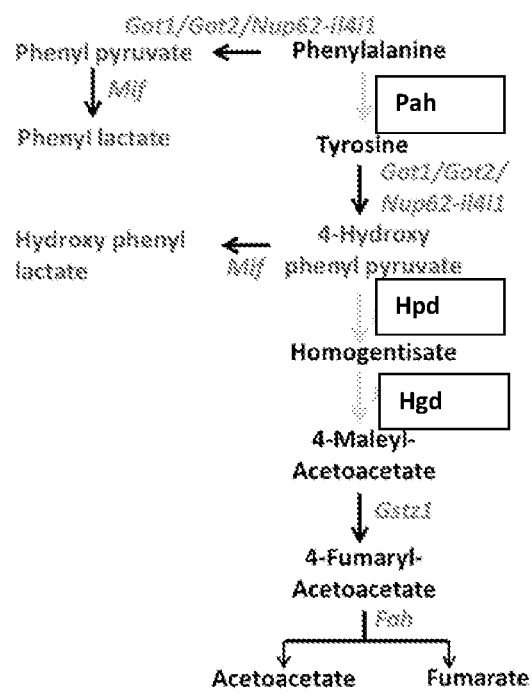
FIGS. 24 and 25 respectively show the phenylalanine/tyrosine and the leucine pathways including metabolic enzymes involved in the pathway and its branches, also tabulated is RT qPCR measure of transcript abundance indicated for the genes of the pathway as cycle number or $C_T$ (Threshold Cycle). The $C_T$ values of the metabolic genes are tabulated and compared to the $C_T$ value of a well characterized housekeeping gene, Beta Actin. The difference between the $C_T$ of the target gene and the $C_T$ of Beta Actin is tabulated as the $\Delta C_T$. High $\Delta C_T$ value indicates low gene expression level.

In some embodiments one or more genes in the cell metabolic pathway or pathways encoding an enzyme which catalyses the synthesis of the cell growth and/or productivity inhibitors, or metabolites of the cell growth and/or productivity inhibitors or metabolic intermediate(s) of the cell growth and/or productivity inhibitors, or metabolite of the metabolic intermediate(s), or cofactors in the cell metabolic pathway or pathways for example BH4 (tetrahydrobiopterin), or BH4-4a (carbinolamine), or q-BH2, is modified As illustrated in the examples the method of producing cells with improved cell growth and/or productivity in cell culture involves identifying the metabolite inhibitors produced by the cell. The method further involves identifying metabolic pathways leading to the synthesis, the point of inhibitor synthesis or leading away from this point such that metabolism is channelled to and/or from the point of inhibitor synthesis (see FIG. 24). Likewise pathways branching from these metabolic pathways are identified (see FIG. 25). Such branches may arise at nodes in the pathway situated above, below or at the point of inhibitor synthesis and likewise serve to channel metabolism towards the inhibitor and/or away from the inhibitor point of synthesis, or serve to channel metabolism towards or away from the point of synthesis of intermediates of the inhibitor synthesis. Furthermore the method as illustrated in the examples involves the identification of genes encoding enzymes in these above mentioned pathways, which includes the branches or branching pathways. These genes may encode enzymes which synthesise the inhibitor; they may encode enzymes which synthesise intermediates or upstream intermediates for the synthesis of the inhibitor; they may encode enzymes for which the inhibitor is an intermediate or an upstream intermediate for the enzyme action; or they may encode enzymes for which the inhibitor is direct intermediate or substrate for the enzyme action (for example this is illustrated in FIG. 24 by genes Hpd and Hgd) or may encode enzymes which generate cofactors in the cell metabolic pathway or pathways for example BH4 (tetrahydrobiopterin), or BH4-4a (carbinolamine), or q-BH2.

As illustrated in the examples the method further involves modifying the expression of the one or more above mentioned genes to reduce the level of synthesis of the cell growth and/or productivity inhibitors. This objective can be achieved in a number of ways as the examples illustrate. Genes encoding enzymes which synthesise the inhibitor or which synthesis intermediates in the pathway leading to the inhibitor or pathways branching therefrom, may be modified to reduce gene expression, hence reducing the metabolic channelling towards production of the inhibitor, particularly in the case when the one or more gene or genes is highly expressed. Genes encoding enzymes for which the inhibitor is a substrate or an intermediate or an upstream intermediate in the pathway leading from the inhibitor or pathways branching therefrom, may be modified to increase gene expression, hence increasing the metabolic channelling away from production of the inhibitor, particularly in the case when the one or gene or genes is under expressed and/or is mutated and/or suffers loss of function or enzyme activity. Likewise genes encoding enzymes for which an intermediate or upstream intermediate of the inhibitor synthesis is also an intermediate, i.e. genes in a pathway branching from a node located at an intermediate synthesis point upstream of the inhibitor synthesis point, may be modified to increase gene expression, hence increasing the metabolic channelling away from the pathway leading to the production of the inhibitor, particularly in the case when the one or gene or genes is under expressed and/or is mutated and/or suffers loss of function or enzyme activity.

Figure 26:
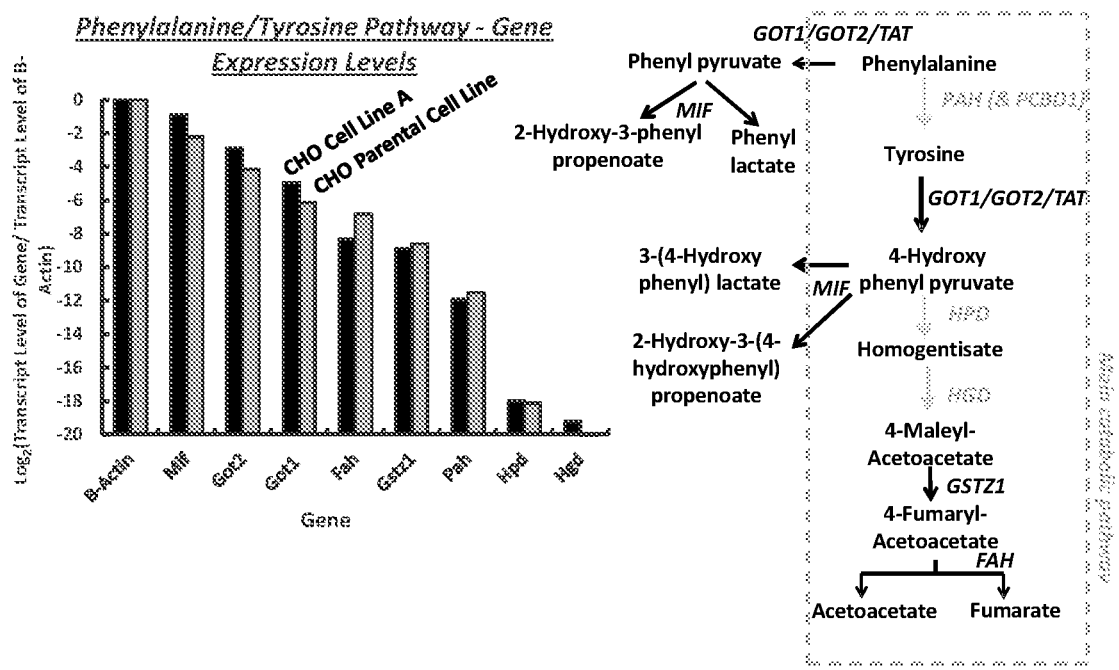
FIG. 26: Gene expression analysis of phenylalanine/tyrosine pathway genes using RT-qPCR assay. (A) Expression levels of phenylalanine/tyrosine pathway genes in CHO cell line A and CHO parental cell line. Data is plotted as log of the ration of gene of interest transcript level to B-Actin transcript level. Higher value indicates higher expression of the gene. (B) Schematic of phenylalanine/tyrosine catabolic pathway. Phenyl pyruvate, phenyllactate, 4-hydroxyphenylpyruvate and 3-(4-hydroxyphenyl)lactate are inhibitory intermediates and byproducts of the pathway. Enzymes in light grey shade are those which are expressed at very low levels.

In cases where the one or more genes identified encode an enzyme either directly synthesising the inhibitor or an intermediate to the inhibitor synthesis or metabolites of either inhibitor or intermediate it may not be desirable to modify such genes if they are involved in other important metabolic processes. This is illustrated in Example 4 (FIG. 24) with reference to genes Got1, Got2, Nup62-il4i1 and Mif, which may be expressed at normal or high levels. In this situation one or more genes in a branching pathway may be modified, for example in a pathway branching from a node located at an intermediate synthesis point upstream of the inhibitor synthesis point, to increase the metabolic channelling away from the pathway leading to the production of the inhibitor. This can be achieved by increasing the expression of genes in the branch and particularly in the case when the one or more genes in the branch is under expressed and/or is mutated and/or suffers loss of function or enzyme activity. This illustrated in Example 4 (FIG. 24) for gene Pah. As an alternative genes encoding enzymes for which the inhibitor is a substrate or an upstream intermediate may be modified to increase gene expression, hence increasing the metabolic channelling away production of the inhibitor, particularly in the case when the one or gene or genes is under expressed and/or is mutated and/or suffers loss of function or enzyme activity. This illustrated in Example 4 (FIG. 24) for genes Hpd and/or Hgd. Hence the metabolic targets for the phenylalaine/tyrosine pathway (FIG. 24) are one or more of Pah, Hpd and/or Hgd genes and/or PCDB1 and/or QDPR (FIGS. 26 and 27). These are targets for increasing expression, which can be achieved by mutation of the gene to correct loss of activity or increase activity and/or by providing an additional wild type copy or copies of the one or more genes in an expressible vector which can be introduced into the cell.

In cases where the one or more genes identified encode an enzyme either directly synthesising the inhibitor or an intermediate to the inhibitor synthesis or metabolites of either inhibitor or intermediate it may desirable to modify such genes to prevent metabolic channelling towards production of the inhibitor synthesis. As illustrated in Example 24 this can be achieved by modifying the one or more genes directly upstream from production of the inhibitor as shown for genes Bcat1 and/or Bcat2. Such modification can be by gene knockdown or gene knockout.

In one embodiment gene knockdown reduces gene expression or activity or activity of the encoded molecule to less than or equal to any of, 90, 80, 70, 60, 50, 45, 40, 35, 30, 25, 20, 15, 10, 5, 2.5 percent level of the expression or activity compared to unmodified cells.

In one embodiment Bcat1 and/or Bcat2 knockdown is to less than or equal to any of, 90, 80, 70, 60, 50, 45, 40, 35, 30, 25, 20, 15, 10, 5, 2.5 percent level of Bcat1 and/or Bcat2 expression or activity compared to unmodified cells.

Knockdown can be achieved by any one or more of of gene deletion, disruption, substitution, point mutation, multiple point mutation, insertion mutation or frameshift mutation applied to the identified gene to be expressed at a decreased level or by repression of gene expression by use of CRISPR/CAS9 or CRISPR interference or interfering RNA, interfering mRNA or interfering aptamer, or siRNA or siRNA interference or a zinc finger transcription factor or a zinc finger nuclease or a transcription activator-like effector nucleases (TALEN) or by use of an inhibitor such as a an inhibitor molecule or small molecule inhibitor, for example an activity inhibitor of protein or enzyme activity.

As also illustrated in the examples increasing the metabolic channelling away from production of the inhibitor synthesis can be achieved by modifying one or more genes encoding enzymes which themselves share an intermediate of inhibitor production as their own intermediate. As illustrated in Example 5 this can be achieved by modifying the one or more genes directly downstream from, or downstream from a node which branches out towards, the inhibitor production (FIG. 25) to increase expression. This is particularly where the one or more genes is under expressed or is mutated and suffers loss of function or enzyme activity. This is illustrated for genes Ivd, Mccc1 and/or Mccc2 where the enzymes have suffered activity altering mutation and gene Auh which is under expressed. Hence the metabolic targets for the leucine pathway are one or more of Ivd, Mccc1, Mccc2 and Auh genes. These are targets for increasing expression which can be achieved by mutation of the gene to correct loss of activity or increase activity and/or by providing a wild type copy of the one or more genes in an expressible vector which can be introduced into the cell.

According to some embodiments the modification suppresses, reduces, prevents the biosynthesis of the growth and/or productivity inhibitor and/or an intermediate thereof, in some embodiments the modification suppresses, reduces, prevents the biosynthesis of the growth and/or productivity inhibitor. According to some embodiments the modification produces cells with improved cell growth and/or productivity in cell culture.

In some embodiments modifying the expression of the one or more genes comprises;
(a) any one or more of of gene deletion, disruption, substitution, point mutation, multiple point mutation, insertion mutation or frameshift mutation applied to the identified gene which is expressed at an increased or decreased level or identified gene which comprises a mutation, or
(b) introduction of one or more nucleic acids comprising the gene into the cell, optionally as an expressible nucleic acid or vector construct,
(c) repression or activation of gene expression by use of CRISPR/CAS9 or CRISPR interference or interfering RNA, interfering mRNA or interfering aptamer, or siRNA or siRNA interference or a zinc finger transcription factor or a zinc finger nuclease or a transcription activator-like effector nucleases (TALEN).

Where modifying the expression of the one or more genes comprises use of an interfering RNA (RNAi), suitable RNAi include RNAi that decreases or increases the level of a gene product, i.e. targets the one or more genes. For example, an RNAi can be an shRNA or siRNA. A "small interfering" or "short interfering RNA" or siRNA is a RNA duplex of nucleotides that is targeted to a gene interest or the one or more genes. An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length. A "short hairpin RNA," or shRNA, is a polynucleotide construct that can be made to express an interfering RNA such as siRNA.

In some embodiments the vector contains one or more of a promoter sequence, a directional cloning site, an epitope tag, a polyadenylation sequence, and antibiotic resistance gene. In some embodiments the promoter sequence is Human cytomegalovirus immediate early promoter, the directional cloning site is TOPO, the epitope tag is V5 for detection using anti-V5 antibodies, the polyadenylation sequence is from Herpes Simplex Virus thymidine kinase, and antibiotic resistance gene is Blasticidin.

In some embodiments the cell growth and/or productivity inhibitor is selected from the group of consisting of: 3-(4-hydroxyphenyl)lactate (HPLA), 4-hydroxyphenylpyruvate, phenyllactate (PLA), indole carboxylate (indole-3-carboxylate), indole lactate (indole-3-lactate), 2-hydroxybutyric acid, homocysteine, isovalerate, 2-methylbutyrate, isobutyrate, butyrate, formate. In some embodiments the cell metabolic pathway or pathways synthesise 3-(4-hydroxyphenyl)lactate (HPLA), 4-hydroxyphenylpyruvate, phenyllactate (PLA), indole carboxylate (indole-3-carboxylate), indole lactate (indole-3-lactate), 2-hydroxybutyric acid, homocysteine, isovalerate, 2-methylbutyrate, isobutyrate, butyrate, formate, or metabolites thereof or metabolic intermediates thereof, or metabolite of the metabolic intermediate.

In some embodiments the cell metabolic pathway is the leucine pathway and/or the isoleucine pathway and/or the valine pathway or the phenylalanine/tyrosine pathway or the acetoacetate/fumerate. In some embodiments the cell metabolic pathway is the leucine pathway or the phenylalanine/tyrosine pathway. In some embodiments the cell metabolic pathway is the leucine pathway and the isoleucine pathway and the valine pathway and/or the phenylalanine/tyrosine pathway.

In some embodiments the gene modified encodes an enzyme that catalyses the synthesis of 3-(4-hydroxyphenyl) lactate (HPLA), 4-hydroxyphenylpyruvate, phenyllactate (PLA), indole carboxylate (indole-3-carboxylate), indole lactate (indole-3-lactate), 2-hydroxybutyric acid, homocysteine, isovalerate, 2-methylbutyrate, isobutyrate, butyrate, formate, or metabolites thereof or metabolic intermediates thereof, or metabolite of the metabolic intermediate.

In some embodiments the gene modified encodes an enzyme that catalyses the synthesis of 4-hydroxyphenylpyruvate or phenyllactate (PLA) or metabolites thereof or metabolic intermediates thereof, or metabolite of the metabolic intermediate.

In some embodiments the gene modified encodes an enzyme that catalyses the synthesis of s isovalerate, 2-methylbutyrate, isobutyrate, or butyrate, or metabolites thereof or metabolic intermediates thereof, or metabolite of the metabolic intermediate.

In some embodiments the one or genes modified is selected from; PCDB1, QDPR, Pah, Mif, Got1, Got2, Nup62-il4i1, Hpd, Hgd, Gstz1, Fah.

In some embodiments the one or more genes modified is selected from; Bcat1, Bcat2, Bckdha/b, Dbt/Dld, Ivd, Acadm, Mccc1, Mccc2, Auh, Hmgcl, Fasn.

In some embodiments the one or genes modified is selected from; PCDB1, QDPR, Pah, Mif, Got1, Got2, Nup62-il4i1, Hpd, Hgd, Gstz1, Fah, Bcat1, Bcat2, Bckdha/b, Dbt/Dld, Ivd, Acadm, Mccc1, Mccc2, Auh, Hmgcl, Fasn, Fasn.

In some embodiments the one or more genes modified is selected from; Hpd, Hgd and Pah, PCDB1, QDPR.

In some embodiments the one or more genes modified is selected from, Bcat1, Bcat2, Auh, Mccc1, Mccc2, Ivd.

In some embodiments the one or more genes modified is selected from, Bcat1, Bcat2, Auh, Mccc1, Mccc2, Ivd, Hpd, Hgd and Pah, PCDB1, QDPR.

In some embodiments the gene is modified to increase or decrease gene expression.

In some embodiments the gene is modified to decrease gene expression.

In some embodiments the modification (a) increases gene expression (b) increases gene expression except wherein the gene is Bcat1 and/or Bcat2, when modification decreases gene expression.

According to some embodiments there is provided a cell comprising one or more modified genes which reduces the level of synthesis of growth and/or productivity inhibitors by the cell. In some embodiments the cell comprises one or more modified genes selected from Bcat1, Bcat2, Auh, Mccc1/2, Ivd, Hpd, Hgd and Pah, PCDB1, QDPR, wherein the modification increases or decreases the gene expression, in some embodiments increases it, in some embodiments the gene expression of Bcat1 and/or Bcat2 is reduced, in some embodiments the level of synthesis of growth and/or productivity inhibitors by the cell is also reduced.

In some embodiments the one or more genes modified is Auh, or is Bcat1, or is Bcat2, or is Bcat1 and Bcat2, or is one or more of Mccc1, Mccc2 and Ivd, for example is Mccc1 or Mccc2 or Ivd optionally in combination with Auh and/or Bcat1 and/or Bcat2, or is Auh and one or more Mccc1, Mccc2 and Ivd, or is Auh, Mccc1, Mccc2 and Ivd, optionally in combination with Bcat1 and/or Bcat2. In some embodiments of the preceding embodiments the one or more genes is modified to increase gene expression, in some embodiments by mutation of the gene, in some embodiments by introduction of a copy of the wild type gene into the cell optionally as an expressible vector. In some embodiments Auh gene expression can be increased by introduction of a copy of the wild type gene, in some embodiments by mutation, alternatively by both. In some embodiments Mccc1, Mccc2, Ivd gene expression can be increased by mutation, in some embodiments by introduction of a copy of the wild type gene, alternatively by both. In some embodiments Auh gene expression is increased by introduction of a copy of the wild type gene and/or Mccc1, Mccc2, and Ivd gene expression is increased by mutation. In some embodiments the gene expression of Bcat1 and/or Bcat2 is reduced, either by gene knockdown or knockout, in some embodiments Bcat1 and/or Bcat2 knockdown is to less than or equal to any of, 90, 80, 70, 60, 50, 45, 40, 35, 30, 25, 20, 15, 10, 5, 2.5 percent level of Bcat1 and/or Bcat2 expression or activity compared to unmodified cells. In some embodiments, the one or more modified gene(s) selected from (a) Pah, PCBD1, QDPR, Mif, Got1, Got2, Nup62-il4i1, Hpd, Hgd, Gstz1, Fah, Bcat1, Bcat2, Bckdha/b, Dbt/Dld, Ivd, Acadm, Mccc1, Mccc2, Auh, Hmgcl, Fasn, Fasn, (b) Pah, PCBD1, QDPR, Mif, Got1, Got2, Nup62-il4i1, Hpd, Hgd, Gstz1, Fah, (c) Bcat1, Bcat2, Bckdha/b, Dbt/Dld, Ivd, Acadm, Mccc1, Mccc2, Auh, Hmgcl, Fasn, Fasn, (d) Bcat1, Bcat2, Auh, Mccc1, Mccc2, Ivd, Hpd, Hgd and Pah, PCDB1, QDPR, wherein the modification increases or decreases gene expression.

In some embodiments the one or more genes modified is Pah and/or PCDB1 and/or QDPR, or is one or more of Hpd and Hgd, for example Hpd, or Hgd optionally in combination with Pah and/or PCDB1 and/or QDPR, or is Pah and one or more of Hpd and Hgd or, is Pah, Hpd and Hgd. In some embodiments the one or more genes modified is selected from; (i) PCDB1, (ii) Pah, (iii) QDPR, (iv) PCBD1 and QDPR, (v) PCBD1 and Pah, (vi) Pah and QDPR, (vii) PCDB1 and Pah, and QDPR, (viii) any of (i) to (vii) and Hpd and/or Hgd. In some embodiments of the preceding embodiments the one or more genes is modified to increase gene expression. In some embodiments any one or more of Pah, PCDB1, QDPR, Hpd, Hgd gene expression can be increased by introduction of a copy of the wild type gene, in some embodiments by mutation, alternatively by both. In some embodiments Pah, PCDB1, QDPR, Hpd and Hgd gene expression is increased by introduction of a copy of the wild type gene. In some embodiments Hpd and Hgd gene expression is increased by introduction of a copy of the wild type gene. In some embodiments Pah, PCDB1 and/or QDPR gene expression is increased by introduction of a copy of the wild type gene.

In some embodiments, the one or more genes modified is Auh, Mccc1, Mccc2, Ivd, Pah, Hpd and Hgd. In some embodiments, the one or more genes modified is Auh, Mccc1, Mccc2, Ivd, Pah, PCDB1, Hpd and Hgd and optionally QDPR. In some embodiments, the one or more genes modified is Bcat1 and/or Bcat2, Pah, PCDB1, Hpd and Hgd and optionally QDPR. In some embodiments of the preceding embodiments the one or more genes is modified to increase gene expression by way of the relevant method of introduction of a copy of the wild type gene, by mutation, alternatively by both. In some embodiments Auh gene expression is increased by introduction of a copy of the wild type gene and Mccc1, Mccc2, Ivd, Pah, PCDB1, QDPR, Hpd and Hgd gene expression is increased by mutation.

The present invention further provides a cell obtained or obtainable by the method of producing cells. In some embodiments the cell comprises one or more modified genes which reduces the level of synthesis of growth and/or productivity inhibitors by the cell. In some embodiments the cell comprises one or more modified genes selected from Bcat1, Bcat2, Auh, Mccc1, Mccc2, Ivd, Hpd, Hgd and Pah, PCDB1, QDPR, wherein the modification increases or decreases the gene expression. In some embodiments gene expression is increased. In some embodiments the level of synthesis of growth and/or productivity inhibitors by the cell is also reduced.

In some embodiments of the cell obtained by the method of producing cells the one or more genes modified is Auh, or is Bcat1, or is Bcat2, or is Bcat1 and Bcat2, or is one or more of Mccc1, Mccc2 and Ivd, for example is Mccc1 or Mccc2 or Ivd optionally in combination with Auh and/or Bcat1 and/or Bcat2, or is Auh and one or more Mccc1, Mccc2 and Ivd, or is Auh, Mccc1, Mccc2 and Ivd, optionally in combination with Bcat1 and/or Bcat2. In some embodiments of the preceding embodiments the one or more genes is modified to increase gene expression, in some embodiments by mutation of the gene, in some embodiments by introduction of a copy of the wild type gene into the cell optionally as an expressible vector. In some embodiments Auh gene expression can be increased by introduction of a copy of the wild type gene, in some embodiments by mutation, alternatively by both. In some embodiments Mccc1, Mccc2, Ivd gene expression can be increased by mutation, in some embodiments by introduction of a copy of the wild type gene, alternatively by both. In some embodiments Auh gene expression is increased by introduction of a copy of the wild type gene and/or Mccc1, Mccc2, and Ivd gene expression is increased by mutation. In some embodiments the gene expression of Bcat1 and/or Bcat2 is reduced, either by gene knockdown or knockout, in some embodiments Bcat1 and/or Bcat2 knockdown is to less than or equal to any of, 90, 80, 70, 60, 50, 45, 40, 35, 30, 25, 20, 15, 10, 5, 2.5 percent level of Bcat1 and/or Bcat2 expression or activity compared to unmodified cells.

In some embodiments the one or more genes modified is Pah, and/or PCDB1 and/or QDPR, or is one or more of Hpd and Hgd, for example Hpd, or Hgd optionally in combination with Pah, and/or PCDB1 and/or QDPR, or is Pah and one or more of Hpd and Hgd. or, is Pah, Hpd and Hgd. In some embodiments the one or more genes modified is selected from; (i) PCDB1, (ii) Pah, (iii) QDPR, (iv) PCBD1 and QDPR, (v) PCBD1 and Pah, (vi) Pah and QDPR, (vii) PCDB1 and Pah, and QDPR, (viii) any of (i) to (vii) and Hpd and/or Hgd. In some embodiments of the preceding embodiments the one or more genes is modified to increase gene expression. In some embodiments Pah, PCDB1, QDPR, Hpd, Hgd gene expression can be increased by introduction of a copy of the wild type gene, in some embodiments by mutation, alternatively by both. In some embodiments Pah, PCDB1, QDPR, Hpd and Hgd gene expression is increased by introduction of a copy of the wild type gene. In some embodiments Hpd and Hgd gene expression is increased by introduction of a copy of the wild type gene. In some embodiments Pah, PCDB1, QDPR, Hpd and Hgd gene expression is increased by introduction of a copy of the wild type gene.

In some embodiments the one or more genes modified is Auh, Mccc1, Mccc2, Ivd, Pah, Hpd and Hgd. In some embodiments, the one or more genes modified is Auh, Mccc1, Mccc2, Ivd, Pah, PCDB1, Hpd and Hgd and optionally QDPR. In some embodiments, the one or more genes modified is Bcat1 and/or Bcat2, Pah, PCDB1, Hpd and Hgd and optionally QDPR. In some embodiments of the preceding embodiments the one or more genes is modified to increase gene expression by way of the relevant method of introduction of a copy of the wild type gene, by mutation, alternatively by both. In some embodiments Auh gene expression is increased by introduction of a copy of the wild type gene and Mccc1, Mccc2, Ivd, Pah, PCDB1, QDPR, Hpd and Hgd gene expression is increased by mutation.

In some embodiments the one or more genes modified is selected from Bcat1, Bcat2, Auh, Mccc1, Mccc2, Ivd, Hpd, Hgd, PCBD1, QDPR and Pah, wherein the modification increases the gene expression of one or more of Auh, Mccc1, Mccc2, Ivd, Hpd, Hgd, PCBD1, QDPR and Pah and/or reduces the gene expression of Bcat1 or Bcat2 and/or reduces the level of synthesis of growth and/or productivity inhibitors by the cell.

In some embodiments the one or more genes modified is, (i) Auh, (ii) Bcat1, (iii) Bcat2, (iv) one or more of Mccc1, Mccc2 and Ivd, (v) Bcat1 and/or Bcat2 and/or Auh and one or more Mccc1, Mccc2 and Ivd, (vi) Pah, (vii) PCBD1, (viii) PCBD1 and/or QDPR, (ix) one or more of Hpd and Hgd, (x) Pah and/or PCBD1 and one or more of Hpd and Hgd, (xi) Pah and PCBD1, and optionally QDPR, (xii) Pah, PCBD1, Hpd and Hgd, and optionally QDPR, (xiii) Bcat1 and/or Bcat2, Auh, Mccc1, Mccc2 and Ivd or, (xiv) Bcat1 and/or Bcat2, Auh, Mccc1, Mccc2, Ivd, Pah, PCBD1, Hpd, Hgd and optionally QDPR, (xv) Bcat1 and/or Bcat2. In some embodiments the modification (a) increases gene expression (b) increases gene expression except wherein the gene is Bcat1 and/or Bcat2, when modification decreases gene expression, optionally Bcat1 and/or Bcat2 knockdown is to less than or equal to any of, 90, 80, 70, 60, 50, 45, 40, 35, 30, 25, 20, 15, 10, 5, 2.5 percent level of Bcat1 and/or Bcat2 expression or activity compared to unmodified cells. In one embodiment the cells express a recombinant protein or heterologous recombinant protein.

Cells

Any cell susceptible to cell culture may be utilized in accordance with the present invention. In some embodiments, the cell is a mammalian cell. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred embodiments, the cells are GS-cells.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some embodiments, a hybridoma is a trioma cell line, which results when progeny of heterohybrid myeloma fusions, which are the product of a fusion between human cells and a murine myeloma cell line, are subsequently fused with a plasma cell. In some embodiments, a hybridoma is any immortalized hybrid cell line that produces antibodies such as, for example, quadromas (See, e.g., Milstein et al., Nature, 537:3053, 1983). One skilled in the art will appreciate that hybridoma cell lines might have different nutrition requirements and/or might require different culture conditions for optimal growth, and will be able to modify conditions as needed.

Methods Comprising Identifying and/or Measuring the Metabolite Concentration in the Cell Culture Medium or in Cells (Cell Pellet Sample)

Metabolites can be identified and/or the concentration of metabolites can be measured by any method known to the skilled person, including off line and on line measurement methods, such measurements also constitute metabolomic analysis or metabolomic measurement. Applied to the cell culture medium or to samples of the cells for instance the cell pellet The identification and/or concentration of metabolites can be measured once or several times during the cell culture. In some embodiments, the metabolite concentration is measured continuously, intermittently, every 30 min, every hour, every two hours, twice a day, daily, or every two days. In a preferred embodiment the identification and/or concentration of metabolite is measured daily.

An off line measurement method as used herein refers to a method where the measurement of a parameter such as a concentration is not automated and integrated to the cell culture method. For example, a measurement method where a sample is manually taken from the cell culture medium so that a specific concentration can be measured in said sample is considered as an off line measurement method.

Online measurement methods as used herein refer to methods where the measurement of a parameter, such as a concentration, is automated and integrated to the cell culture method.

For example, a method using the Raman spectroscopy as disclosed in Example 7 is an on-line measurement method. Alternatively, the use of High Performance Liquid Chromatography (HPLC) or Ultra Performance Liquid Chromatography (UPLC) based technology with an auto-sampler that draws samples from reactor and transfers them to the equipment in a programmed manner is an online measurement method.

The identification and/or concentration of metabolites can be measured by any method known to the skilled person. Preferred methods to identify and/or measure the concentration of metabolites in online or offline methods include for example Liquid Chromatography such as High-Performance Liquid Chromatography (HPLC), Ultra Performance Liquid Chromatography (UPLC) or Liquid Chromatography-Mass Spectrometry (LCMS), Nuclear Magnetic Resonance (NMR) or Gas Chromatography-Mass Spectrometry (GCMS).

In some embodiments, the identification and/or concentration of metabolite is measured off line by taking a sample of the cell culture medium and measuring the concentration of said at least one metabolite in said sample. In some embodiments, the identification and/or concentration of metabolites is measured as disclosed in Example 2. A preferred method to measure the identification and/or concentration of metabolites in an offline method is LCMS.

In some embodiments, the identification and/or concentration of metabolite is measured on-line. In some embodiments, the identification and/or concentration of metabolite is measured online using Raman spectroscopy. In some embodiments, the identification and/or concentration of metabolite is measured on-line using Raman spectroscopy as disclosed in Example 7. In some embodiments, the identification and/or concentration of metabolite is measured online using HPLC or UPLC based technology with an auto-sampler that draws samples from reactor and transfers them to the equipment in a programmed manner. Identification of a metabolite includes determining the presence and/or identity of the metabolite.

Improvement of Cell Growth and Productivity

In some embodiments of the above described methods, cell growth and/or productivity are increased as compared to a control culture, said control culture being identical except that it does not comprise step (ii) and/or (iii) and/or does not comprise the modified cells or the cells produced by the method of producing cells. i.e. the cells are unmodified.

In some embodiments of the above described methods, the method of the invention is a method for improving cell growth. In some embodiments, the method of the invention is a method for improving cell growth in high density cell culture at high cell density.

High cell density as used herein refers to cell density above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL, preferably above $1 \times 10^7$ cells/mL, more preferably above $5 \times 10^7$ cells/mL.

In some embodiments, the above described methods are for improving cell growth in a cell culture where cell density is above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL.

In some embodiments, the methods are for improving cell growth in a cell culture where maximum cell density is above $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL.

In some embodiments, cell growth is determined by viable cell density (VCD), maximum viable cell density, or Integrated viable cell count (IVCC). In some embodiments, cell growth is determined by maximum viable cell density.

The term "viable cell density" as used herein refers to the number of cells present in a given volume of medium. Viable cell density can be measured by any method known to the skilled person. Preferably, Viable cell density is measured using an automated cell counter such as Bioprofile Flex®. The term maximum cell density as used herein refers to the maximum cell density achieved during the cell culture.

The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

The term "Integrated viable cell count (IVCC)" as used herein refers to as the area under the viable cell density (VCD) curve. IVCC can be calculated using the following formula:

$$IVCC_{t+1} = IVCC_t + (VCD_t + VCD_{t+1}) * (\Delta t)/2$$

where $\Delta t$ is the time difference between t and t+1 time points. $IVCC_{t=0}$ can be assumed negligible. $VCD_t$ and $VCD_{t+1}$ are viable cell densities at t and t+1 time points.

The term "titer" as used herein refers, for example, to the total amount of recombinantly expressed protein produced by a cell culture in a given amount of medium volume. Titer is typically expressed in units of grams of protein per liter of medium.

In some embodiments of the above described methods, cell growth is increased by at least 5%, 10%, 15%, 20% or 25% as compared to the control culture. In some embodiments, cell growth is increased by at least 10% as compared to the control culture. In some embodiments, cell growth is increased by at least 20% as compared to the control culture.

In some embodiments of the above described methods, the productivity is determined by titer and/or volumetric productivity.

The term "titer" as used herein refers, for example, to the total amount of recombinantly expressed protein produced by a cell culture in a given amount of medium volume. Titer is typically expressed in units of grams of protein per liter of medium.

In some embodiments of the above described methods, the productivity is determined by titer. In some embodiments, the productivity is increased by at least 5%, 10%, 15%, 20% or 25% as compared to the control culture. In some embodiments, the productivity is increased by at least 10% as compared to a control culture. In some embodiments, the productivity is increased by at least 20% as compared to a control culture.

In some embodiments of the above described methods, the maximum cell density of the cell culture is greater than $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL. In some embodiments, the maximum cell density of the cell culture is greater than $5 \times 10^6$ cells/mL. In some embodiments, the maximum cell density of the cell culture is greater than $1 \times 10^8$ cells/mL.

Cell Culture Media

The terms "medium", "cell culture medium" and "culture medium" as used herein refer to a solution containing components or nutrients which nourish growing mammalian cells. Typically, the nutrients include essential and non-essential amino acids, vitamins, energy sources, lipids, and trace elements required by the cell for minimal growth and/or survival. Such a solution may also contain further nutrients or supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

A wide variety of mammalian growth media may be used in accordance with the present invention. In some embodiments, cells may be grown in one of a variety of chemically defined media, wherein the components of the media are both known and controlled. In some embodiments, cells may be grown in a complex medium, in which not all components of the medium are known and/or controlled.

Chemically defined growth media for mammalian cell culture have been extensively developed and published over the last several decades. All components of defined media are well characterized, and so defined media do not contain complex additives such as serum or hydrolysates. Early media formulations were developed to permit cell growth and maintenance of viability with little or no concern for protein production. More recently, media formulations have been developed with the express purpose of supporting highly productive recombinant protein producing cell cultures. Such media are preferred for use in the method of the invention. Such media generally comprises high amounts of nutrients and in particular of amino acids to support the growth and/or the maintenance of cells at high density. If necessary, these media can be modified by the skilled person for use in the method of the invention. For example, the skilled person may decrease the amount of phenylalanine, tyrosine, tryptophan and/or methionine in these media for their use as base media or feed media in a method as disclosed herein.

Not all components of complex media are well characterized, and so complex media may contain additives such as simple and/or complex carbon sources, simple and/or complex nitrogen sources, and serum, among other things. In some embodiments, complex media suitable for the present invention contains additives such as hydrolysates in addition to other components of defined medium as described herein.

In some embodiments, defined media typically includes roughly fifty chemical entities or components at known concentrations in water. Most of them also contain one or more well-characterized proteins such as insulin, IGF-1, transferrin or BSA, but others require no protein components and so are referred to as protein-free defined media. Typical chemical components of the media fall into five broad categories: amino acids, vitamins, inorganic salts, trace elements, and a miscellaneous category that defies neat categorization.

Cell culture medium may be optionally supplemented with supplementary components. The term "supplementary components" as used herein refers to components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, and/or glucose or other energy source. In some embodiments, supplementary components may be added to the initial cell culture. In some embodiments, supplementary components may be added after the beginning of the cell culture.

Typically, components which are trace elements refer to a variety of inorganic salts included at micromolar or lower levels. For example, commonly included trace elements are zinc, selenium, copper, and others. In some embodiments, iron (ferrous or ferric salts) can be included as a trace element in the initial cell culture medium at micromolar concentrations. Manganese is also frequently included among the trace elements as a divalent cation ($MnCl_2$ or $MnSO_4$) in a range of nanomolar to micromolar concentrations. Numerous less common trace elements are usually added at nanomolar concentrations.

In some embodiments, the medium used in the methods of the invention is a medium suitable for supporting high cell density, such as for example $1 \times 10^6$ cells/mL, $5 \times 10^6$ cells/mL, $1 \times 10^7$ cells/mL, $5 \times 10^7$ cells/mL, $1 \times 10^8$ cells/mL or $5 \times 10^8$ cells/mL, in a cell culture. In some embodiments, the cell culture is a mammalian cell fed-batch culture, preferably a CHO cells fed-batch culture.

In some embodiments, the cell culture medium comprises phenylalanine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine at a concentration below 2 mM, below 1 mM, between 0.1 and 2 mM, between 0.1 to 1 mM, between 0.5 and 1.5 mM or between 0.5 to 1 mM. In some embodiments, the cell culture medium comprises no tyrosine. In some embodiments, the cell culture medium is HiPDOG medium, medium used in the HiPDOG process, but comprising no tyrosine. In some embodiments the cell culture medium comprises no tyrosine wherein a HiPDOG culture or process is used which comprises no tyrosine.

In some embodiments, the cell culture medium comprises tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises leucine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises isoleucine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises valine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises serine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises threonine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises two of phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and tyrosine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises three of phenylalanine, tyrosine, tryptophan, methionine, leucine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine and tryptophan at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises tyrosine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises four of phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine, tryptophan and methionine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises five of phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises six of phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises seven of phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium comprises phenylalanine, tyrosine, tryptophan, methionine, leucine, isoleucine, valine, serine, threonine and glycine at a concentration below 2 mM, below 1 mM, between 0.1 and 2 mM, between 0.1 to 1 mM, between 0.5 and 1.5 mM or between 0.5 to 1 mM.

In some embodiments, the cell culture medium further comprises at least 1, 2, 3, 4, 5, 6, 7, 8, or 9, of glycine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 5 of glycine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises glycine, proline, serine, threonine, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 1, 2, 3, 4, 5, 6, or 7, of proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises at least 5 of proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium further comprises proline, lysine, arginine, histidine, aspartate, glutamate and asparagine at a concentration above 2 mM, 3 mM, 4 mM, 5 mM, 10 mM, 15 mM, preferably 2 mM.

In some embodiments, the cell culture medium comprises serine at a concentration above 3 mM, 5 mM, 7 mM, 10 mM, 15 mM or 20 mM, preferably 10 mM.

In some embodiments, the cell culture medium comprises cysteine at a concentration above 3 mM, 5 mM, 7 mM, 10 mM, 15 mM or 20 mM, preferably 10 mM.

In some embodiments, the above cell culture medium is for use in a method as disclosed herein. In some embodiments, the above cell culture medium is used in a method as disclosed herein as a base media. In some embodiments, the above cell culture medium is used a method as disclosed herein as a feed media.

Expression of Proteins

As noted above, in many instances the cells will be selected or engineered to produce high levels of desired products (e.g., recombinant protein or antibody). Often, cells will be manipulated by the hand of man to produce high levels of recombinant protein, for example by introduction of a gene encoding the protein of interest and/or by introduction of genetic control elements that regulate expression of that gene (whether endogenous or introduced).

Certain proteins may have detrimental effects on cell growth, cell viability or some other characteristic of the cells that ultimately limits production of the protein of interest in some way. Even amongst a population of cells of one particular type engineered to express a specific protein, variability within the cellular population exists such that certain individual cells will grow better, produce more protein of interest, or produce a protein with higher activity levels (e.g., enzymatic activity). In certain embodiments of the invention, a cell line is empirically selected by the practitioner for robust growth under the particular conditions chosen for culturing the cells. In some embodiments, individual cells engineered to express a particular protein are chosen for large-scale production based on cell growth, final cell density, percent cell viability, titer of the expressed protein or any combination of these or any other conditions deemed important by the practitioner.

Any protein that is expressible in a host cell may be produced in accordance with the present teachings and may be produced according to the methods of the invention or by the cells of the invention. The term "host cell" as used herein refers to a cell that is manipulated according to the present invention to produce a protein of interest as described herein. A protein may be expressed from a gene that is endogenous to the cell, or from a heterologous gene that is introduced into the cell. A protein may be one that occurs in nature, or may alternatively have a sequence that was engineered or selected by the hand of man.

Proteins that may desirably be expressed in accordance with the present invention will often be selected on the basis of an interesting or useful biological or chemical activity. For example, the present invention may be employed to express any pharmaceutically or commercially relevant enzyme, receptor, antibody, hormone, regulatory factor, antigen, binding agent, etc. In some embodiments, the protein expressed by cells in culture are selected from antibodies, or fragments thereof, nanobodies, single domain antibodies, glycoproteins, therapeutic proteins, growth factors, clotting factors, cytokines, fusion proteins, pharmaceutical drug substances, vaccines, enzymes, or Small Modular ImmunoPharmaceuticals™ (SMIPs). One of ordinary skill in the art will understand that any protein may be expressed in accordance with the present invention and will be able to select the particular protein to be produced based on his or her particular needs.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell may be produced in accordance with the present invention and may be produced according to the methods of the invention or by the cells of the invention. In some embodiments, the antibody to be expressed is a monoclonal antibody.

In some embodiments, the monoclonal antibody is a chimeric antibody. A chimeric antibody contains amino acid fragments that are derived from more than one organism. Chimeric antibody molecules can include, for example, an antigen binding domain from an antibody of a mouse, rat, or other species, with human constant regions. A variety of approaches for making chimeric antibodies have been described. See e.g., Morrison et al., *Proc. Natl. Acad. Sci. U.S.A.* 81, 6851 (1985); Takeda et al., *Nature* 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

In some embodiments, the monoclonal antibody is a human antibody derived, e.g., through the use of ribosome-display or phage-display libraries (see, e.g., Winter et al., U.S. Pat. No. 6,291,159 and Kawasaki, U.S. Pat. No. 5,658,754) or the use of xenographic species in which the native antibody genes are inactivated and functionally replaced with human antibody genes, while leaving intact the other components of the native immune system (see, e.g., Kucherlapati et al., U.S. Pat. No. 6,657,103).

In some embodiments, the monoclonal antibody is a humanized antibody. A humanized antibody is a chimeric antibody wherein the large majority of the amino acid residues are derived from human antibodies, thus minimizing any potential immune reaction when delivered to a human subject. In humanized antibodies, amino acid residues in the complementarity determining regions are replaced, at least in part, with residues from a non-human species that confer a desired antigen specificity or affinity. Such altered immunoglobulin molecules can be made by any of several techniques known in the art, (e.g., Teng et al., *Proc. Natl. Acad. Sci. U.S.A.*, 80, 7308-7312 (1983); Kozbor et al., *Immunology Today*, 4, 7279 (1983); Olsson et al., *Meth. Enzymol.*, 92, 3-16 (1982)), and are preferably made according to the teachings of PCT Publication WO92/06193 or EP 0239400, all of which are incorporated herein by reference). Humanized antibodies can be commercially produced by, for example, Scotgen Limited, 2 Holly Road, Twickenham, Middlesex, Great Britain. For further reference, see Jones et al., *Nature* 321:522-525 (1986); Riechmann et al., *Nature* 332:323-329 (1988); and Presta, *Curr. Op. Struct. Biol.* 2:593-596 (1992), all of which are incorporated herein by reference.

In some embodiments, the monoclonal, chimeric, or humanized antibodies described above may contain amino acid residues that do not naturally occur in any antibody in any species in nature. These foreign residues can be utilized, for example, to confer novel or modified specificity, affinity or effector function on the monoclonal, chimeric or humanized antibody. In some embodiments, the antibodies described above may be conjugated to drugs for systemic pharmacotherapy, such as toxins, low-molecular-weight cytotoxic drugs, biological response modifiers, and radionuclides (see e.g., Kunz et al., Calicheamicin derivative-carrier conjugates, US20040082764 A1).

In general, practitioners of the present invention will select a protein of interest, and will know its precise amino acid sequence. Any given protein that is to be expressed in accordance with the present invention may have its own particular characteristics and may influence the cell density or viability of the cultured cells, may be expressed at lower levels than another protein grown under identical culture conditions, and may have different biological activity depending on the exact culture conditions and steps performed. One of ordinary skill in the art will be able to appropriately modify the steps and compositions used to produce a particular protein according to the teachings of the present invention in order to optimize cell growth and the production and/or activity level of any given expressed protein.

Introduction of Genes for the Expression of Proteins into Host Cells

Generally, a nucleic acid molecule introduced into the cell encodes the protein desired to be expressed according to the present invention and may be introduced and expressed according to the methods of the invention or into and by the cells of the invention. Alternatively, a nucleic acid molecule may encode a gene product that induces the expression of the desired protein by the cell. For example, introduced genetic material may encode a transcription factor that activates transcription of an endogenous or heterologous protein. Alternatively or additionally, an introduced nucleic acid molecule may increase the translation or stability of a protein expressed by the cell.

Methods suitable for introducing nucleic acids sufficient to achieve expression of a protein of interest into mammalian host cells are known in the art. See, for example, Gething et al., Nature, 293:620-625, 1981; Mantei et al., Nature, 281:40-46, 1979; Levinson et al. EP 117,060; and EP 117,058, each of which is incorporated herein by reference. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216 issued Aug. 16, 1983. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988. Additional methods suitable for introducing nucleic acids include electroporation, for example as employed using the GenePulser XCell™ electroporator by BioRad™.

In some embodiments, a nucleic acid to be introduced is in the form of a naked nucleic acid molecule. For example, the nucleic acid molecule introduced into a cell may consist only of the nucleic acid encoding the protein and the necessary genetic control elements. Alternatively, a nucleic acid encoding the protein (including the necessary regulatory elements) may be contained within a plasmid vector. Non-limiting representative examples of suitable vectors for expression of proteins in mammalian cells include pCDNA1; pCD, see Okayama, et al. Mol. Cell Biol. 5:1136-1142, 1985; pMCIneo Poly-A, see Thomas, et al. Cell 51:503-512, 1987; a baculovirus vector such as pAC 373 or pAC 610; CDM8, see Seed, B. Nature 329:840, 1987; and pMT2PC, see Kaufman, et al. EMBO J. 6:187-195, 1987, each of which is incorporated herein by reference in its entirety. In some embodiments, a nucleic acid molecule to be introduced into a cell is contained within a viral vector. For example, a nucleic acid encoding the protein may be inserted into the viral genome (or a partial viral genome). Regulatory elements directing the expression of the protein may be included with the nucleic acid inserted into the viral genome (i.e., linked to the gene inserted into the viral genome) or can be provided by the viral genome itself.

Naked DNA can be introduced into cells by forming a precipitate containing the DNA and calcium phosphate. Alternatively, naked DNA can also be introduced into cells by forming a mixture of the DNA and DEAE-dextran and incubating the mixture with the cells or by incubating the cells and the DNA together in an appropriate buffer and subjecting the cells to a high-voltage electric pulse (e.g., by electroporation). A further method for introducing naked DNA cells is by mixing the DNA with a liposome suspension containing cationic lipids. The DNA/liposome complex is then incubated with cells. Naked DNA can also be directly injected into cells by, for example, microinjection.

Alternatively, naked DNA can also be introduced into cells by complexing the DNA to a cation, such as polylysine, which is coupled to a ligand for a cell-surface receptor (see for example Wu, G. and Wu, C. H. J. Biol. Chem. 263: 14621, 1988; Wilson et al. J. Biol. Chem. 267:963-967, 1992; and U.S. Pat. No. 5,166,320, each of which is hereby incorporated by reference in its entirety). Binding of the DNA-ligand complex to the receptor facilitates uptake of the DNA by receptor-mediated endocytosis.

Use of viral vectors containing particular nucleic acid sequences, e.g., a cDNA encoding a protein, is a common approach for introducing nucleic acid sequences into a cell. Infection of cells with a viral vector has the advantage that a large proportion of cells receive the nucleic acid, which can obviate the need for selection of cells which have received the nucleic acid. Additionally, molecules encoded within the viral vector, e.g., by a cDNA contained in the viral vector, are generally expressed efficiently in cells that have taken up viral vector nucleic acid. Defective retroviruses are well characterized for use in gene transfer for gene therapy purposes (for a review see Miller, A. D. Blood 76:271, 1990). A recombinant retrovirus can be constructed having a nucleic acid encoding a protein of interest inserted into the retroviral genome. Additionally, portions of the retroviral genome can be removed to render the retrovirus replication defective. Such a replication defective retrovirus is then packaged into virions which can be used to infect a target cell through the use of a helper virus by standard techniques.

The genome of an adenovirus can be manipulated such that it encodes and expresses a protein of interest but is inactivated in terms of its ability to replicate in a normal lytic viral life cycle. See, for example, Berkner et al. BioTechniques 6:616, 1988; Rosenfeld et al. Science 252:431-434, 1991; and Rosenfeld et al. Cell 68:143-155, 1992. Suitable adenoviral vectors derived from the adenovirus strain Ad type 5 d1324 or other strains of adenovirus (e.g., Ad2, Ad3, Ad7 etc.) are known to those skilled in the art. Recombinant adenoviruses are advantageous in that they do not require dividing cells to be effective gene delivery vehicles and can be used to infect a wide variety of cell types, including airway epithelium (Rosenfeld et al., 1992, cited supra), endothelial cells (Lemarchand et al., Proc. Natl. Acad. Sci. USA 89:6482-6486, 1992), hepatocytes (Herz and Gerard, Proc. Natl. Acad. Sci. USA 90:2812-2816, 1993) and muscle cells (Quantin et al., Proc. Natl. Acad. Sci. USA 89:2581-2584, 1992). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham, J. Virol. 57:267, 1986). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. Curr. Topics in Micro. and Immunol., 158:97-129, 1992). It is also one of the few viruses that may integrate its DNA into non-dividing cells, and exhibits a high frequency of stable integration (see for example Flotte et al., Am. J. Respir. Cell. Mol. Biol. 7:349-356, 1992; Samulski et al., J. Virol. 63:3822-3828, 1989; and McLaughlin et al., J. Virol. 62:1963-1973, 1989). Vectors containing as little as 300 base pairs of AAV can be packaged and can integrate. Space for exogenous DNA is limited to about 4.5 kb. An AAV vector such as that described in Tratschin et al. (Mol. Cell. Biol. 5:3251-3260, 1985) can be used to introduce DNA into cells. A variety of nucleic acids have been introduced into different cell types using AAV vectors (see for example Hermonat et al., Proc. Natl. Acad. Sci. USA 81:6466-6470, 1984; Tratschin et al., Mol. Cell. Biol. 4:2072-2081, 1985; Wondisford et al., Mol. Endocrinol. 2:32-39, 1988; Tratschin et al., J. Virol. 51:611-619, 1984; and Flotte et al., J. Biol. Chem. 268:3781-3790, 1993).

When the method used to introduce nucleic acid molecules into a population of cells results in modification of a large proportion of the cells and efficient expression of the protein by the cells, the modified population of cells may be used without further isolation or subcloning of individual cells within the population. That is, there may be sufficient production of the protein by the population of cells such that no further cell isolation is needed and the population can be immediately be used to seed a cell culture for the production of the protein. Alternatively, it may be desirable to isolate and expand a homogenous population of cells from a few cells or a single cell that efficiently produce(s) the protein. Alternative to introducing a nucleic acid molecule into a cell that encodes a protein of interest, the introduced nucleic acid may encode another polypeptide or protein that induces or increases the level of expression of the protein produced endogenously by a cell. For example, a cell may be capable of expressing a particular protein but may fail to do so without additional treatment of the cell. Similarly, the cell may express insufficient amounts of the protein for the desired purpose. Thus, an agent that stimulates expression of the protein of interest can be used to induce or increase expression of that protein by the cell. For example, the introduced nucleic acid molecule may encode a transcription factor that activates or upregulates transcription of the protein of interest. Expression of such a transcription factor in turn leads to expression, or more robust expression of the protein of interest.

In certain embodiments, a nucleic acid that directs expression of the protein is stably introduced into the host cell. In certain embodiments, a nucleic acid that directs expression of the protein is transiently introduced into the host cell. One of ordinary skill in the art will be able to choose whether to stably or transiently introduce a nucleic acid into the cell based on his or her experimental needs.

A gene encoding a protein of interest may optionally be linked to one or more regulatory genetic control elements. In certain embodiments, a genetic control element directs constitutive expression of the protein. In certain embodiments, a genetic control element that provides inducible expression of a gene encoding the protein of interest can be used. The use of an inducible genetic control element (e.g., an inducible promoter) allows for modulation of the production of the protein in the cell. Non-limiting examples of potentially useful inducible genetic control elements for use in eukaryotic cells include hormone-regulated elements (e.g., see Mader, S. and White, J. H., *Proc. Natl. Acad. Sci. USA* 90:5603-5607, 1993), synthetic ligand-regulated elements (see, e.g. Spencer, D. M. et al., *Science* 262:1019-1024, 1993) and ionizing radiation-regulated elements (e.g., see Manome, Y. et al., *Biochemistry* 32:10607-10613, 1993; Datta, R. et al., *Proc. Natl. Acad. Sci. USA* 89:10149-10153, 1992). Additional cell-specific or other regulatory systems known in the art may be used in accordance with the invention.

One of ordinary skill in the art will be able to choose and, optionally, to appropriately modify the method of introducing genes that cause the cell to express the protein of interest in accordance with the teachings of the present invention.

Isolation of the Expressed Protein

In general, it will typically be desirable to isolate and/or purify proteins expressed according to the present invention. In certain embodiments, the expressed protein is secreted into the medium and thus cells and other solids may be removed, as by centrifugation or filtering for example, as a first step in the purification process.

Alternatively, the expressed protein may be bound to the surface of the host cell. For example, the media may be removed and the host cells expressing the protein are lysed as a first step in the purification process. Lysis of mammalian host cells can be achieved by any number of means well known to those of ordinary skill in the art, including physical disruption by glass beads and exposure to high pH conditions.

The expressed protein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the protein may be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the protein during the purification process. Protease inhibitors are particularly advantageous when cells must be lysed in order to isolate and purify the expressed protein.

One of ordinary skill in the art will appreciate that the exact purification technique will vary depending on the character of the protein to be purified, the character of the cells from which the protein is expressed, and/or the composition of the medium in which the cells were grown.

Pharmaceutical Formulations

In certain preferred embodiments of the invention, produced polypeptides or proteins will have pharmacologic activity and will be useful in the preparation of pharmaceuticals. Inventive compositions as described above may be administered to a subject or may first be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. Inventive pharmaceutical compositions typically include a purified polypeptide or protein expressed from a mammalian cell line, a delivery agent (i.e., a cationic polymer, peptide molecular transporter, surfactant, etc., as described above) in combination with a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition should be sterile and should be fluid to the extent that easy syringability exists. Preferred pharmaceutical formulations are stable under the conditions of manufacture and storage and must be preserved against the contaminating action of microorganisms such as bacteria and fungi. In general, the relevant carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the purified polypeptide or protein in the required amount in an appropriate solvent with one or a combination of ingredients enumerated above, as required, followed by filtered sterilization. Generally, dispersions are prepared by incorporating the purified polypeptide or protein expressed from a mammalian cell line into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the purified polypeptide or protein can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Formulations for oral delivery may advantageously incorporate agents to improve stability within the gastrointestinal tract and/or to enhance absorption.

For administration by inhalation, the inventive compositions comprising a purified polypeptide or protein expressed from a mammalian cell line and a delivery agent are preferably delivered in the form of an aerosol spray from a pressured container or dispenser which contains a suitable propellant, e.g., a gas such as carbon dioxide, or a nebulizer. The present invention particularly contemplates delivery of the compositions using a nasal spray, inhaler, or other direct delivery to the upper and/or lower airway. Intranasal administration of DNA vaccines directed against influenza viruses has been shown to induce CD8 T cell responses, indicating that at least some cells in the respiratory tract can take up DNA when delivered by this route, and the delivery agents of the invention will enhance cellular uptake. According to certain embodiments of the invention the compositions comprising a purified polypeptide expressed from a mammalian cell line and a delivery agent are formulated as large porous particles for aerosol administration.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the purified polypeptide or protein and delivery agents are formulated into ointments, salves, gels, or creams as generally known in the art.

The compositions can also be prepared in the form of suppositories (e.g., with conventional suppository bases such as cocoa butter and other glycerides) or retention enemas for rectal delivery.

In some embodiments, the compositions are prepared with carriers that will protect the polypeptide or protein against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active polypeptide or protein calculated to produce the desired therapeutic effect in association with the required pharmaceutical carrier.

The polypeptide or protein expressed according to the present invention can be administered at various intervals and over different periods of time as required, e.g., one time per week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with a polypeptide or protein as described herein can include a single treatment or, in many cases, can include a series of treatments. It is furthermore understood that appropriate doses may depend upon the potency of the polypeptide or protein and may optionally be tailored to the particular recipient, for example, through administration of increasing doses until a preselected desired response is achieved. It is understood that the specific dose level for any particular animal subject may depend upon a variety of factors including the activity of the specific polypeptide or protein employed, the age, body weight, general health, gender, and diet of the subject, the time of administration, the route of administration, the rate of excretion, any drug combination, and the degree of expression or activity to be modulated.

The present invention includes the use of compositions for treatment of nonhuman animals. Accordingly, doses and methods of administration may be selected in accordance with known principles of veterinary pharmacology and medicine. Guidance may be found, for example, in Adams, R. (ed.), *Veterinary Pharmacology and Therapeutics*, 8$^{th}$ edition, Iowa State University Press; ISBN: 0813817439; 2001.

Pharmaceutical compositions can be included in a container, pack, or dispenser together with instructions for administration.

The following examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims. The contents of all figures and all references, patents and published patent applications cited throughout this application are expressly incorporated herein by reference.

EXAMPLES

Example 1: Identification of the Metabolic Byproducts, Accumulating in Fed-Batch Cultures, which have Inhibitory Effects on Growth of Mammalian Cells in Culture Goal:

This experiment was carried out to identify the major growth inhibitors (metabolic byproducts) accumulating in the glucose restricted and conventional fed-batch cultures of mammalian cells, using global metabolite profiling approaches.

Materials and Methods:

Cells and Medium

CHO cells comprising a glutamine synthase expression system (commercially available from Lonza) (hereafter GS-CHO, Cell line A) and expressing a recombinant antibody were used in the current experiment. Two types of medium were used in this experiment. First medium is "Medium A" which is used for inoculation of the experiment on day 0 of the culture. Second medium is "Medium B" which is the enriched nutrient media used as a feed medium for conventional and HIPDOG fed-batch processes for culture (described in the next section).

Medium A is a fortified version of insulin-free Medium 9 (U.S. Pat. No. 7,294,484, table 14), with slight differences in concentrations of sodium bicarbonate and potassium chloride, and containing Pluronic F68 instead of polyvinyl alcohol. It was fortified by adding 10% glutamine-free Medium 5 (U.S. Pat. No. 7,294,484, table 7), and by further raising the concentrations of eight amino acids (Glu, Tyr, Gly, Phe, Pro, Thr, Trp and Val). The concentrations of amino acids are listed in the Table 1 below.

TABLE 1

Concentration of Amino Acids in Medium A

| Amino Acids | Concentration in Medium A (mM) |
|---|---|
| alanine | 0.4 |
| arginine | 5.3 |
| asparagine•H2O | 21.1 |
| aspartic acid | 2.3 |
| cysteine•HCl•H2O | 0.4 |
| cystine•2HCl | 1.5 |
| glutamic acid | 0 |
| monosodium glutamate | 2.0 |
| glutamine | 0 |
| glycine | 3.6 |
| histidine•HCl•H2O | 2.7 |
| isoleucine | 5.4 |
| leucine | 9.4 |
| lysine•HCl | 8.9 |
| methionine | 3.1 |
| phenylalanine | 4.5 |
| proline | 9.1 |
| serine | 11.8 |
| threonine | 10.8 |
| tryptophan | 2.3 |
| tyrosine•2Na•2H2O | 5.1 |
| valine | 10.3 |

Medium B has the same composition as Medium 5 (U.S. Pat. No. 7,294,484, table 7), but with higher levels of the amino acids (by a factor of 2.5). The concentrations of amino acids in Medium B are shown in Table 2.

TABLE 2

Concentration of Amino Acids in Medium B

| Amino Acids | Concnetration in Medium B (mM) |
|---|---|
| alanine | 6.0 |
| arginine | 32.9 |
| asparagine•H2O | 54.0 |
| aspartic acid | 15.0 |

TABLE 2-continued

Concentration of Amino Acids in Medium B

| Amino Acids | Concnetration in Medium B (mM) |
|---|---|
| cysteine•HCl•H2O | 0.0 |
| cystine•2HCl | 4.7 |
| glutamic acid | 6.0 |
| monosodium glutamate | 0.0 |
| glutamine | 0.0 |
| glycine | 6.0 |
| histidine•HCl•H2O | 10.5 |
| isoleucine | 27.0 |
| leucine | 38.9 |
| lysine•HCl | 30.0 |
| methionine | 12.0 |
| phenylalanine | 15.0 |
| proline | 18.0 |
| serine | 45.2 |
| threonine | 24.0 |
| tryptophan | 4.8 |
| tyrosine•2Na•2H2O | 12.0 |
| valine | 24.0 |

Bioreactor Setup

Two conditions were employed including conventional fed-batch process and a glucose restricted fed-batch process. In the glucose restricted fed batch process (hereafter HIP-DOG culture), glucose was limited by using the HIPDOG technology (Gagnon et al, 2011). The pH dead-band used while the HIPDOG control was operational was 7.025+/−0.025.

The conventional process was identical to the HIPDOG process/culture with respect to inoculum cell density targeted (1E6 cells/mL), the media used, culture volume (14 the amount of feed added daily to the culture, and the process parameters including the temperature (36.5 C), pH (6.9-7.2) and the agitation rate (267 rpm). The two cultures only differed in their glucose levels. In the conventional culture, glucose was maintained at greater than 2 g/L between days 2 through 5, while in the HIPDOG culture glucose was consumed by the cells naturally until the glucose level fell to a point at which the cells began to also consume lactic acid (observed by a slight rise in pH of the culture) and the HIPDOG technology/feeding strategy commenced. Post day 5 the glucose levels in both the conditions were maintained at concentrations above 2 g/L by feeding glucose as necessary and were treated similarly until day 12. Viable cell density, lactate and ammonia concentration in the cell culture medium were measured on a daily basis for both the conditions. The base medium used is Medium A and the feed medium used was Medium B.

For metabolomic analysis, spent medium samples and the cell pellet samples were collected and analyzed from duplicate reactors runs, performed for each condition. Time points considered for the analysis include days 0, 2, 3, 5, 7, 9 and 10. Metabolomic approach used employed NMR (groups 4 and 5 of Table 3), LC/MS and GC/MS (groups 1 to 3 of table 3) techniques to assess the relative levels of metabolites at different time points of the culture. The details of the sample preparation and the type of equipment/methods used for NMR, LC/MS and GC/MS analysis are described below. The relative levels (fold changes) of all metabolites were measured and calculated. The relative levels were determined in both the spent medium and cell pellet samples, which were calculated based on fold changes compared to the level of the metabolite when first detected. The fold changes were used to identify the metabolites that were accumulating to very high levels by day 7 of the HIPDOG and the conventional fed-batch culture.

Methods for Metabolomic Analysis

Liquid/Gas Chromatography with Mass Spectrometry

Sample preparation was conducted using a methanol extraction to remove the protein fraction while allowing maximum recovery of small molecules. The resulting extract was dried under vacuum and subsequently used for sample preparation for the appropriate instrument, either LC/MS or GC/MS.

The LC/MS portion of the platform was based on a Waters ACQUITY UPLC and a Thermo-Finnigan LTQ mass spectrometer, which consisted of an electrospray ionization (ESI) source and linear ion-trap (LIT) mass analyzer. The sample was analyzed independently in both positive and negative ion modes. Sample was reconstituted in acidic conditions for positive ion mode and was gradient eluted using water and methanol, both containing 0.1% Formic acid, whereas for negative ion mode sample was reconstituted in basic extracts, which also used water/methanol, contained 6.5 mM ammonium bicarbonate for gradient elution. The MS analysis alternated between MS and data-dependent $MS^2$ scans using dynamic exclusion.

The samples destined for GC/MS analysis were re-dried under vacuum desiccation for a minimum of 24 hours prior to being derivatized under dried nitrogen using bistrimethylsilyl-triflouroacetamide (BSTFA). The GC column was 5% phenyl and the temperature ramp is from 40° to 300° C. in a 16 minute period. Samples were analyzed on a Thermo-Finnigan Trace DSQ fast-scanning single-quadrupole mass spectrometer using electron impact ionization. The instrument was tuned and calibrated for mass resolution and mass accuracy on a frequent basis.

The data was extracted from the raw mass spec data files and peaks were identified. Subsequently, the peaks were annotated and quantified (arbitrary intensity values) with compound information by comparison to library entries of purified standards or recurrent unknown entities. The combination of chromatographic properties and mass spectra gave an indication of a match to the specific compound or an isobaric entity.

NMR Sample Preparation, Data Acquisition and Processing

1000 µL of each sample was filtered using Nanosep 3K Omega microcentrifuge filter tubes for 60 minutes, and 630 µL of the filtered sample was used for NMR analysis. These filters are preserved with glycerol, and as such some trace amounts of glycerol may appear in the analysis. Internal standard solution was added to each sample solution, and the resulting mixture was vortexed for 30 s. 700 µL of the centrifuged solution was transferred to an NMR tube for data acquisition.

NMR spectra were acquired on a Varian four-channel VNMRS 700 MHz NMR spectrometer equipped with a cryogenically cooled 1H/13C triple resonance biomolecular probe with auto tuning. The pulse sequence used was a 1D-tnnoesy with a 990 ms presaturation on water and a 4 s acquisition time. Spectra were collected with 32 transients and 4 steady-state scans at 298 K.

Spectra were processed and .cnx files were generated using the Processor module in Chenomx NMR Suite 8.0. Compounds were identified and quantified using the Profiler module in Chenomx NMR Suite 8.0 with the Chenomx Compound Library version 9, containing 332 compounds. For reporting purposes, the profiled concentrations have been corrected to reflect the composition of the original sample, instead of the contents of the NMR tube. During sample preparation, each sample is diluted by introducing an internal standard and, where necessary, to increase the analyzed volume of a small sample.

Results:

Initially cells grew exponentially in both conventional and HIPDOG cultures and attained peak cells densities on day 6 and day 7, respectively, with HIPDOG culture peaking at much higher cell densities (FIG. 1). The lactate levels in the HIPDOG process/culture remained low due to application of the HIPDOG control (between day 2-day 5) whereas the lactate levels accumulated to very high levels in case of the conventional fed-batch culture. Ammonia was also maintained at low levels during the conventional and HIPDOG culture by the use of cells comprising a glutamine synthetase expression system. The titer (amount of protein of interest per liter of cell culture medium) was measured at the end of the culture (Day 12). The HIPDOG culture attained higher titer compared to the conventional process. The differences in the cell densities and titer values are likely an outcome of the differences in the lactate accumulations observed between the two cultures.

The metabolites that were accumulating to high levels on day 7 of the HIPDOG culture were identified based on the fold changes measured using the global metabolite profiling techniques. For each of the above identified metabolites, the concentration at which the metabolite affects the growth of the cell negatively was determined through spike-in experiments using purified compounds (see example 3). The results of these experiments were used to narrow the list of the putative novel inhibitors. A total of 9 inhibitors were identified by this process. The list of the 9 metabolites identified as potential inhibitors as well as their potential metabolic source in the cell culture medium are reported in Table 3.

Table 3 shows the names and the functional classes of the nine metabolites identified as putative growth inhibitors accumulating in the GS-CHO fed-batch cultures

| Group | Metabolite | Functional Class/Metabolic Source |
|---|---|---|
| 1 | 3-(4-hydroxyphenyl)lactate (HPLA) 4-hydroxyphenylpyruvate Phenyllactate (PLA) | Phenylalanine & tyrosine metabolism Phenylalanine metabolism |
| 2 | Indolelactate (indole-3-lactate) Indolecarboxylic acid (indole-3-carboxylic acid) | Tryptophan metabolism |
| 3 | Homocysteine 2-hydroxybutyric acid | Methionine metabolism |
| 4 | Isovalerate | Leucine |
| 5 | Formate | Serine, Threonine and Glycine |

Example 2: Determination of the Concentration to which the Putative Inhibitors Accumulate in Late Stages of HIPDOG Fed-Batch Cultures Goal:

This experiment was carried out to assess the concentrations of newly identified putative growth inhibitors (metabolic byproducts) at different time points in the HIPDOG fed-batch cultures of GS-CHO cells.

Materials and Methods:

Experimental setup is same as the one defined in Example 1. Quantification was performed by LC/MS and GC/MS methods for metabolites in the first two groups of Table 3 and NMR technology was used for quantification of the metabolites in groups 4 and 5. For first two groups of the metabolites listed in the metabolite column of Table 3, purified compounds were obtained commercially and solutions of these compounds at known concentrations were prepared using the Medium A as the base solvent. Using a similar LC/MS and GC/MS global metabolite profiling approach as that used for inhibitor identification and relative quantification (see Example 1), independent calibration curves for four metabolites were prepared. These calibration curves are mathematical correlations of the actual amounts of the metabolite used in LC/MS and GS/MS techniques to the intensity values generated by the same. The correlations are subsequently used along with the intensity values generated in Example 1 to calculate the concentration of the metabolites at different time points in the culture.

Results:

The concentrations of newly identified metabolites from the first two groups of Table 3 were determined using the calibration curves developed, and the concentrations for the metabolites listed in groups 4 and 5 were determined by NMR technology as discussed in the Materials and Methods section of Example 1. The concentration of six putative inhibitors (phenyllactate, 3-(4-hydroxyphenyl)lactate, 4-hydroxyphenylpyruvate, indolelactate, isovalerate and formate) on day 7 of the HIPDOG fed-batch cultures are listed Table 4.

TABLE 4 concentrations of six metabolites on day 7 of the HIPDOG culture

| Metabolite | Day 7 Concentration (mM) |
|---|---|
| 3-(4hydroxyphenyl)lactate (HPLA) | 0.38 |
| 4-hydroxyphenylpyruvate | 0.08 |
| Phenyllactate (PLA) | 0.20 |
| Indolelactate | 0.26 |
| Isovalerate | 2.41 |
| Formate | 3.97 |

Example 3: Experiment to Establish the Growth Suppressive Effect of Identified Putative Inhibitors at the Concentrations Detected on Day 7 of the HIPDOG Fed-Batch Culture Goal:

This experiment was carried out to assess the effect of the newly identified putative inhibitors, at the concentrations determined on day 7 of the HIPDOG culture, on growth of GS-CHO cells in culture. The independent effect of the nine metabolites (phenyllactate, 3-(4-hydroxyphenyl)lactate, 4-hydroxyphenylpyruvate, indolelactate, indolecarboxylic acid, homocysteine, 2-hydroxybutyric acid, isovalerate and formate) on growth of cells was tested first. Subsequently, synergistic effect for four metabolites (phenyllactate, 3-(4-hydroxyphenyl)lactate, 4-hydroxyphenylpyruvate and indolelactate) on cell growth was tested.

Materials and Methods:

GS-CHO cells producing a recombinant antibody were inoculated at low viable cell densities (0.1E6 cells/mL) in various conditions in 5 ml volume, 6-well plate cultures. These conditions include fresh Medium A or fresh Medium A spiked-in with four putative inhibitors at concentrations detected on day 7 of the HIPDOG culture of Example 1 (phenyllactate at 0.2 mM, 3-(4-hydroxyphenyl)lactate at 0.38 mM, 4-hydroxyphenylpyruvate at 0.08 mM and indolelactate at 0.26 mM). In a separate experiment, GS-CHO cells producing a recombinant antibody were inoculated at low viable cell densities in fresh Medium A spiked-in with different concentrations of 9 inhibitors (indolecarboxylic acid, homocysteine, 2-hydroxybutyric acid, phenyllactate, 3-(4-hydroxyphenyl)lactate, 4-hydroxyphenylpyruvate, indolelactate, isovalerate and formate) with one inhibitor at a time per condition. The pH of the Medium A, spiked-in with any one of the nine metabolites or any combination of the nine metabolites, was adjusted to 7 before inoculating the cells (on day 0). The concentrations tested are:

- indolecarboxylic acid: 0, 0.5 and 1 mM
- homocysteine: 0, 0.5 and 1 mM
- 2-hydroxybutyric acid: 0, 1 and 5 mM
- phenyllactate: 0, 1 and 5 mM
- 3-(4-hydroxyphenyl)lactate: 0, 0.1, 0.3, 0.5, 1 and 5 mM
- 4-hydroxyphenylpyruvate: 0, 0.05, 0.1 and 0.25 mM
- indolelactate: 0, 1 and 3 mM
- isovalerate: 0, 1, 2.5 and 5 mM
- formate: 0, 2, 4 and 6 mM For indolelactate, the stock solution (500 mM) was prepared in DMSO. Hence, pure DMSO spike-in conditions ('DMSO cont' or DMSO control) were included for every concentration of indolelactate tested, so as to control for the effect of DMSO on the growth of the cells. All the conditions were run in duplicates or triplicates. Growth of the cells in above described conditions was monitored for 5 or 6 days.

Results:

The independent effect of the all the nine inhibitors on growth of the GS-CHO cells was investigated (FIG. 2, FIG. 3, FIG. 4 and FIG. 5). Indolecarboxylic acid and 4-hydroxyphenylpyruvate were observed to have a potent negative effect on growth of cells at concentrations of 1 mM or lower. Modest inhibition of growth was observed when GS-CHO cells were exposed to either homocysteine, 2-hydroxybutyric acid or 3-(4-hydroxyphenyl)lactate at concentrations higher than 0.5 mM or 1 mM. L-phenyllactate had a mild effect on growth of cells at 1 mM concentration. Indolelactate showed little or no effect on growth of cells at concentrations of 3 mM or below. Formate had a negative effect on growth at concentrations 2 mM and beyond. Isovalerate had a significant negative effect on growth of cells at concentrations above 1 mM.

Figure 6:
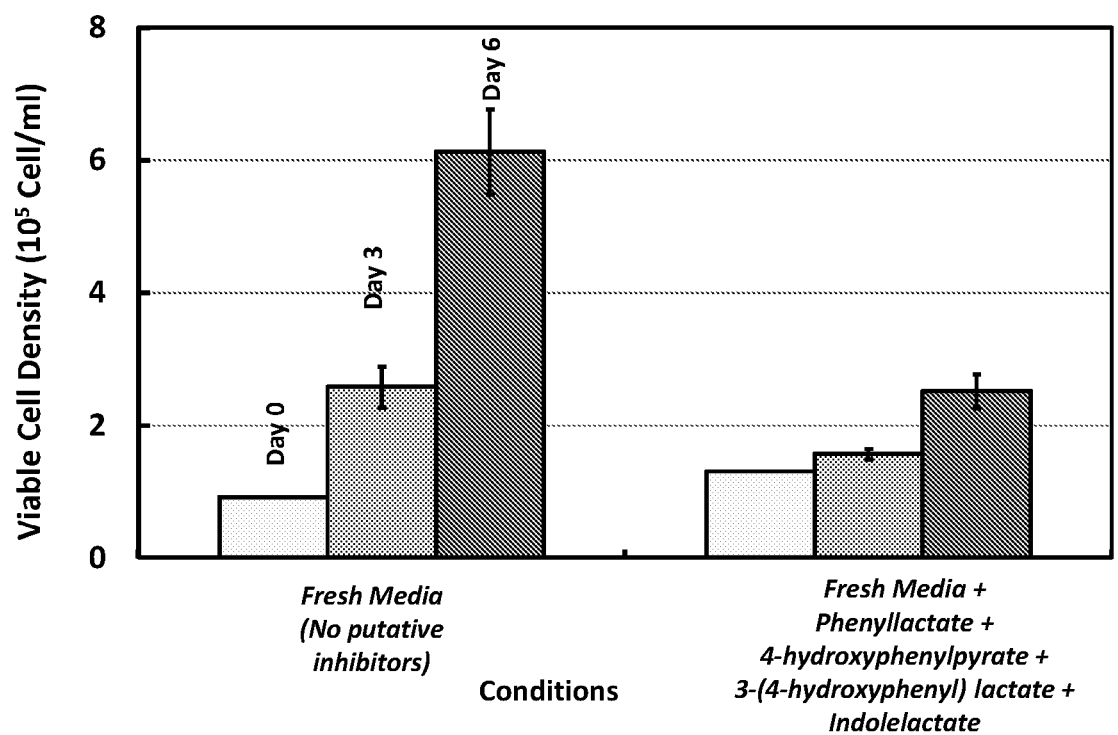
FIG. 6 shows the effect of four metabolites (4-hydroxyphenylpyruvate, indolelactate, phenyllactate, and 3-(4-hydroxyphenyl)lactate) on viable cell density of GS-CHO cells as compared to a control where cells are cultured in the absence of the metabolites. GS-CHO cells were inoculated in Medium A at low viable cell densities and were treated with fresh media alone or fresh media comprising the above mentioned four metabolites in combination at concentrations that were detected on day 7 of the HiPDOG culture (See Table 4). The effect of the inhibitors on growth of the cells was monitored for 6 days.

Earlier experiments showed that the concentration at which cell growth is inhibited was much higher when each of the nine putative inhibitors were added independently than the concentration observed on day 7 of the HIPDOG fed-batch culture. Therefore, the effect of these inhibitors when treated in combination was subsequently investigated. Interestingly, on treating the cells with the combination of four [phenyllactate, 4-hydroxyphenylpyruvate, 3-(4-hydroxyphenyl)lactate, indolelactate] of the nine metabolites, at concentrations detected on day 7 of HIPDOG culture, the cell growth was significantly inhibited when compared to cell growth in the fresh medium (FIG. 6). This data indicates that the above four metabolites act in a synergistic manner to inhibit the growth of the cells. The above mentioned nine metabolites are by-products of phenylalanine, tyrosine, tryptophan, leucine, serine, threonine methionine and glycine metabolism. Identifying the enzymes in these pathways that contribute to the biosynthesis of the inhibitors provides a strategy to genetically modify the cells to suppress the production of the same by gene modification.

Since these four metabolites are by-products of phenylalanine, tyrosine and tryptophan metabolism, reducing the concentrations of these precursor amino acids in culture can limit the formation of corresponding inhibitory metabolites. Further, since methionine metabolites (homocysteine and 2-hydroxybutyrate) and leucine, serine, threonine and glycine metabolites (isovalerate and formate) also have a negative effect on cell growth, reducing methionine, leucine, serine, threonine and glycine levels in culture could potentially limit the formation of these metabolites and promote cell growth.

Example 4: Reduction of the Growth Suppressive Effect of the Newly Identified Inhibitors by Nutrient Limitation Strategies in Fed-Batch Culture Goal:

This experiment was performed to reduce the formation of newly identified inhibitors by limiting the supply of the carbon sources responsible for their biosynthesis. The goal of this experiment was to assess if such reduction in inhibitor formation relieves the growth suppression in the late stages of the culture, resulting in increased maximum viable cell densities in the fed-batch cultures.

Materials and Methods:

Cells and Bioreactor Setup

GS-CHO cells expressing a recombinant antibody (cell line A) were used in the current experiment. Two conditions were tested as part of this experiment: A) HIPDOG fed-batch culture with low levels of four amino acids ((tyrosine, methionine, phenylalanine and tryptophan) (Low AA condition)), B) HIPDOG fed-batch culture with normal amino acids concentrations (control HIPDOG condition/culture). Exponentially growing cells from seed culture were inoculated at $1\times10^6$ cells/mL into each production bioreactor. For both the conditions, HIPDOG strategy was in operation between day 2 and day 7 of the culture. In the low amino acid condition, the concentrations of tyrosine, tryptophan, phenylalanine and methionine were maintained between 0.5 mM and 1 mM for first seven days of the culture after which they were adjusted to the levels of each of those amino acids in the control HIPDOG condition. Post day 7 both the conditions were treated similarly. Viable cell density, lactate, ammonia and amino acid concentrations were measured on a daily basis (amino acids measured only for first seven days). For both conditions, the inoculum viable cell density targeted ($1\times10^6$ cells/mL), and the culture volume (1 L) and the process parameters including the temperature (36.5 C), pH (6.9-7.2) and the agitation rate (267 rpm) were identical. The base medium used in the control HIPDOG condition was Medium A and that used in Low AA condition was the modified version of Medium A with low concentrations of the four amino acids (tyrosine, tryptophan, phenylalanine and methionine at approximately 0.6 mM). The feed medium used for control HIPDOG culture was Medium B. For the Low AA condition, either the original Medium B or a modified version of Medium B with higher concentration of four amino acids (tyrosine, tryptophan, methionine and phenylalanine) was formulated and used as feed media (60% higher for methionine and ~100% higher levels for tyrosine, tryptophan and phenylalanine as compared to original feed Medium B). The levels of the four amino acids in the modified version of Medium B was configured based on the cell specific consumption rates for the four amino acids and the previously determined feeding schedule for the cell line A in a HIPDOG process of culture. Amino acid concentrations were measured every day using a UPLC based amino acid method which is described in detail below. Based on the level of amino acids at a given sampling point and the feeding schedule, one of the two types of medium B (original or higher concentration) was chosen as the feed medium till next sampling point such that the concentration for the four amino acids are between 0.5 mM-1 mM at the next sampling time point.

Amino Acid Analysis

10 µL of either a standard amino acid mix solution or a spent medium sample (10 times diluted sample) was mixed with 70 µL of AccQ•Tag Ultra borate buffer (Waters UPLC AAA H-Class Applications Kit [176002983]), and 20 µL of AccQ•Tag reagent previously dissolved in 1.0 mL of AccQ•Tag Ultra reagent diluent was added. The reaction was allowed to proceed for 10 min at 55° C. Liquid chromatographic analysis was performed on a Waters Acquity UPLC system, equipped with a binary solvent manager, an autosampler, a column heater and a PDA detector. The separation column was a Waters AccQ•Tag Ultra column (2.1 mm i.d.×100 mm, 1.7 µm particles). The column heater was set at 55° C., and the mobile phase flow rate was maintained at 0.7 mL/min. Eluent A was 10% AccQ•Tag Ultra concentrate solvent A, and eluent B was 100% AccQ•Tag Ultra solvent B. The nonlinear separation gradient was 0-0.54 min (99.9% A), 5.74 min (90.0% A), 7.74 min (78.8% A), 8.04-8.64 min (40.4% A), 8.73-10 min (99.9% A). One microliter of sample was injected for analysis. The PDA detector was set at 260 nm. The previously determined elution times for the amino acids are used to identify the specific amino acid peaks on the chromatogram for each sample. The amino acid concentrations were estimated using the area under the peak and the calibration curve generated using the standard solution (Amino Acids Standard H, Thermo Scientific, PI-20088).

Figure 7A:
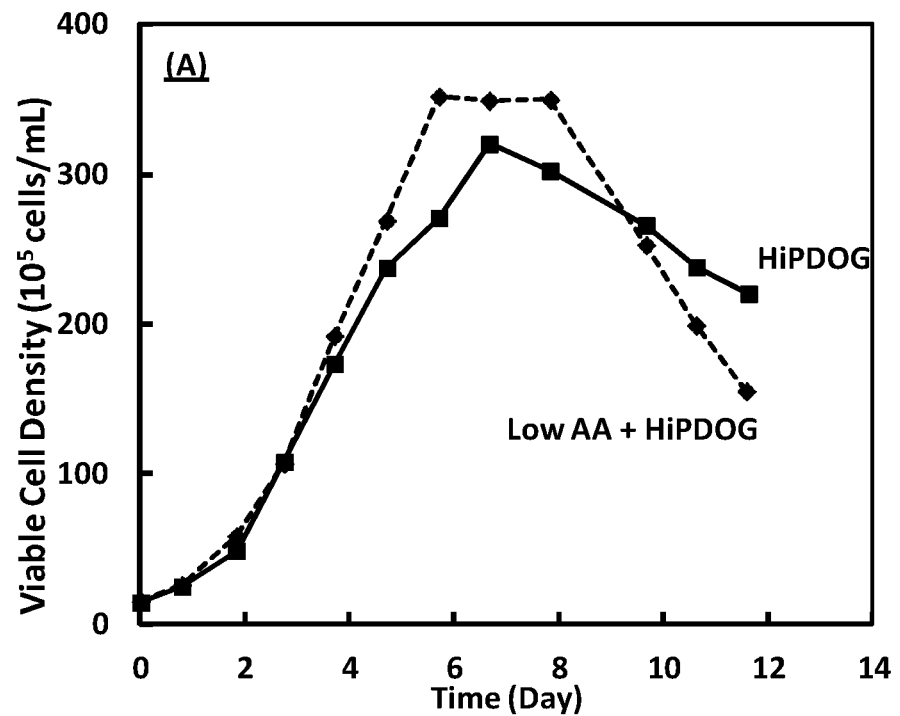
FIG. 7A shows the viable cell densities of GS-CHO cells in 'HiPDOG' process (closed squares) and 'Low AA+HiPDOG' (closed diamonds) process.
Figure 7B:
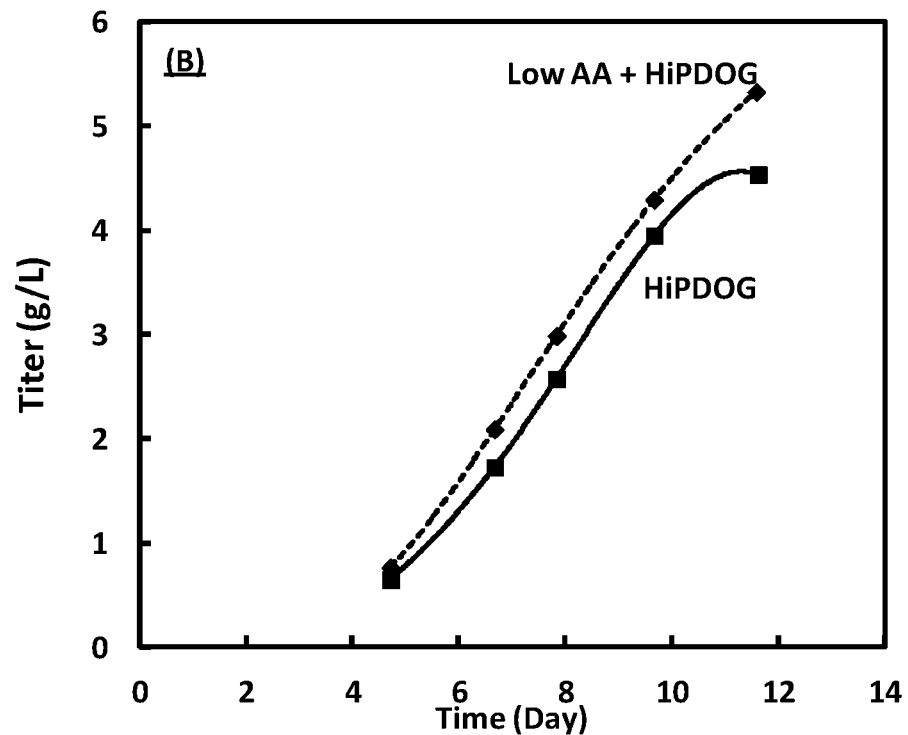
FIG. 7B shows the culture titer (IgG) at different days in 'HiPDOG' process (closed squares) and 'Low AA+HiPDOG' (closed diamonds) process.
Figures 8A, 8B:
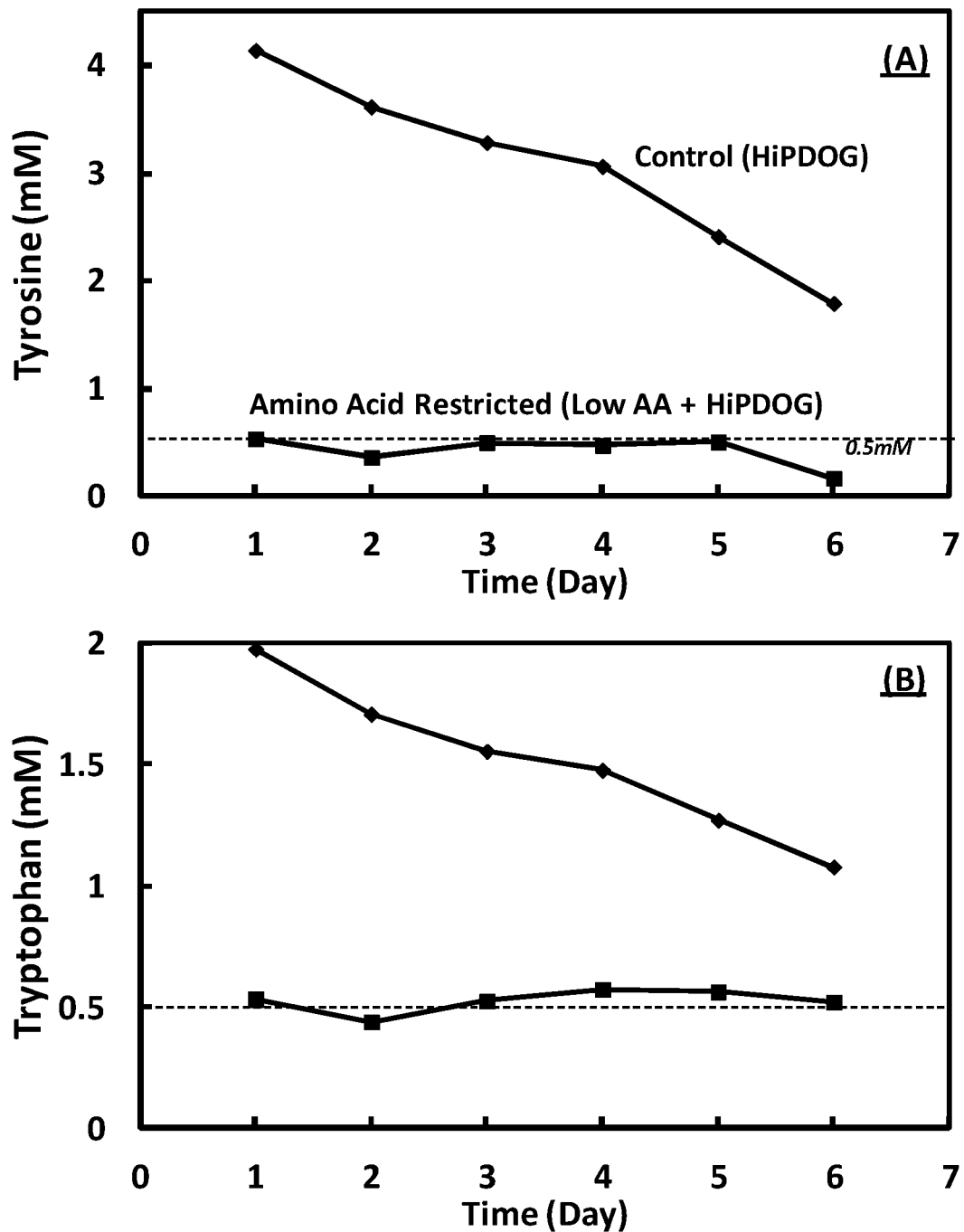
FIGS. 8 and 9 show the amino acid concentrations of four amino acids in 'amino acid restricted HiPDOG process (Low AA+HiPDOG)' (closed squares) and the 'HiPDOG' process (closed diamonds). The four amino acids include tyrosine (FIG. 7A), tryptophan (FIG. 8B), phenylalanine (FIG. 9A), and methionine (FIG. 9B).
Figures 9A, 9B:
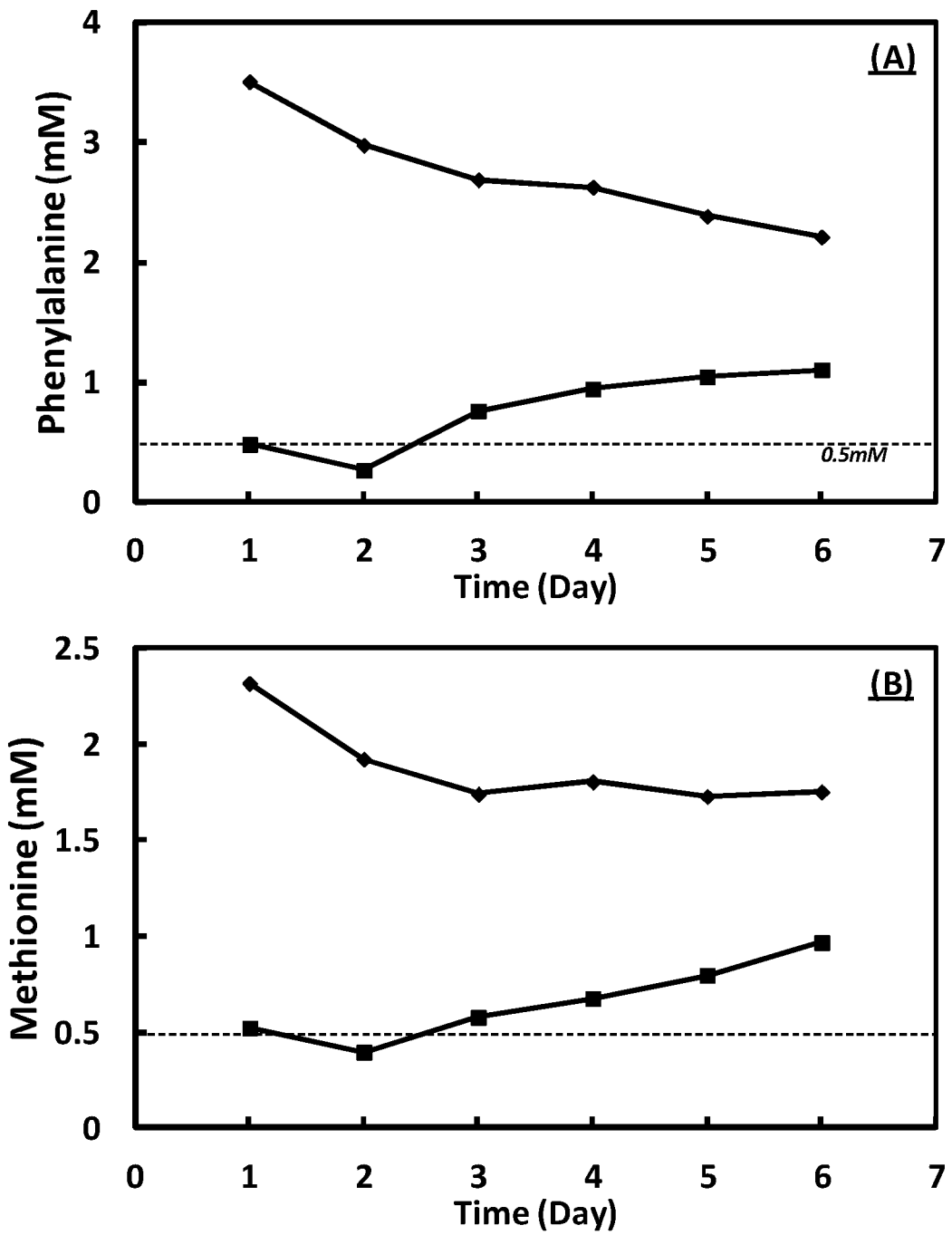

Results:

The concentrations of the amino acids were successfully maintained between 0.5 mM-1 mM in Low AA conditions (FIG. 8 and FIG. 9). The amino acid concentrations in the control HIPDOG process remained high over the course of the culture. As shown in FIG. 7, the cell densities in the Low AA condition peaked around $35 \times 10^6$ cells/ml on day 7 whereas the cell densities in control HIPDOG condition peaked around $32 \times 10^6$ cells/mL. The harvest titer levels in the Low AA condition (5.3 g/L) were 18% higher than the control condition (4.5 g/L). Clearly, limiting the amino acid supply increased the cell densities (and thereby the titer) in the late stages of the cultures.

Example 5 demonstrates that such an increase in growth and productivity can be explained as a result of reduced production of the newly identified inhibitors.

Example 5: Demonstrating (i) the Reduced Accumulation of the Newly Identified Inhibitors Through the Limitation of Amino Acids and (ii) the Reproducibility of the Positive Effect of Such Limitation of Inhibitory Metabolites on Growth of GS-CHO Cells (Cell Line A) in Fed-Batch Cultures Goal:

The main goal of this example was to demonstrate the reduction in the accumulation of the newly identified inhibitors in fed-batch cultures by limiting the supply of the carbon sources (amino acids) responsible for their biosynthesis. In this example, two experiments are included to demonstrate that such reduction in the levels of the newly identified inhibitors through limitation of four amino acids or eight amino acids relieves the growth suppression in the late stages of the fed-batch culture resulting in increased maximum viable cell densities.

Materials and Methods:

Cells and Bioreactor Setup

Cell line A was used in the two experiments performed as part of this example. Three conditions were tested in the first experiment:
A) HIPDOG fed-batch culture with low levels of tyrosine, methionine, phenylalanine and tryptophan (Low 4AA+HIPDOG condition for culture),
B) HIPDOG fed-batch culture with low levels of tyrosine, methionine, phenylalanine, tryptophan, leucine, serine, threonine and glycine (Low 8AA+HIPDOG condition), and,
C) two HIPDOG fed-batch cultures with normal amino acids concentrations (HIPDOG 1 and HIPDOG 2).

In a second experiment two conditions were tested:
A) HIPDOG fed-batch culture with low levels of tyrosine, methionine, phenylalanine, tryptophan, leucine, serine, threonine and glycine (Low 8AA+HIPDOG condition), and,
B) HIPDOG fed-batch culture with low levels of tyrosine, methionine, phenylalanine and tryptophan (Low 4AA+HIPDOG condition).

First experiment was run for 12 days whereas the second experiment was run for 16 days.

In both the experiments, exponentially growing cells from seed cultures were inoculated at $1 \times 10^6$ cells/mL into each production bioreactor. For all the conditions, HIPDOG control was in operation between day 2 and day 7 of the culture. In the low amino acid conditions, the concentrations of above mentioned four or eight amino acids were maintained between 0.5 mM and 1 mM for first seven days of the culture after which they were adjusted to the levels closer to the respective amino acids in the control HIPDOG conditions. Post day 7, both the conditions were treated similarly. Viable cell, ammonia and amino acid concentrations were measured on daily basis. For all the conditions, the inoculum viable cell density targeted ($1 \times 10^6$ cells/mL), the culture volume (14 and the process parameters including the temperature (36.5 C), pH (6.9-7.2) and agitation rate (259 rpm) were identical. The base medium used in the HIPDOG condition was Medium A and that used in low amino acid conditions was the modified version of Medium A with low concentrations of either four amino acids (tyrosine, tryptophan, phenylalanine and methionine at approximately 0.6 mM) or eight amino acids (tyrosine, tryptophan, phenylalanine, methionine, leucine, serine, threonine and glycine at approximately 0.6 mM). The feed medium used for all the conditions was Medium B. Amino acid concentrations were measured every day using UPLC based amino acid method as described in Example 4. In the low amino acid conditions, based on the level of amino acids at a given sampling point and the feeding schedule to be followed, concentrated solutions of the amino acids were supplemented to the conditions such that the concentration for the four amino acids or the eight amino acids in corresponding low amino acid conditions are between 0.5 mM-1 mM at the next sampling time point. Spent medium samples from various conditions across both the experiments were analyzed for the levels of the newly identified inhibitors using the NMR technology described in the Materials and Methods section of Example 1.

Figures 15A, 15B:
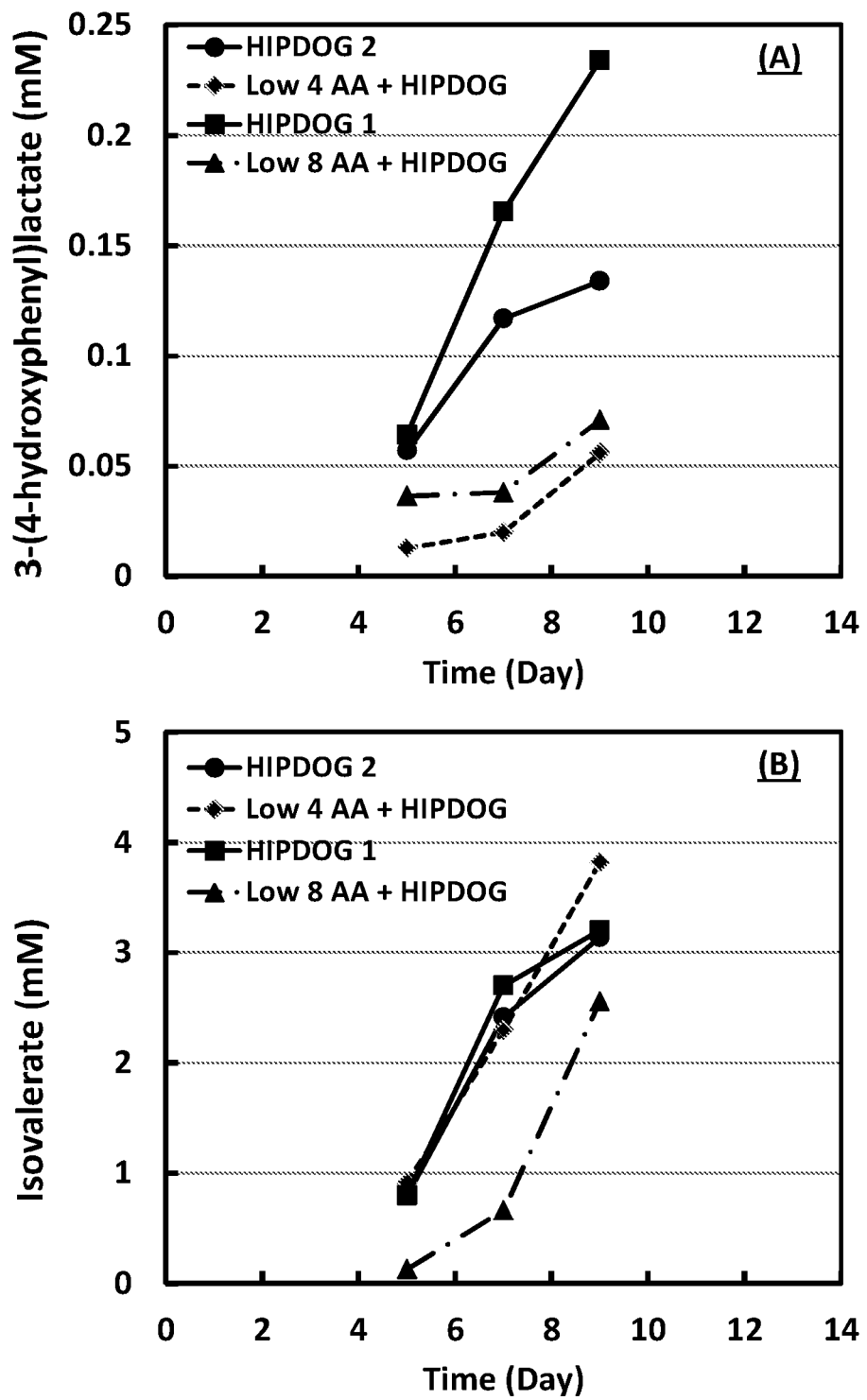
FIGS. 15 and 16 show the concentration of 3-(4-hydroxyphenyl)lactate (FIG. 15A), isovalerate (FIG. 15B) and indole-3-lactate (FIG. 16) at day 5, day 7 and day 9 of the cell culture of GS-CHO cells using conditions disclosed in Example 5 ((HiPDOG1 (closed squares), HiPDOG2 (closed circles), Low 4AA+HipDOG (closed diamonds), Low 8AA+HipDOG (closed triangles)).
Figure 16:
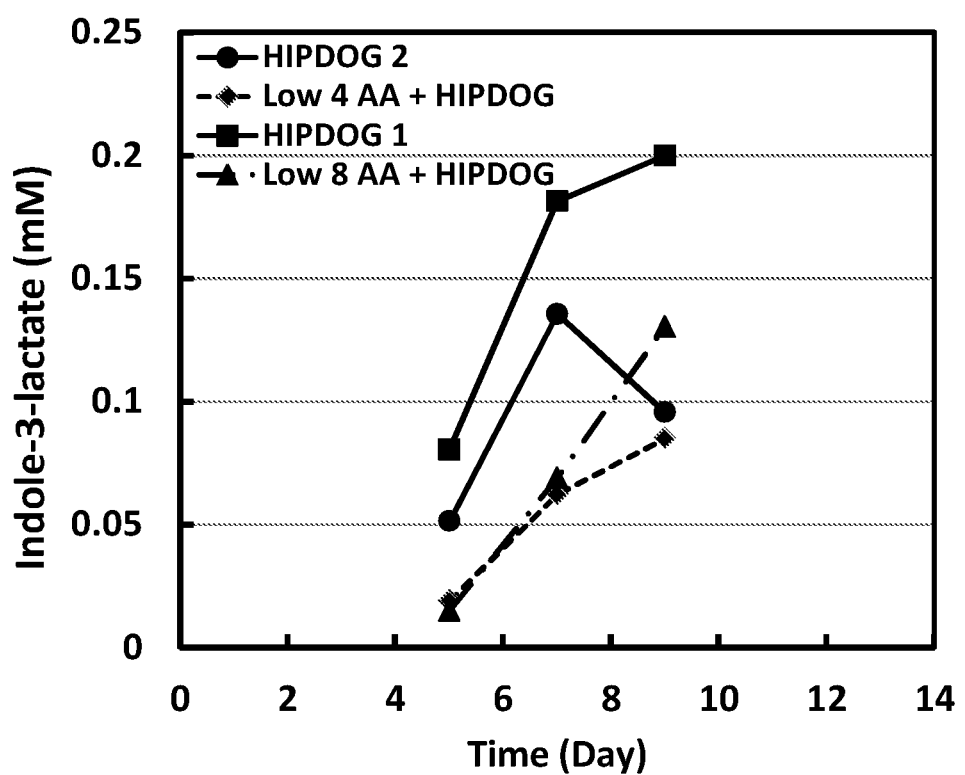

Results:

In the first experiment, the concentrations of the amino acids were successfully maintained between 0.5 mM-1 mM in both Low 4 AA and Low 8 AA conditions until day 7 of the fed-batch cultures (FIGS. 11-14). Such limitation of amino acid levels in the two conditions resulted in lower levels of accumulation of the newly identified metabolites (FIG. 15 and FIG. 16). Isovalerate, formate, 3-(4-hydroxyphenyl)lactate and indole-3-lactate were specifically profiled. Isovalerate and formate are byproducts of leucine, serine, glycine and threonine, which are controlled at low levels only in Low 8 AA condition. These amino acids are not controlled at low levels in the Low 4 AA condition. Correspondingly, significantly lower concentrations of isovalerate were only seen in the Low 8 AA condition. The levels isovalerate were higher in control HIPDOG conditions and the Low 4 AA condition (FIG. 15B). Formate levels were similar across the all conditions on day 7 of the culture; however, on a per cell basis the amount of formate produced is lower in Low 8 AA condition compared to HIPDOG conditions. The other two inhibitors profiled, 3-(4-hydroxyphenyl)lactate and indole-3-lactate, are byproducts of the amino acids phenylalanine and tryptophan, which are controlled at lower levels in both Low 8 AA and Low 4 AA conditions. Significantly lower concentrations of these two inhibitors were observed in both Low 8 AA and Low 4 AA conditions compared the HIDPOG conditions at day 7 (FIGS. 15A and 16).

Figures 10A, 10B:
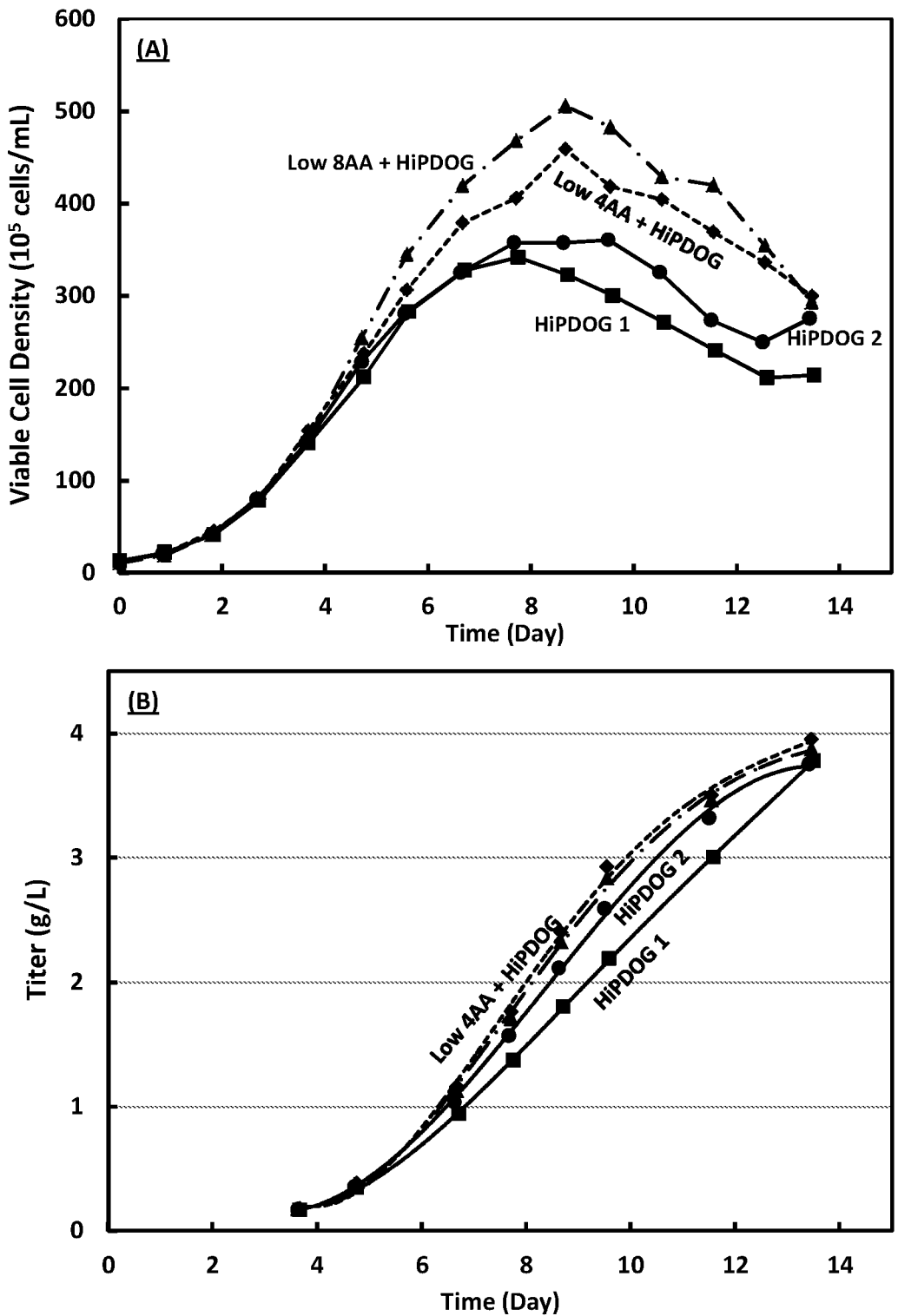
FIG. 10A shows the viable cell densities of GS-CHO cells during a cell culture process using different conditions disclosed in Example 5 (HiPDOG1 (closed squares), HiPDOG2 (closed circles), Low 4AA+HiPDOG (closed diamonds), Low 8AA+HiPDOG (closed triangles)).
FIG. 10B shows the culture titer (IgG) at different days in a cell culture process using GS-CHO cells and different cell culture conditions disclosed in Example 5 ((HiPDOG1 (closed squares), HiPDOG2 (closed circles), Low 4AA+HipDOG (closed diamonds), Low 8AA+HipDOG (closed triangles)).
Figures 11A, 11B:
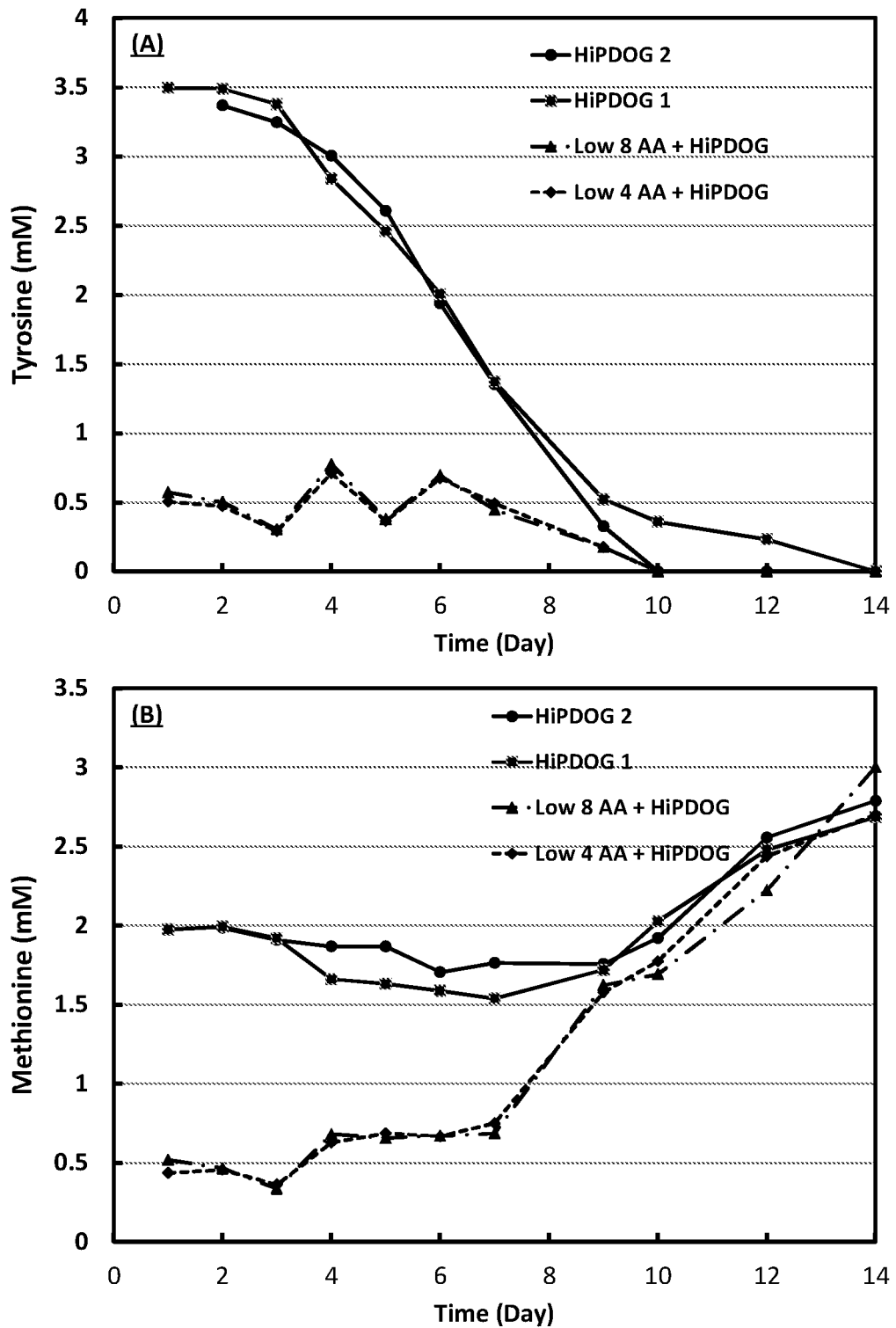
FIGS. 11, 12, 13 and 14 show the concentrations of tyrosine (FIG. 11A), methionine (FIG. 11B), phenylalanine (FIG. 12A), tryptophan (FIG. 12B), leucine (FIG. 13A), threonine (FIG. 13B), glycine (FIG. 14A) and serine (FIG. 14B) during the cell culture of GS-CHO cells using conditions disclosed in Example 5 ((HiPDOG1 (closed squares), (HiPDOG2 (closed circles), Low 4AA+HipDOG (closed diamonds), Low 8AA+HipDOG (closed triangles)).
Figures 12A, 12B:
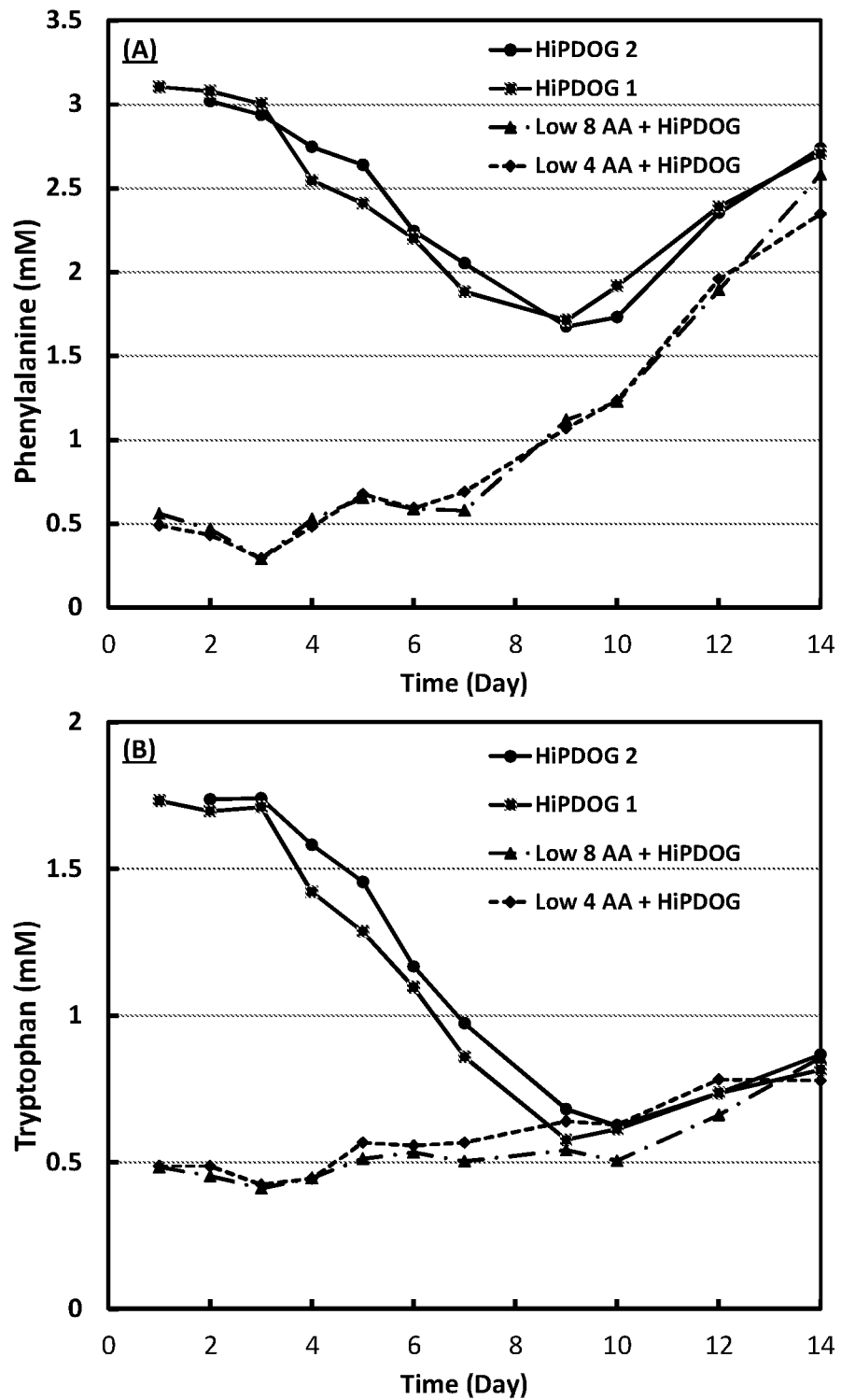
Figures 13A, 13B:
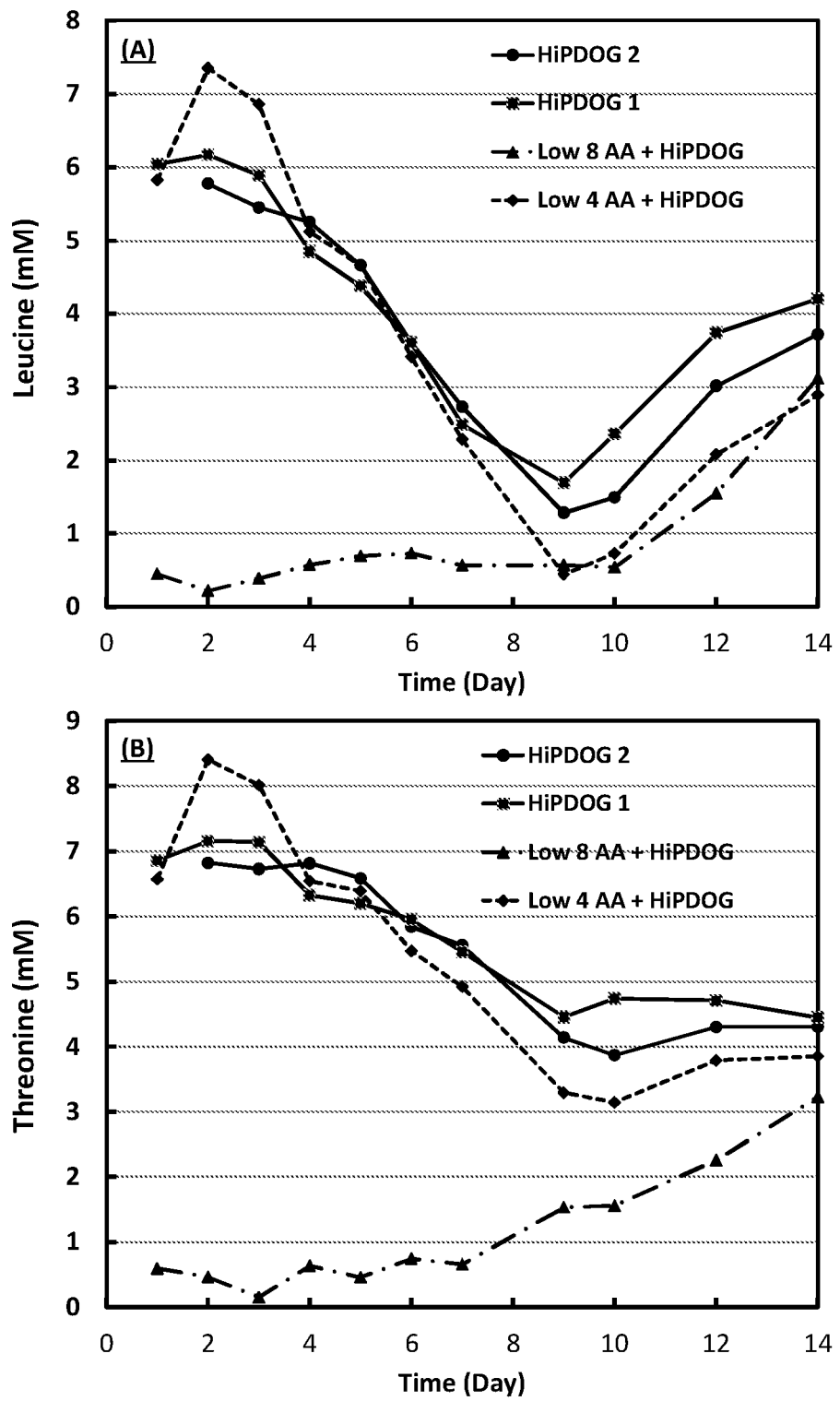
Figures 14A, 14B:
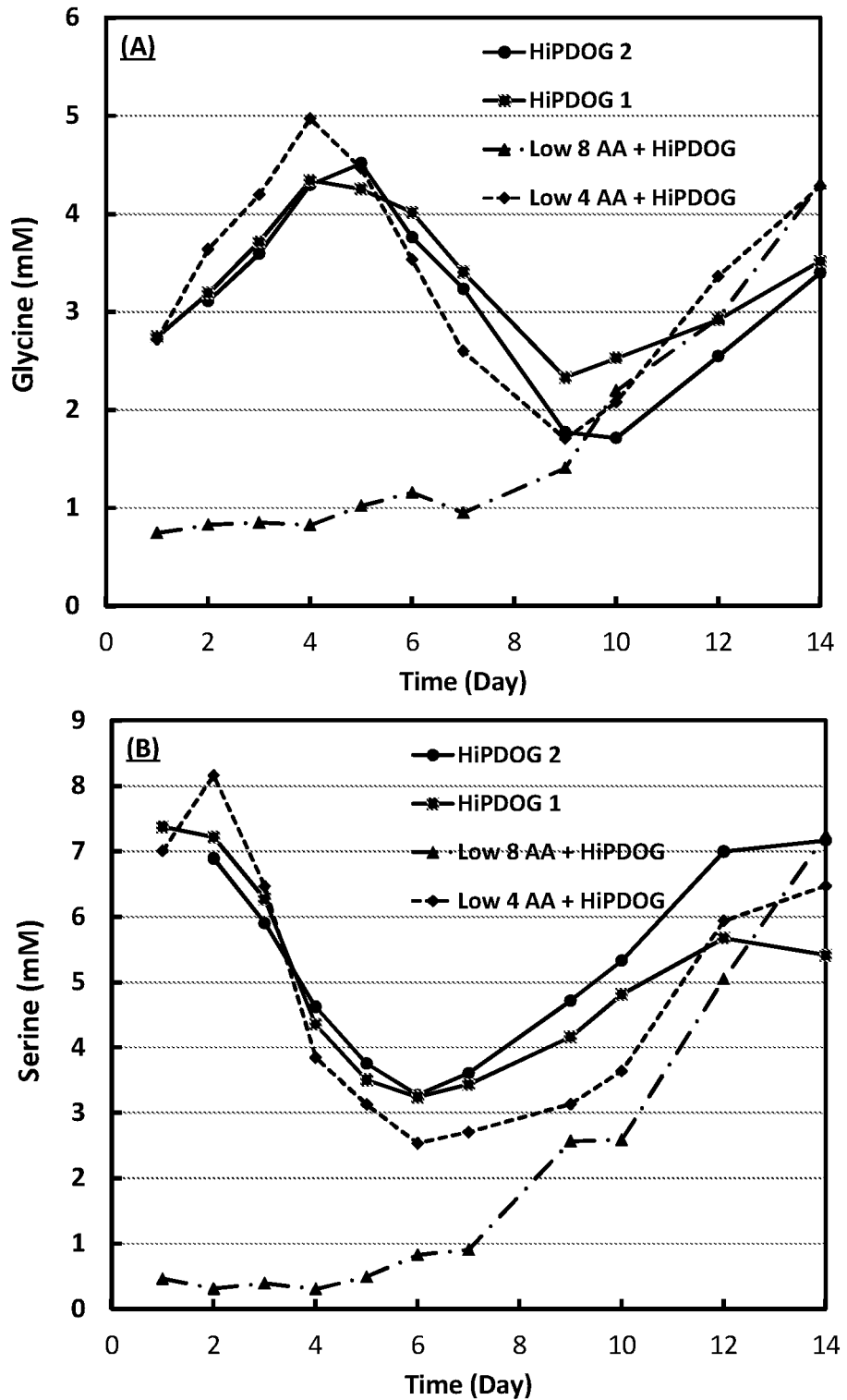

The cells in Low 8 AA and Low 4 AA conditions grew better than the control conditions (HIPDOG1 and HIPDOG 2) peaking at cell densities $50 \times 10^6$ cells/mL and $45 \times 10^6$ cells/mL, respectively, on day 9 whereas the cell densities in control HIPDOG conditions peaked around $32 \times 10^6$ cells/mL (FIG. 10A). Such an increase in the cell growth observed in the late stages of the low amino acid conditions can be explained as an outcome of the reduced inhibitor accumulations in the culture (FIGS. 15 and 16). In addition, the low amino conditions had higher titer compared to the control HIPDOG conditions until day 9, which then tapered off to match the titer levels of HIPDOG conditions by the end of the culture (FIG. 10B). The post day 9 reduction in the protein production in the low amino acid conditions was attributed to the near exhaustion of tyrosine levels in the cultures post day 9 (FIG. 11A).

Figures 17A, 17B:
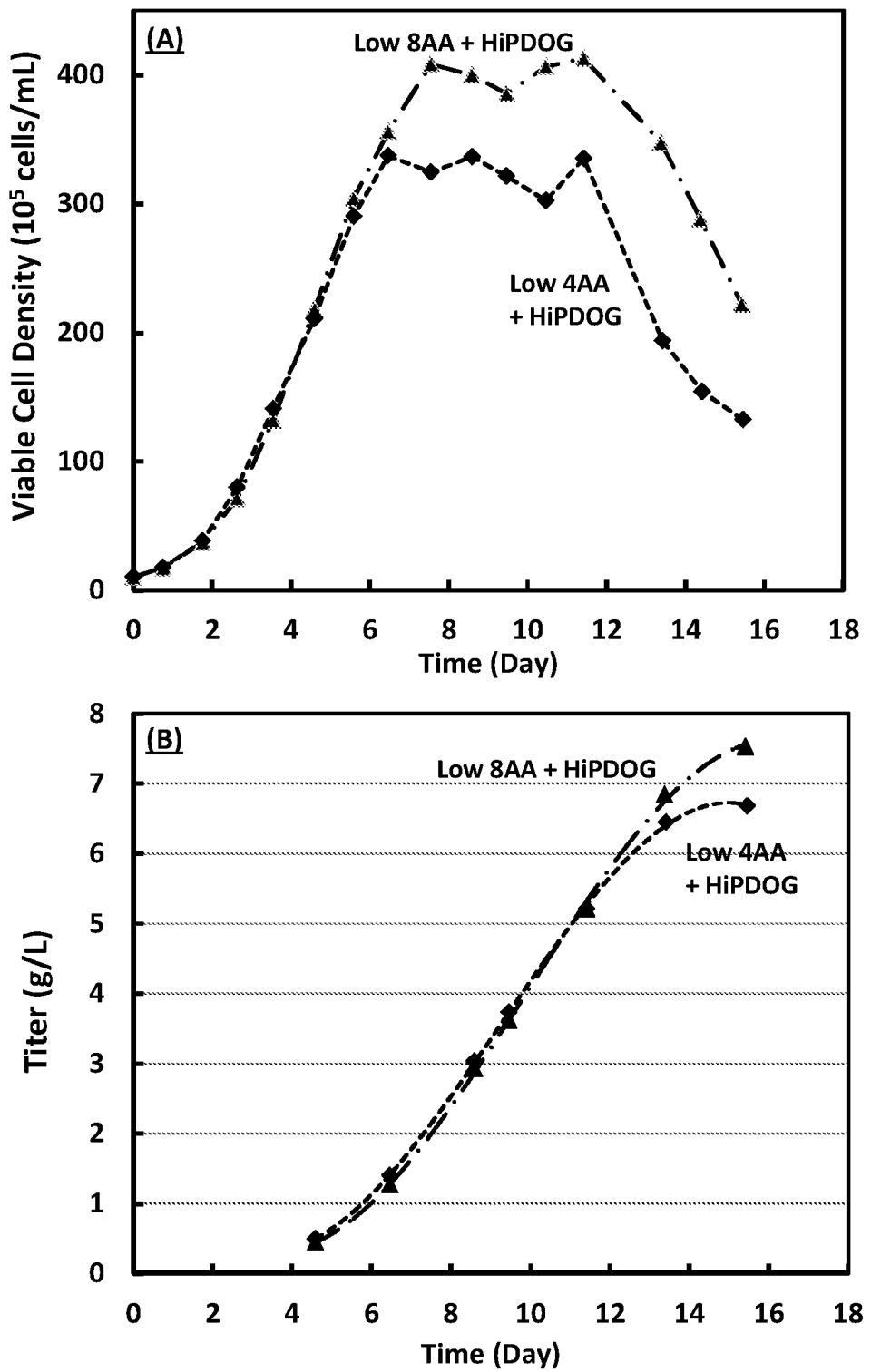
FIG. 17 shows the viable cell densities of GS-CHO cells and culture titer (IgG) during a cell culture process using conditions disclosed in Example 5 ((Low 4AA+HiPDOG (closed diamonds), Low 8AA+HipDOG (closed triangles)).

The second experiment was performed to verify and reproduce the increased positive effect of limiting leucine, serine, glycine and threonine in Low 8 AA condition when compared to Low 4 AA condition (FIG. 17). Only two conditions were tested in this experiment including the Low 8 AA and Low 4 AA condition using the cell line A. The eight amino acids or the four amino acids were controlled between 0.5 mM and 1 mM until day 7 of the culture. Amino acid data is not shown for this experiment but is similar to the amino acid profiles observed for the two conditions in above experiment (FIGS. 11-14) except for tyrosine which was not exhausted in this experiment. The cells grew better in the Low 8 AA condition peaking at $42 \times 10^6$ cells/mL on day 9 whereas the cell densities in Low 4 AA condition peaked around $33 \times 10^6$ cells/mL (FIG. 17). Such an increased cell density also translated into higher levels of harvest titer in the Low 8 AA conditions when compared to Low 4 AA condition.

Example 6: Demonstrating (i) the Reduction in the Accumulation of the Newly Identified Inhibitors Through the Limitation of Amino Acids and (ii) the Positive Effect of Such Limitation of Inhibitory Metabolites on Growth of a Different GS-CHO Cell Line (Cell Line B) in Fed-Batch Cultures Goal:

This experiment was performed to demonstrate that the growth beneficial effects of limiting the levels of certain amino acids on the growth of cells were not specific to one cell line (cell line A) but are more general and can be applied to other cell lines. Two nutrient limitations experiments were performed as part of this example using a different CHO cell line (cell line B) producing a different recombinant antibody. The goal of these experiments was to show that in fed-batch cultures, the control of amino acids at lower levels results in reduced inhibitor accumulations and such low accumulations of inhibitors can explain the increased viable cell densities and protein titers that were seen in the low amino acid fed-batch cultures.

Materials and Methods:

Cells and Bioreactor Setup

A new GS-CHO cell line (cell line B) expressing a different recombinant antibody was used in this example. Two experiments were performed to understand the effect of simultaneously limiting either four or eight amino acids. In first experiment, two conditions were tested: A) HIPDOG fed-batch culture with low levels of eight amino acids including tyrosine, methionine, phenylalanine, tryptophan, leucine, serine, glycine and threonine (Low 8 AA+HIPDOG condition) and B) HIPDOG fed-batch culture with normal amino acids concentrations (HIPDOG condition). In the second experiment, two conditions were tested: A) HIPDOG fed-batch culture with low levels of four amino acids including tyrosine, methionine, phenylalanine and tryptophan (Low 4 AA+HIPDOG condition) and B) HIPDOG fed-batch culture with normal amino acids concentrations (HIPDOG condition). First experiment was run for 12 days whereas the second experiment was only run till day 8 of the culture.

Exponentially growing cells from seed cultures were inoculated at $1 \times 10^6$ cells/mL into each production bioreactor. For all the conditions, HIPDOG strategy was in operation between day 2 and day 7 of the culture. In the low amino acid conditions, the concentrations of above mentioned four or eight amino acids were maintained between 0.5 mM and 1 mM for first seven days of the culture after which they were adjusted to the levels closer to the respective amino acids in the control HIPDOG condition. Post day 7, both the conditions were treated similarly. Viable cell, ammonia and amino acid concentrations were measured on daily basis throughout the culture. For all the conditions, the inoculum viable cell density targeted ($1 \times 10^6$ cells/mL), and the culture volume (1 L) and the process parameters including the temperature (36.5 C), pH (6.9-7.2) and the agitation rate (259 rpm) were identical. The base medium used in the HIPDOG condition was Medium A and that used in Low AA conditions was the modified version of Medium A with low concentrations of either four amino acids (tyrosine, tryptophan, phenylalanine and methionine at approximately 0.6 mM) or eight amino acids (tyrosine, tryptophan, phenylalanine, methionine, leucine, serine, threonine and glycine at approximately 0.6 mM). The feed medium used for all the conditions was Medium B. Amino acid concentrations were measured every day using UPLC based amino acid method as described in Example 4. In the low amino acid conditions, based on the level of amino acids at a given sampling point and the feeding schedule to be followed, concentrated solutions of the amino acids were supplemented to the conditions such that the concentration for the four amino acids or the eight amino acids in corresponding conditions are between 0.5 mM-1 mM at the next sampling time point. Spent medium samples from various conditions across both the experiments of this Example were analyzed to quantitate the levels of the newly identified inhibitors using the NMR technology, as described in the Materials and Methods section of Example 1.

Figures 18A, 18B:
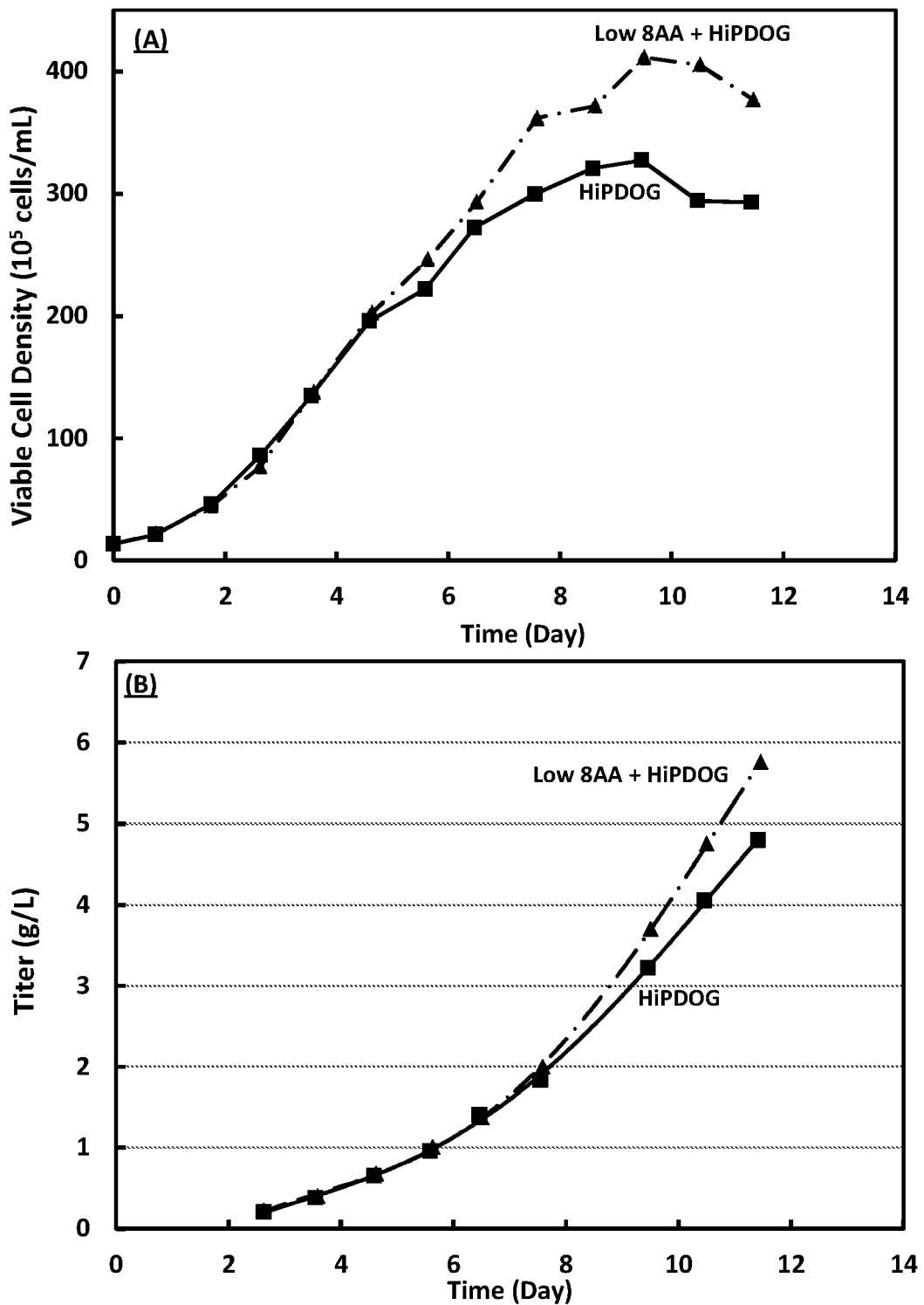
FIGS. 18A and 18B show the viable cell densities of GS-CHO cells and culture titer (IgG) during a cell culture process using conditions disclosed in Example 6 ((HiPDOG (closed squares), Low 8AA+HipDOG (closed triangles)).
Figures 19A, 19B:
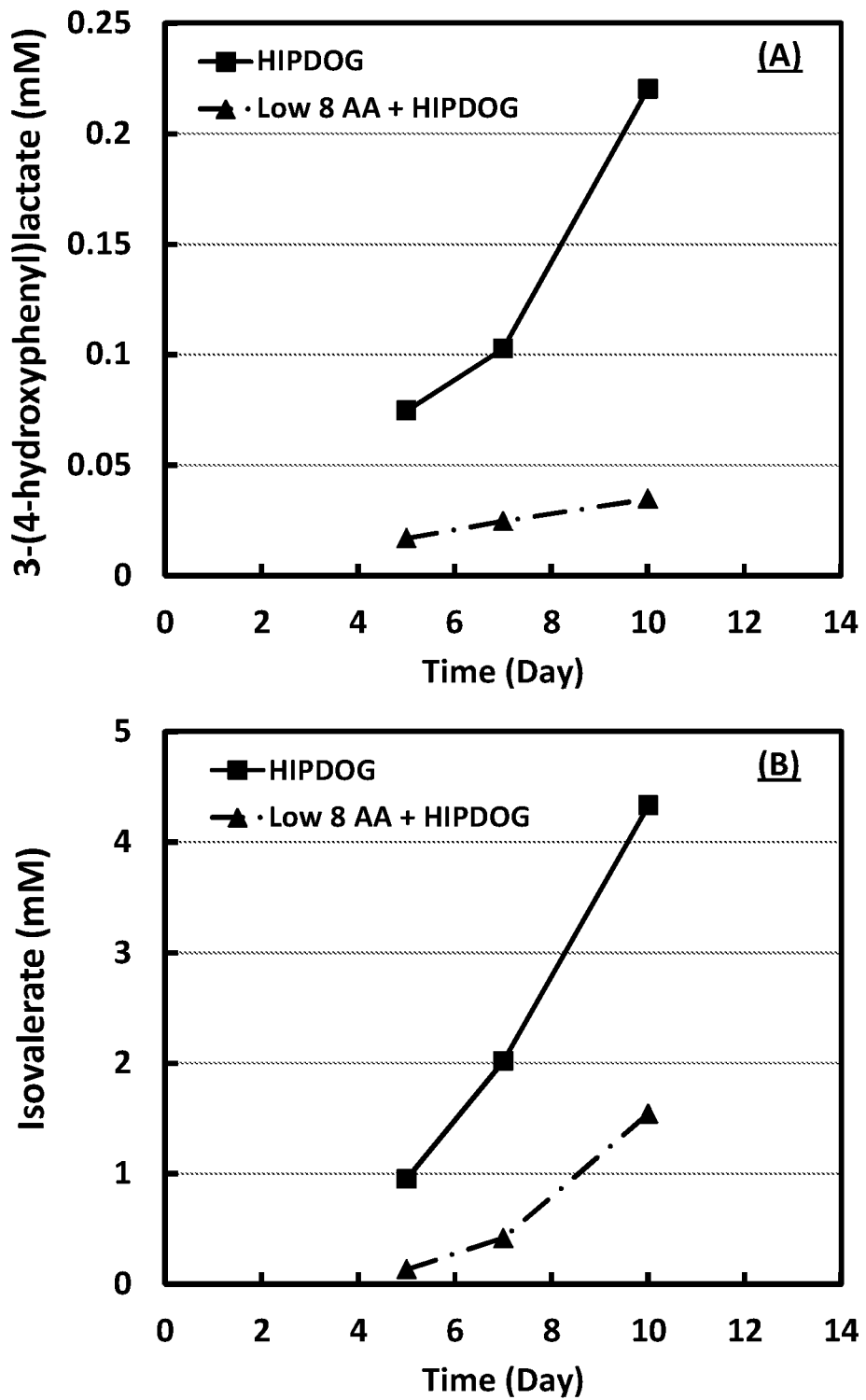
FIGS. 19 and 20 show the concentration of 3-(4-hydroxyphenyl)lactate (FIG. 19A), isovalerate (FIG. 19B) and indole-3-lactate (FIG. 20) at day 5, day 7 and day 10 of the cell culture of GS-CHO cells using conditions disclosed in Example 6 ((HiPDOG (closed squares), Low 8AA+HipDOG (closed triangles)).
Figure 20:
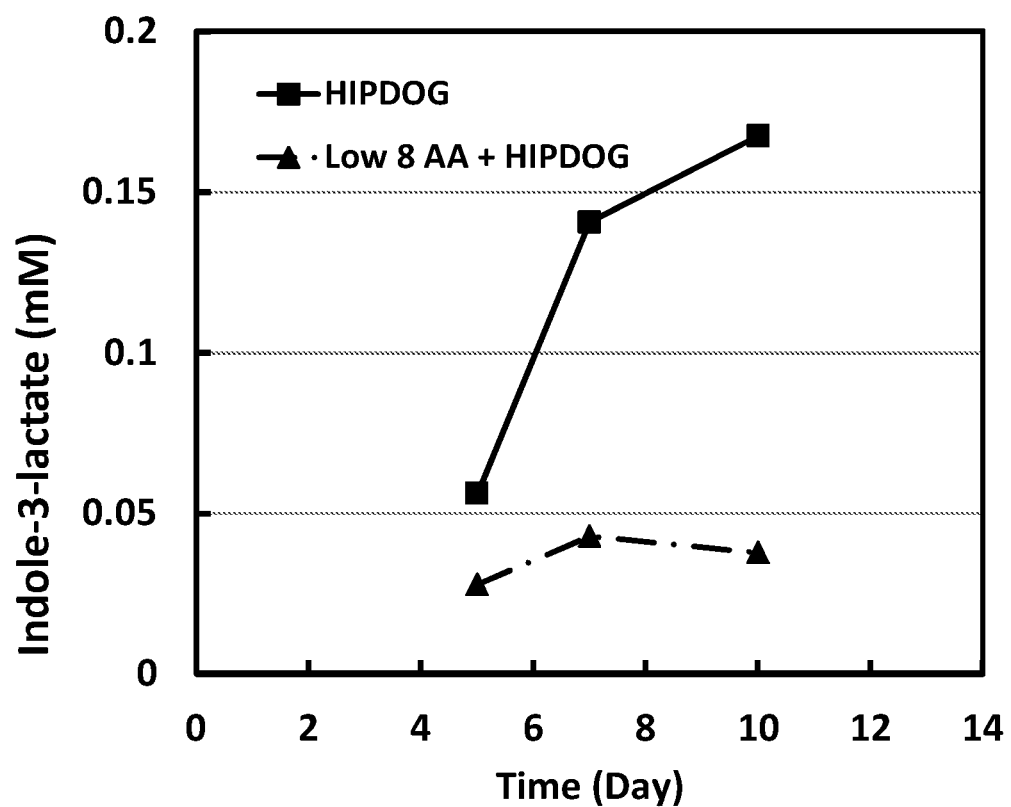

Results:

In the first experiment, the concentrations of the eight amino acids were successfully maintained between 0.5 mM-1 mM in Low 8 AA condition until day 7 of the fed-batch cultures. Amino acid culture profiles are not shown for this experiment but are similar to those observed for the similar conditions in Experiment 1 of Example 5 (FIGS. 11-14) except for tyrosine which was not exhausted in this experiment. Such limitation of amino acid levels in the Low 8 AA condition resulted in lower levels of biosynthesis and reduced accumulation of the newly identified metabolites. Four of the nine inhibitors listed in Table 3 were profiled (FIG. 19 and FIG. 20). In Low 8 AA condition, significantly lower accumulations of isovalerate, 3-(4-hydroxyphenyl)lactate and indole-3-lactate were observed compared to control HIPDOG condition. Formate levels were observed to be higher in Low 8 AA condition on day 10 of the culture, however, on a per cell basis, the amount of formate produced was similar in the Low 8 AA condition compared to the HIPDOG condition. The cells in Low 8 AA conditions grew better than the control condition (HIPDOG) peaking at cell densities of $40 \times 10^6$ cells/mL on day 9 whereas the cell densities in control HiPDOG conditions peaked around $32 \times 10^6$ cells/mL (FIG. 18A). Further, the increased growth observed in Low 8 AA condition translated into higher titer levels compared to the control HIPDOG condition (FIG. 18B). Such an increase in the cell growth and productivity observed in the low amino acid condition can be explained as an outcome of the reduced inhibitor biosynthesis and accumulation (FIGS. 19 and 20).

Figures 21A, 21B:
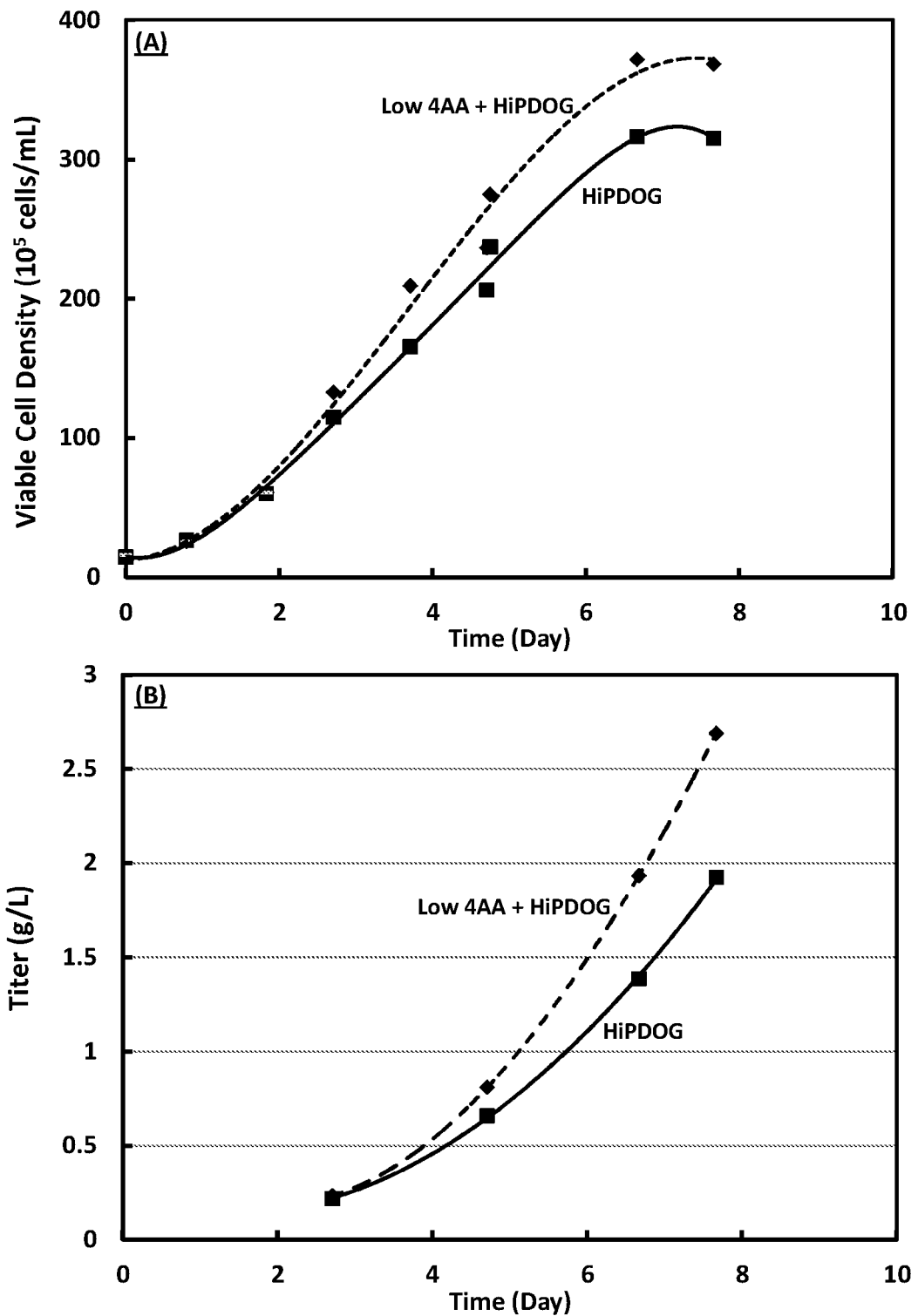
FIGS. 21A and 21B show the viable cell densities of GS-CHO cells and culture titer (IgG) during a cell culture process using different conditions disclosed in Example 6 ((HiPDOG (closed squares), Low 4AA+HipDOG (closed diamonds)).
Figures 22A, 22B:
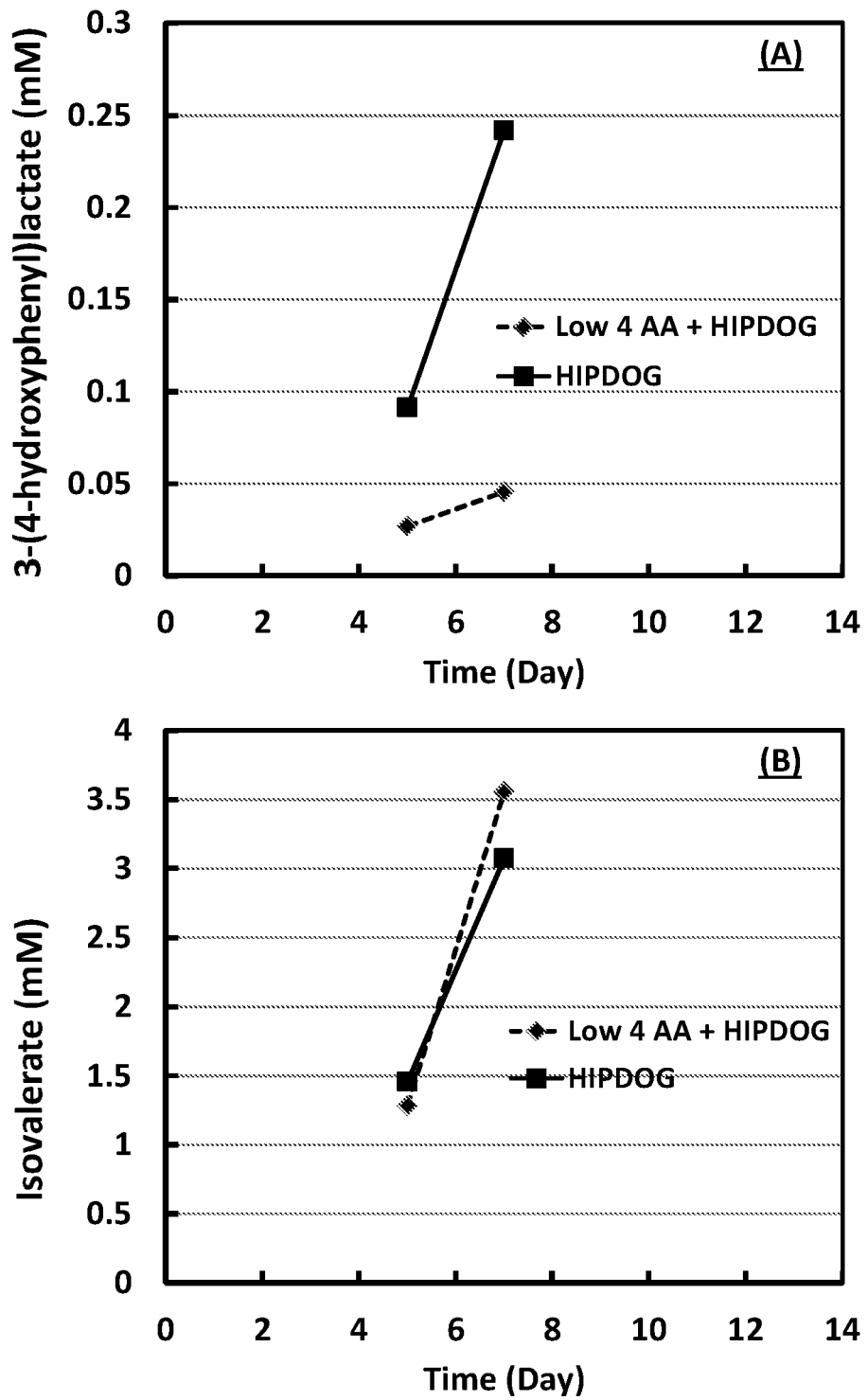
FIGS. 22 and 23 show the concentration of 3-(4-hydroxyphenyl)lactate (FIG. 22A), isovalerate (FIG. 22B) and indole-3-lactate (FIG. 23) at day 5 and day 7 of the cell culture of GS-CHO cells using conditions disclosed in Example 6 ((HiPDOG (closed squares), Low 4AA+HipDOG (closed diamonds)).
Figure 23:
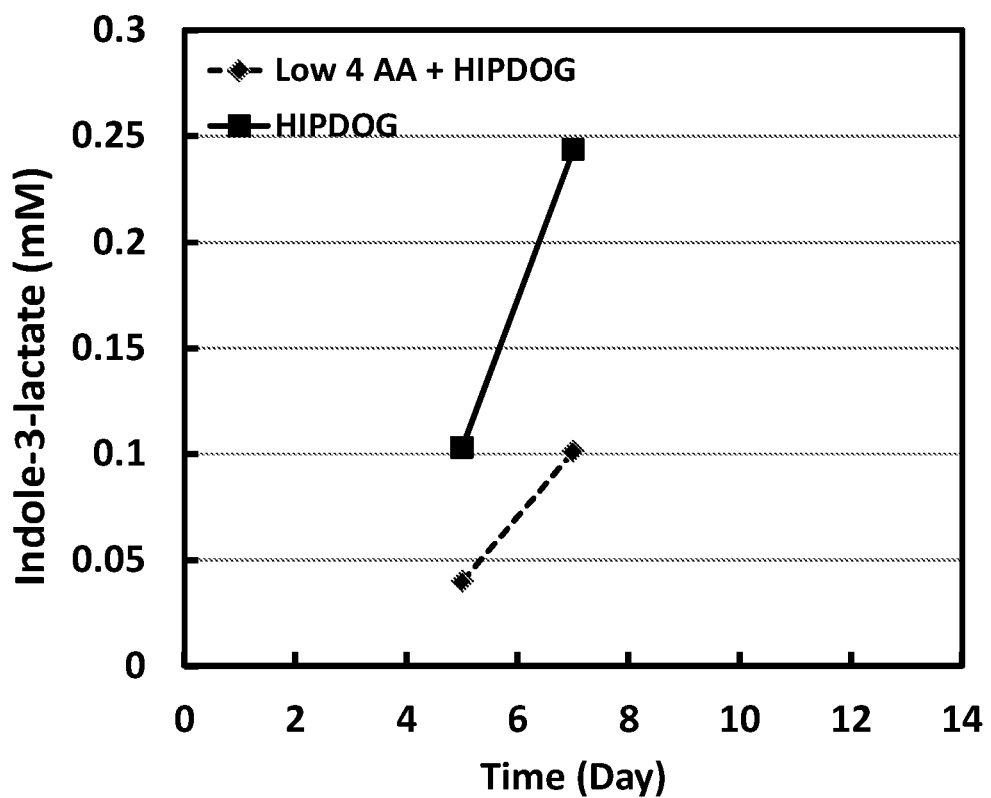

The second experiment was performed to investigate the effect of controlling the levels of four amino acids (tyrosine, phenylalanine, tryptophan and methionine) between 0.5 mM-1 mM (Low 4 AA+HIPDOG) on growth and productivity of cell line B, when compared to control HIPDOG condition (FIGS. 21-23). Amino acid culture profiles are not shown for this experiment but are similar to those observed for the similar conditions in Experiment 1 of Example 5 (FIGS. 11-14) except for tyrosine which was not exhausted in this experiment. Such limitation of amino acid levels in the Low 4 AA condition resulted in lower levels of biosynthesis and reduced accumulation of the newly identified metabolites. Four of the nine inhibitors listed in Table 3 were profiled (FIG. 22 and FIG. 23). Except isovalerate, the levels of the other three inhibitors were lower in the Low 4 AA condition compared to HIPDOG condition. Leucine not being one of the amino acids which is controlled at low levels in the Low 4 AA condition, its metabolic intermediate isovalerate accumulates in Low 4 AA condition to levels similar to those seen the control HIPDOG condition. The cells in Low 4 AA conditions grew better peaking at cell densities $37 \times 10^6$ cells/mL on day 9 of the culture whereas the cell densities in control HIPDOG condition peaked around $32 \times 10^6$ cells/mL (FIG. 21A). Further, the increased growth observed in Low 4 AA condition translated into higher titer levels compared to the control HIPDOG condition (FIG. 21B). Such an increase in the cell growth and productivity observed in the low amino acid condition can be explained as an outcome of the reduced inhibitor biosynthesis and accumulation (FIGS. 22 and 23).

Example 7: Use of RAMAN Spectroscopy for Online Measurement of the Four (Phenylalanine, Tyrosine, Tryptophan and Methionine) or Eight Amino Acids (Phenylalanine, Tyrosine, Tryptophan, Methionine, Leucine, Serine, Glycine, and Threonine) and Newly Identified Inhibitors Raman spectroscopy is based on the inelastic scattering of monochromatic light (photons) by a molecule. The technology uses the frequency shift in the light, due to a change in energy of the photon when it is absorbed and reemitted by the molecule, to determine the characteristics of the molecule. This technology has been successfully used in microbial and mammalian cell culture bioreactors with success to measure the levels of various process parameters. Raman spectroscopy has also been used to determine the concentrations of glucose, lactate, ammonia, glutamine and glutamate in CHO cell cultures.

The Raman spectra for all the amino acids have been previously reported in the literature. Raman spectra for the newly identified inhibitory metabolites is characterized using a solution of the purified metabolites. An empirical model is built by employing a training set of spectral data generated using known concentrations of each of the four or eight amino acids or the newly identified inhibitors, individually. The sample matrix (background) used for of the preparation of calibration samples (used as the training set) is a mix of spent media samples taken from different time points of different cell culture processes. The model developed using such a training set is more general and can be applied to any other cell culture process. This model is used to measure the concentration of the four or eight amino acids or the metabolites (inhibitors) in the culture (online) and accordingly control the levels of amino acids through feedback control feeding strategies.

Example 8: Suppression of Inhibitor Formation Through Control of Amino Acids at Low Levels in Fed-Batch Cultures by Using Online Measurement of Inhibitor Concentration A fed-batch process is designed to reduce the formation of the inhibitors through control of four (phenylalanine, tyrosine, tryptophan and methionine) or eight amino acids (phenylalanine, tyrosine, tryptophan, methionine, leucine, serine, glycine, and threonine) at low levels, for example between 0.2-1 mM in the cell culture medium. Such a control of the inhibitor production is attained by a feeding strategy that operates as a feed-back loop based on the online measurement of the inhibitors themselves. Such online measurements are in the form of RAMAN spectroscopy or through use of HPLC/UPLC based technology with an auto-sampler that draws sample from reactor and transfers it to the equipment in a programmed manner. As and when the concentration of the inhibitors rises above a specified level (example: 0.2 mM), the amount of phenylalanine, tyrosine, tryptophan, methionine, leucine, serine, glycine, and threonine fed to the cells is decreased until the concentration of inhibitors falls below a predefined level (for example 0.1 mM).

Example 9: Suppression of Inhibitor Formation Through Online or Offline Measurement and Control of Amino Acids at Low Levels in Fed-Batch Cultures A fed-batch process is designed to reduce the formation of the inhibitors through control of the four (phenylalanine, tyrosine, tryptophan and methionine) or eight amino acids (phenylalanine, tyrosine, tryptophan, methionine, leucine, serine, glycine, and threonine) at low levels (0.2-1 mM). Such a control of inhibitor formation is attained by a feeding strategy that operates as a feed-back loop based on the online measurement of the amino acids. Such online measurements is in the form of RAMAN spectroscopy or through use of HPLC/UPLC based technology with an auto-sampler that draws sample from reactor and transfers it to the equipment in a programmed manner. As and when the concentration of the amino acids falls below a specified level (example: 0.5 mM), estimated amounts of feed medium (similar to Medium B) is added to the culture so as to maintain the concentrations of the four or eight amino acids.

Alternatively, the samples are taken on a once per day basis and amino acid concentrations are measured offline using a UPLC/HPLC method. The amino acid concentrations obtained are used to calculate the cell specific uptake rates of the four (phenylalanine, tyrosine, tryptophan and methionine) or eight amino acids (phenylalanine, tyrosine, tryptophan, methionine, leucine, serine, glycine, and threonine) between previous two sampling time points. Assuming that the cells maintain the same specific rate of amino acid consumption until the next sampling time point, the amount of feed medium (example: Medium B) to be added till the next sampling point is determined and provided to the cells, such that the concentrations of the amino acids are always within the desired range (0.2 mM-1 mM).

Example 10: Suppression of Inhibitor Formation Through Programmed Feeding so as to Keep the Amino Acids at Low Levels in Fed-Batch Cultures The formation of the newly identified inhibitors in culture is kept low by maintaining the concentration of the four (phenylalanine, tyrosine, tryptophan and methionine) or eight amino acids (phenylalanine, tyrosine, tryptophan, methionine, leucine, serine, glycine, and threonine) at low levels in culture (0.2-1 mM). This is attained by designing a programmed feeding strategy (using modified Medium B) such that the concentrations of the amino acids, at any given time point in the culture are always within the desired range (0.2 mM-1 mM). Such a feeding strategy is contrived by assessing the specific consumption rates of amino acids at different time points along the culture and modifying the concentration in the feed medium (Medium B) such that with the above defined feeding strategy/schedule, sufficient amounts of amino acids are provided to the culture to maintain the amino acids concentrations within the desired range (0.2-1 mM).

Example 11: Experiment to Determine the Gene Targets for Metabolic Engineering for Suppressing the Biosynthesis of the Inhibitors Related to Phenylalanine/Tyrosine Pathway Goal:

The experiment was performed to determine the cause for production of inhibitor molecules including phenyllactate, 4-hydroxyphenylpyruvate and 3-(4-hydroxyphenyl)lactate. Gene expression of all the enzymes in the phenylalanine/tyrosine pathway was probed using Real Time Quantitative Polymerase Chain Reaction (RT-qPCR) assay. Based on the gene expression and the biochemistry of the phenylalanine/tyrosine catabolic pathway, gene targets for metabolic engineering of the CHO cell line A that suppress the biosynthesis of above mentioned inhibitors, was identified.

Materials and Methods:

Gene Expression Analysis

RT-qPCR assay was used to assess relative gene expression levels of enzymes in the leucine and phenylalanine/tyrosine metabolic pathways. RT qPCR measures transcript abundance, and hence, gene expression by amplifying a target cDNA sequence using PCR in combination with a detection reagent (i.e. SYBR Green). SYBR green is a molecule that fluoresces when bound to double stranded DNA and the fluorescence can be measured in real time during the RT qPCR assay. The amount of fluorescence is directly proportional to the amount of double stranded PCR product (also called amplicon) in the reaction. Relative gene expression levels are determined by measuring the number of PCR cycles required for SYBR green fluorescence to surpass the background fluorescence and increase logarithmically. This cycle number is commonly referred to as the $C_T$ (Threshold Cycle). A transcript in high abundance would have a lower $C_T$ value as it would require fewer PCR cycles for the fluorescence to surpass the background fluorescence where, conversely, a transcript in lower abundance would have a higher $C_T$ value as it would require more PCR cycles for the fluorescence to surpass the background level.

The RT qPCR assay was performed using an Applied Biosystems 7500 Real Time PCR system (Applied Biosystems) and the PowerUP SYBR Green Master Mix reagent (Life Technologies). The PCR primers were designed using the Primer3 algorithm based on genomic DNA sequences contained in the Chinese Hamster Ovary (CHO) genome browser (chogenome.org). RNA was prepared from CHO cell line A using the Qiagen RNeasy Kit (Qiagen) which was in turn used as template for oligo dT primed cDNA synthesis using the SuperScript III First-Strand Synthesis System for RT-PCR (Life Technologies). The $C_T$ values of the targeted metabolic genes were tabulated and compared to the $C_T$ value of a well characterized housekeeping gene, Beta Actin. The difference between the $C_T$ of the target gene and the $C_T$ of Beta Actin was reported as the $\Delta C_T$. High $\Delta C_T$ value indicates low gene expression level.

Results:

The $C_T$ and $\Delta C_T$ values for the genes in the phenylalanine/tyrosine pathway is shown in FIG. 24. The gene expression data from the phenylalanine/tyrosine pathway indicates that CHO cell line A has low expression of the PAH, HPD and HGD genes. As the expressed protein (or enzyme) levels correlate to the transcript levels, low levels of PAH enzyme can result in the phenylalanine being converted to phenylpyruvate and subsequently to phenyllactate by catalytic action of GOT1/GOT2 and MIF enzymes, both of which are expressed at high levels in CHO cell line A. Similarly, due to low levels of HPD and HGD enzymes in CHO cell line, tyrosine is channeled towards production of 4-hydroxyphenylpyruvate and 3-(4-hydroxyphenyl)lactate by catalytic action of GOT1/GOT2 and MIF enzymes. Reducing the channeling of the phenylalaine and tyrosine flux towards inhibitor production requires the down-regulation of the expression of GOT1/GOT2 and MIF genes. However, GOT1/GOT2 and MIF are critical for other physiologically important metabolic functions. Therefore, down-regulation of the two enzymes wouldn't potentially yield a viable cell line. An alternative way to reduce inhibitor biosynthesis is through overexpression of the PAH, HPD and HGD genes which would then channel the flux away from inhibitor production and towards production of Krebs cycle metabolites (which are used for energy synthesis in mitochondria). Hence the metabolic targets for phenylalaine/tyrosine pathway are PAH, HPD and HGD genes.

Example 12: Experiment to Determine the Gene Targets for Metabolic Engineering for Suppressing the Biosynthesis of the Inhibitors Related to Leucine Pathway Goal:

The experiment was performed to determine the cause for the biosynthesis and accumulation of isovaleric acid, which is a byproduct of leucine metabolism and accumulates to very high levels in fed-batch cultures of CHO cells. Gene expression of all the enzymes in the leucine pathway was probed using Real Time Quantitative Polymerase Chain Reaction (RT-qPCR) assay. Further, production of isovaleric acid in human disease conditions such as isovaleric academia has been reported to be due to 'loss of function' mutations in enzymes down stream of isovaryl-CoA, an intermediate in leucine catabolism pathway. These enzymes include Ivd, Mccc1, and Mccc2, which can harbor loss of activity mutations though expressed at high levels. Therefore, the mutation status of these enzymes in CHO cell line A was investigated. Based on the gene expression analysis and mutation analysis of the above mentioned enzymes in leucine catabolism pathway, gene targets for metabolic engineering of the CHO cell line A that will suppress the biosynthesis of isovaleric acid were identified.

Materials and Methods:

Mutation Analysis

Genomic DNA sequence flanking the translated regions of Ivd, Mccc1 and Mccc2 (at the 5' and 3' ends) was identified and used as a template for PCR primer design using the Primer3 algorithm. RNA was prepared from CHO cell line A using the Qiagen RNeasy Kit (Qiagen) which was in turn used as a template for oligo dT primed cDNA synthesis using the SuperScript III First-Strand Synthesis System for RT-PCR (Life Technologies). An extension temperature and magnesium concentration optimized PCR reaction was performed using Pfu Turbo HotStart 2X Master Mix (Agilent). The samples were purified using the QIAquick PCR Purification Kit (Qiagen) and sent for sequence analysis at Wyzerbio (Cambridge, Mass.).

Figure 25:
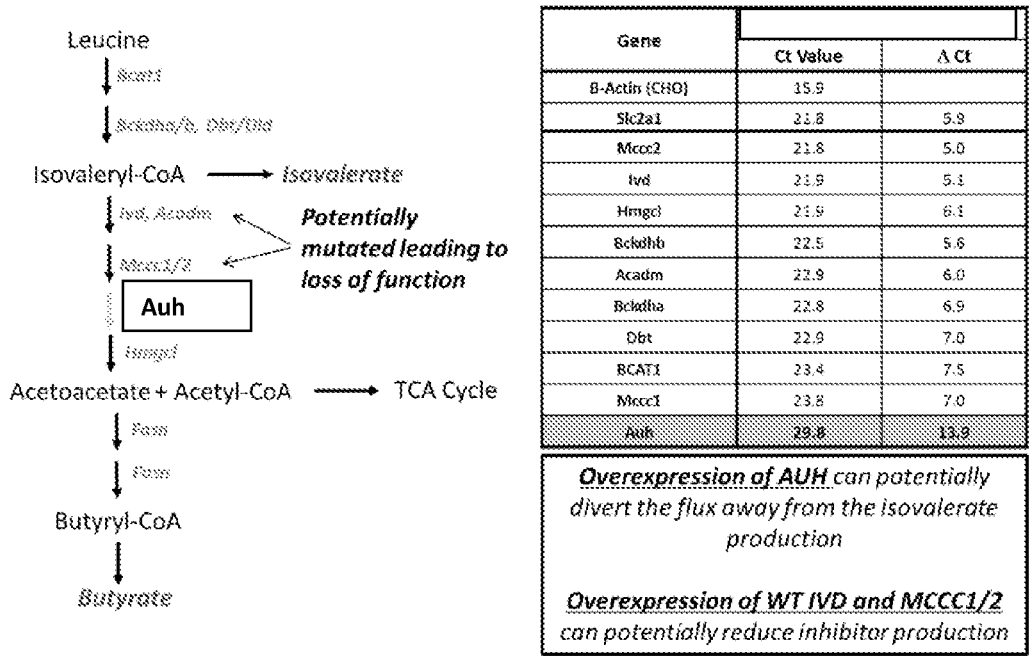

Results:

The $C_T$ and $\Delta C_T$ values for the genes in the leucine pathway are shown in FIG. 25. The gene expression data from the phenylalanine/tyrosine pathway indicates that CHO cell line A has lower levels of AUH enzyme relative to the other enzymes in the pathway. However, this data doesn't strongly explain the high levels of isovaleric acid production as reported in the earlier experiments, as the enzyme is further downstream of the node which branches out towards isovaleric acid production (FIG. 25). Therefore, loss of function (enzyme activity) of IVD, MCCC1 and/or MCCC2 could give a better rationale for isovaleric acid production. DNA sequencing results reveal the mutation status and the likely level of function of the encoded enzyme. Should an enzyme activity altering mutation in the IVD, MCCC1, and MCCC2 genes be found, a metabolic engineering approach that entails overexpression of the corresponding wild type (non-mutated) gene will be undertaken, in this case the gene origin would be from a CHO cell line although other origin sources for wild type genes are obtainable and could be used such as human, rat, mouse. In addition to this, AUH gene will also be overexpressed in the same CHO cell line A.

A correlation of the gene acronyms with the full nomenclature for the genes discussed herein is provide below in Table 5.

TABLE 5

Genes of the phenylanaline/tyrosine and leucine pathways as also illustrated in FIGS. 24 and 25

| Symbol | Name |
|---|---|
| Pah | phenylalanine hydroxylase |
| Mif | macrophage migration inhibitory factor |
| Got1 | glutamic-oxaloacetic transaminase 1, soluble |
| Got2 | glutamatic-oxaloacetic transaminase 2, mitochondrial |
| Hpd | 4-hydroxyphenylpyruvic acid dioxygenase |
| Hgd | homogentisate 1,2-dioxygenase |
| Gstz1 | glutathione transferase zeta 1 (maleylacetoacetate isomerase) |
| Fah | fumarylacetoacetate hydrolase |
| Bcat1 | branched chain aminotransferase 1, cytosolic |
| Bckdha | branched chain ketoacid dehydrogenase E1, alpha polypeptide |
| Bckdhb | branched chain ketoacid dehydrogenase E1, beta polypeptide |
| Dbt | dihydrolipoamide branched chain transacylase E2 |
| Dld | dihydrolipoamide dehydrogenase |
| Ivd | isovaleryl coenzyme A dehydrogenase |
| Acadm | acyl-Coenzyme A dehydrogenase, medium chain |
| Mccc1 | methylcrotonoyl-Coenzyme A carboxylase 1 (alpha) |
| Mccc2 | methylcrotonoyl-Coenzyme A carboxylase 2 (beta) |
| Auh | AU RNA binding protein/enoyl-coenzyme A hydratase |
| Hmgcl | 3-hydroxy-3-methylglutaryl-Coenzyme A lyase |
| Fasn | fatty acid synthase |
| Nup62-il4i1 | nucleoporin 62-interleukin 4 induced 1/L-amino acid oxidase |

Example 13: Experiment to Ectopically Express in CHO Cell Line A, the Mouse Genes of HPD, HGD, PAH, AUH and Wild Type Form of any Other Gene Target Determined in Example 12 Through Mutation Analysis Goal:

Based on low gene expression levels relative to Beta Actin as determined by the RT qPCR assay, four targets were selected for overexpression in CHO cells: Auh (leucine metabolic pathway) and HPD, HGD, and PAH (phenylalanine/tyrosine metabolic pathway). In addition, based on the loss of activity mutation status of IVD, MCCC1 and MCCC2, the wild type gene of the mutated enzymes will be selected for overexpression in CHO cells. Generally where genes are found to be mutated or inactive the strategy is to overexpress the wild type genes. The goal is to clone mouse mRNA sequences of these genes into a commercially available mammalian expression vector and transfect CHO cell line A with these expression vectors. The resulting cell lines have a high level of expression of the mouse AUH, HPD, HGD, or PAH gene and by extension, a higher level of AUH, HPD, HGD, or PAH enzyme activity. Increased activity in these key enzymes will likely improve metabolic flux and reduce the cellular concentration of certain known inhibitory substances.

Materials and Methods:

Overexpression cassettes were constructed using mouse cDNA sequences from the MGC collection of AUH, HPD, HGD, and/or PAH genes. The sequences were provided as *E. coli* glycerol stocks containing shuttle vectors with cDNAs of the target genes (GE Dharmacon). PCR primers were designed using the Primer3 algorithm to amplify the coding regions of the cDNAs in reactions with a proof-reading polymerase called Pfu Turbo HotStart 2X Master Mix (Agilent). The PCR products were directionally cloned into the pcDNA Gateway Direction TOPO Expression vector (Invitrogen). The vector contains a viral promoter sequence (Human cytomegalovirus immediate early promoter), a directional TOPO cloning site, an epitope tag (V5) for detection using anti-V5 antibodies, a polyadenylation sequence (Herpes Simplex Virus thymidine kinase), and antibiotic resistance gene (Blasticidin). The vectors are sequence confirmed by WyzerBio and transfected into CHO Cell Line A for over expression using the GenePulser XCell eletroporator (BioRad) and recovered in the presence of blasticidin for selective pressure. The engineered CHO cells are assessed for expression of the trans-gene by RT qPCR, western hybridization, and enzyme assay. Upon selection with medium containing blasticidin the cells are cryopreserved for later experimentation in bioreactors.

The transfected cell lines are therefore engineered to express mouse AUH, HPD, HGD, and/or PAH genes at high levels and by extension, have increased AUH, HPD, HGD, or PAH enzymatic activity. Analysis by RT qPCR, Western hybridization, and enzyme assay is performed to reveal increase in the total Auh, Hpd, Hgd, or Pah gene expression and enzyme activity (both endogenous and transgenic) in the newly created transgenic cell lines.

Example 14: Experiment to Probe the Suppression of Inhibitor Formation in Genetically Engineered Cell Lines that Expresses the Target Genes Determined in Examples 11 and 12

Goal:

As part of this experiment, the phenotype of the clones (and pools) overexpressing the target genes was investigated. Phenotype determination mainly entails the peak cell densities and productivity of these clones in HIPDOG fed-batch culture and/or the level of inhibitor molecule accumulation in the culture.

Materials and Methods:
Cells and Bioreactor Setup

CHO cells used in the experiment are the engineered form of CHO cell line A obtained from overexpression of the target genes PAH, HPD, HGD, AUH and wild type form of any other gene target determined in Example 11 and 12 by mutation analysis. Two conditions are be tested as part of this experiment: A) HIPDOG fed-batch culture using the CHO cells expression all the target genes and B) HIPDOG fed-batch culture with CHO cells expressing GFP protein. Details on the use HIPDOG technology are described in the material and methods section of Example 1. Exponentially growing cells from seed culture are inoculated at $1 \times 10^6$ cells/mL into production bioreactors that employs HiPDOG process. For both the conditions, HiPDOG control is in operation between day 2 and day 7 of the culture. Viable cell density, lactate, ammonia and amino acid concentrations are measured on daily basis until day 12 (amino acids measured only for first seven days). For both conditions, the inoculum viable cell density targeted ($1 \times 10^6$ cells/mL), and the culture volume (1 L) and the process parameters including the temperature (36.5 C), pH (6.9-7.2) and the agitation rate (267 rpm) were identical. For both conditions, the base media used will be Medium A and the feed medium is Medium B. Supernatant samples from various conditions across both the experiments are analyzed for the levels of the newly identified inhibitors using the NMR technology described in the Materials and Methods section of Example 1. Amino acid concentrations are measured for samples using UPLC based amino acid method which is described in detail below.

Amino Acid Analysis

10 μL of either a standard amino acid mix solution or a spent media sample (10 times diluted sample) is mixed with 70 μL of AccQ•Tag Ultra borate buffer (Waters UPLC AAA H-Class Applications Kit [176002983]), and 20 μL of AccQ•Tag reagent previously dissolved in 1.0 mL of AccQ•Tag Ultra reagent diluent was added. The reaction is allowed to proceed for 10 min at 55° C. Liquid chromatographic analysis was performed on a Waters Acquity UPLC system, equipped with a binary solvent manager, an autosampler, a column heater and a PDA detector. The separation column is a Waters AccQ•Tag Ultra column (2.1 mm i.d.×100 mm, 1.7 μm particles). The column heater is set at 55° C., and the mobile phase flow rate was maintained at 0.7 mL/min. Eluent A is 10% AccQ•Tag Ultra concentrate solvent A, and eluent B is 100% AccQ•Tag Ultra solvent B. The nonlinear separation gradient is 0-0.54 min (99.9% A), 5.74 min (90.0% A), 7.74 min (78.8% A), 8.04-8.64 min (40.4% A), 8.73-10 min (99.9% A). One microliter of sample is injected for analysis. The PDA detector is set at 260 nm. The previously determined elution times for the amino acids are used to identify the specific amino acid peaks on the chromatogram for each sample. The amino acid concentrations are estimated using the area under the peak and the calibration curve generated using the standard solution (Amino Acids Standard H, Thermo Scientific, PI-20088).

Results:

Cells expressing the target gene channel lower carbon (phenylalanie, tyrosine and leucine) towards biosynthesis of inhibitor resulting in lower accumulations of the compounds in the culture medium. However, the cells expressing the GFP molecule (negative control) channel more carbon towards inhibitor production leading to higher accumulations of the same in the culture media. Such differences in the levels of inhibitor production and accumulation results in growth differences leading to higher peak cell densities in the cells expressing the target gene set compared to cell expressing GFP. Such increase in the total cells also leads to higher over yield of the recombinant protein produced by the cells.

Example 15: Experiment to Determine the Gene Targets for Metabolic Engineering for Suppressing the Biosynthesis of the Inhibitors Related to Phenylalanine/Tyrosine Pathway Goal This experiment was performed to determine the cause for production of inhibitor molecules including phenyllactate, 4-hydroxyphenylpyruvate and 3-(4-hydroxyphenyl)lactate. Gene expression of all the enzymes in the phenylalanine/tyrosine pathway was probed using Real Time Quantitative Polymerase Chain Reaction (RT-qPCR) assay. Based on the gene expression and the biochemistry of the phenylalanine/tyrosine catabolic pathway, gene targets for metabolic engineering of the CHO cells (CHO cell line A, CHO cell line B and parental cell line) that suppress the biosynthesis of above mentioned inhibitors, were identified.

Materials and Methods
Gene Expression Analysis

RT-qPCR assay was used to assess relative gene expression levels of enzymes in the phenylalanine/tyrosine metabolic pathways. RT qPCR measures transcript abundance, and hence, gene expression by amplifying a target cDNA sequence using PCR in combination with a detection reagent (i.e. SYBR Green). SYBR green is a molecule that fluoresces when bound to double stranded DNA and the fluorescence can be measured in real time during the RT qPCR assay. The amount of fluorescence is directly proportional to the amount of double stranded PCR product (also called amplicon) in the reaction. Relative gene expression levels are determined by measuring the number of PCR cycles required for SYBR green fluorescence to surpass the background fluorescence and increase logarithmically. This cycle number is commonly referred to as the $C_T$ (Threshold Cycle). A transcript in high abundance would have a lower $C_T$ value as it would require fewer PCR cycles for the fluorescence to surpass the background fluorescence where, conversely, a transcript in lower abundance would have a higher $C_T$ value as it would require more PCR cycles for the fluorescence to surpass the background level.

The RT qPCR assay was performed using an Applied Biosystems 7500 Real Time PCR system (Applied Biosystems) and the PowerUP SYBR Green Master Mix reagent (Life Technologies). The PCR primers were designed using the Primer3 algorithm based on genomic DNA sequences contained in the Chinese Hamster Ovary (CHO) genome browser. RNA was prepared from CHO cell line A using the Qiagen RNeasy Kit (Qiagen) which was in turn used as template for oligo dT primed cDNA synthesis using the SuperScript III First-Strand Synthesis System for RT-PCR (Life Technologies). The $C_T$ values of the targeted metabolic genes were tabulated and compared to the $C_T$ value of a well characterized housekeeping gene, beta-Actin (B-Actin). The difference between the $C_T$ of the target gene and the $C_T$ of B-Actin was reported as the $\Delta CT$. High $\Delta C_T$ value indicates low gene expression level.

Results

The $C_T$ and $\Delta C_T$ values for the genes in the phenylalanine/tyrosine pathway for CHO cell line A and parental cell line are shown in FIG. 26. CHO cell line B has similar level of gene expression as CHO cell line A (data not shown). The gene expression data from the phenylalanine/tyrosine pathway indicates that CHO cell line A and parental cell line have low expression of the PAH, HPD and HGD genes. The protein (or enzyme) levels correlate to the transcript levels, low levels of PAH enzyme can result in the phenylalanine being converted to phenylpyruvate and subsequently to phenyllactate by catalytic action of GOT1/GOT2 and MIF enzymes (or non-specific enzymatic reactions), both of which are expressed at high levels in CHO cell line A and parental cell line. Similarly, due to low levels of HPD and HGD enzymes in CHO cell line A and parental cell line, tyrosine is channeled towards production of 4-hydroxyphenylpyruvate and 3-(4-hydroxyphenyl)lactate by catalytic action of GOT1/GOT2 and MIF enzymes (or non-specific enzymatic reactions). One way to reduce the channeling of the phenylalanine and tyrosine flux towards inhibitor production would be to down-regulate the expression of GOT1/GOT2 and MIF genes. However, GOT1/GOT2 and MIF are critical for other physiologically important metabolic functions. Therefore, down-regulation or knocking-out of these two enzymes wouldn't potentially yield a viable cell line. An alternative way to reduce inhibitor biosynthesis is through overexpression of the PAH, HPD and HGD genes which would then channel the flux away from inhibitor production and towards production of Krebs cycle metabolites (which are used for energy synthesis in mitochondria). Hence, the metabolic targets chosen for phenylalanine/tyrosine pathway are PAH, HPD and HGD genes.

Figures 27A, 27B:
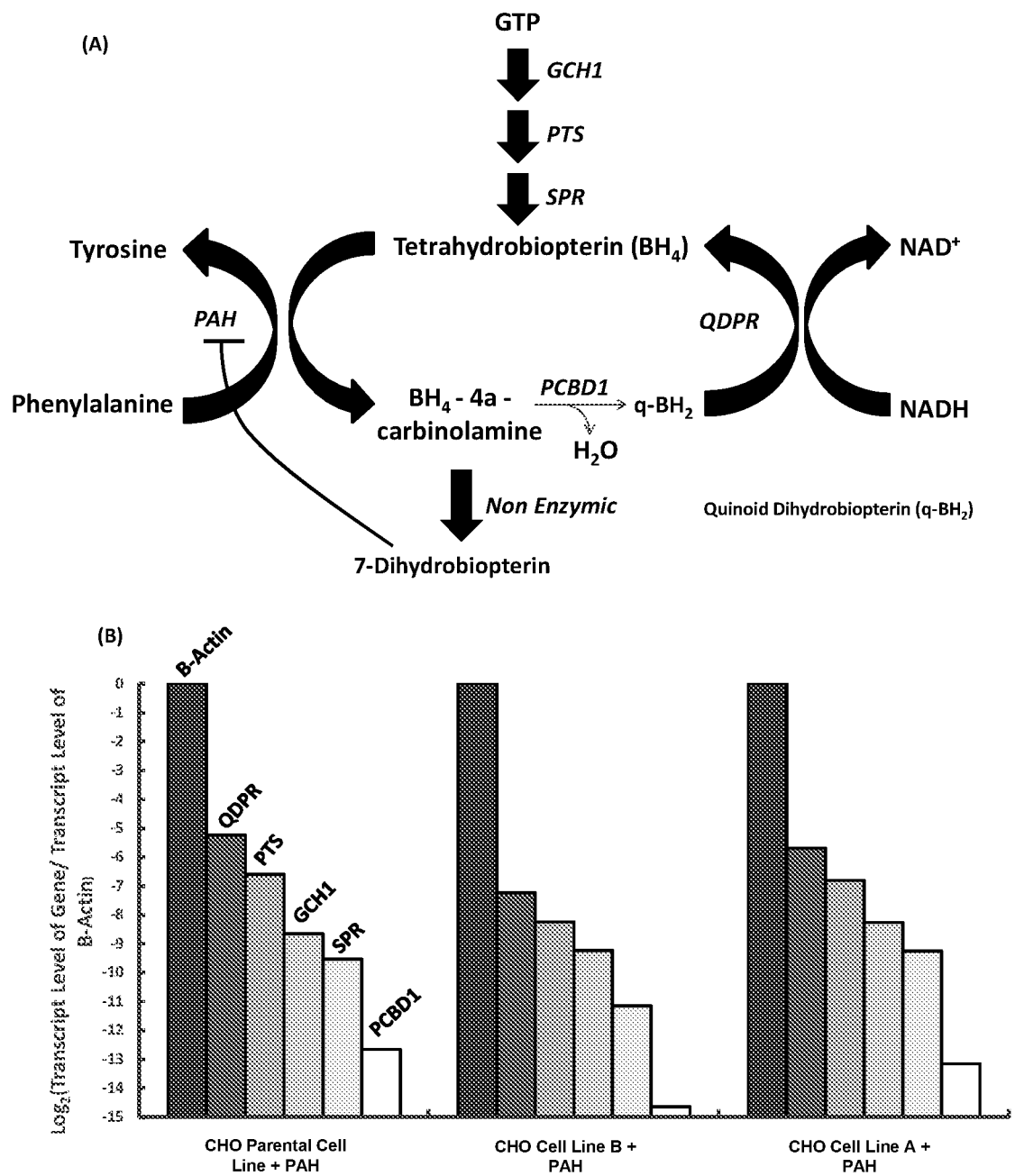
FIG. 27: Gene expression analysis of tetrahydrobiopterin ($BH_4$) biosynthesis and regeneration pathway genes using RT-qPCR assay. (A) Schematic of tetrahydrobiopterin ($BH_4$) biosynthesis and regeneration pathway. GTP is the carbon source for biosynthesis of $BH_4$ catalyzed by three enzymes GCH1, PTS and SPR. $BH_4$ regeneration pathway consists of two enzymes, PCBD1 and QDPR, that together regenerate $BH_4$ from $BH_4$-4a-carbinolamine, which is the product of the reaction catalyzed by PAH. (B) Expression levels of tetrahydrobiopterin ($BH_4$) biosynthesis and regeneration pathway genes in cell pools of CHO cell line A, CHO cell line B or CHO parental cell line overexpressing mouse PAH. Data is plotted as log of the ration of gene of interest transcript level to B-Actin transcript level. Higher value indicates higher expression of gene.

In addition to the three targets in the phenylalanine/tyrosine pathway identified by RT qPCR (PAH, HGD, and HPD), a fourth target was examined. The PAH enzyme requires a cofactor called tetrahydrobiopterin ($BH_4$) for its catalytic activity. Mammalian cells synthesize $BH_4$ using GTP as a substrate (FIG. 27A). The enzymes involved in the biosynthesis of $BH_4$ include GCH1, PTS and SPR. Further, $BH_4$ is converted to $BH_4$-4a-carbinolamine during the reaction catalyzed by PAH activity, which is recycled back to $BH_4$ by the activity of PCBD1 and QDPR enzymes. The expression of genes encoding for the biosynthesis and the recycling enzymes was likewise assayed by RT qPCR in CHO cells (cells used for gene expression analysis were those which went through first round of transfection with mouse PAH gene; see Example 16) (FIG. 27B). Based on the high $C_T$ value, high $\Delta C_T$, and hence, low level of gene expression, the PCBD1 gene was also selected for overexpression. All other genes in the $BH_4$ pathway were expressed at reasonable levels (see FIG. 27B).

Example 16: Experiment to Overexpress PAH, HPD, HGD and PCBD1 in CHO Cell Lines

Goal

Based on low gene expression levels relative to B-Actin, as determined by the RT qPCR assay, four targets were selected for overexpression in CHO cells: HPD, HGD, PAH and PCBD1. The main goal of this experiment was to clone mRNA sequences of these genes into a commercially available mammalian expression vectors and transfect CHO parental cell line, CHO cell line A and CHO cell line B with the expression vectors. The resulting cells were expected to have a high level of expression of HPD, HGD, PAH and PCBD1 genes and by extension, a higher level of HPD, HGD, PAH and PCBD1 enzyme activity. Increased activity of these key enzymes have improved metabolic flux and reduced the cellular concentration of the identified inhibitory substances.

Materials and Methods

Figures 28A, 28B:
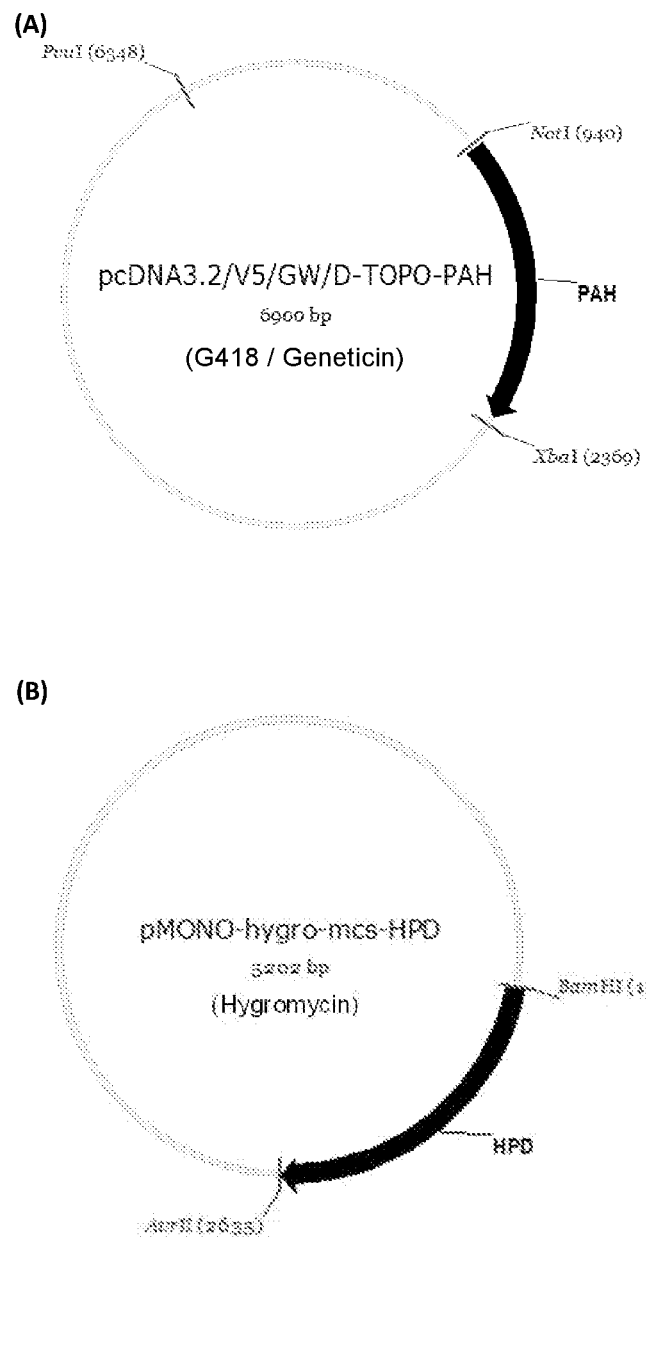
FIG. 28: Plasmids used for generating transgenic CHO cell lines expressing mouse PAH, HPD, HGD, and PCBD1. (A) Plasmid map of the expression vector for mouse PAH. (B) Plasmid map of the expression vector for mouse HPD. (C) Plasmid map of the expression vector for mouse HGD. (D) Plasmid map of the expression vector for mouse PCBD1.
Figure 28C:
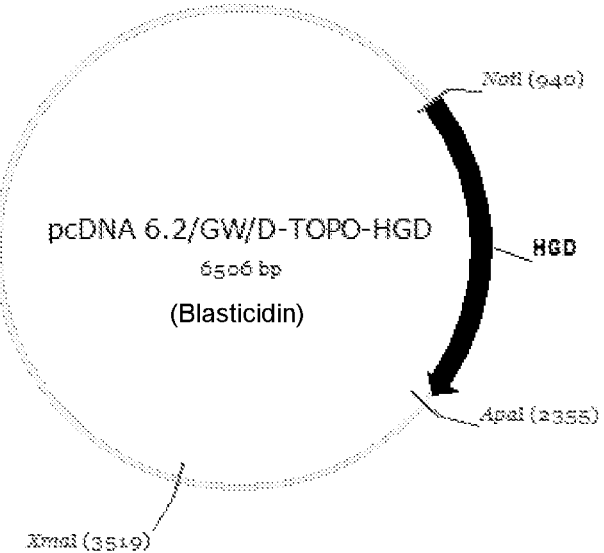
Figure 28D:
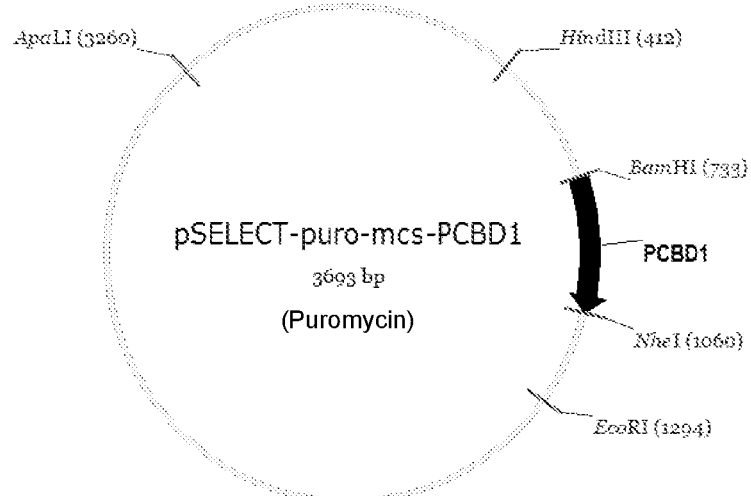

Expression vectors for HPD, HGD, PAH and PCBD1 genes were constructed using mouse cDNA sequences from the MGC collection (FIG. 28). The sequences were provided by GE Dharmacon as *E. coli* glycerol stocks containing shuttle vectors with cDNAs of the target genes. PCR primers were designed using the Primer3 algorithm to amplify the coding regions of the cDNAs in reactions with a proof-reading polymerase called Pfu Turbo HotStart 2X Master Mix (Agilent). The PCR products were cloned into commercially available constitutive expression vectors with different antibiotic resistance genes to allow for individual selection of the expression plasmids shown in Table 6. In addition, control vectors were also provided by the vendor to serve as a negative control (transfection control). The vectors were sequence confirmed by WyzerBiosciences (Cambridge, Mass.). The expression and control plasmids were transfected into CHO parental cells, CHO cell line A and CHO cell line B using the GenePulser XCell eletroporator (BioRad) and recovered in the presence of antibiotics for selective pressure. A stepwise approach was taken whereby the cells were first transfected with the PAH expression vector and recovered. The PAH expressing cell pools were then transfected with HPD and HGD together, and the resultant cell pool was transfected with PCBD1 until the final product, a 4-times transfected cell line, was achieved. Upon selection with medium containing antibiotics, the cell pools were cryopreserved for later experimentation in bioreactors. FIG. 28 shows the expressed mouse genes, the expression vectors created in Pfizer's laboratories and the antibiotic selection gene. CHO cell line A was only transfected with PAH and was not taken through subsequent set of transfections. Table 6 shows a summary of the plasm ids used for each gene expressed, including the commercial expression vector used, the antibiotic used as selection pressure, and the vendor of the expression vector. Also listed are the null vectors used to generate negative transfection control cell lines.

control (4x-control-tfxn) cell pools, which lacks mouse PAH, HPD, HGD and PCBD1 expression.

Results

The $C_T$ values for mouse PAH, HPD, HGD and PCBD1 genes in 4x-tfxn cell pools and the corresponding negative

TABLE 6

| Gene | Vector For Transfection | Antibiotic Selection | Vendor of Expression Vector |
|---|---|---|---|
| PAH | pcDNA3.2/V5/GW/D-TOPO | G418 (Geneticin) | Invitrogen (Thermo Fisher) |
| HPD | pMONO-hygro-mcs | Hygromycin | Invivogen |
| HGD | pcDNA6.2/V5/GW/D-TOPO | Blasticidin | Invitrogen (Thermo Fisher) |
| PCBD1 | pSELECT-puro-mcs | Puromycin | Invivogen |
| Control for PAH | pcDNA3.2/V5/GW-CAT | G418 (Geneticin) | Invitrogen (Thermo Fisher) |
| Control for HPD | pMONO-hygro-mcs | Hygromycin | Invivogen |
| Control for HGD | PCDNA6.2/V5/GW-CAT | Blasticidin | Invitrogen (Thermo Fisher) |
| Control for PCBD1 | pSELECT-puro-mcs | Puromycin | Invivogen |

Results

Cell pools were generated after transfection with PAH, HPD, HGD, and PCBD1 expression vectors (called 4x-tfxn cell pools) along with the accompanying negative control vectors (either empty vector or vector containing chloramphenicol acetyltransferase (CAT)) (called 4x-control-tfxn cell pools). 4x-tfxn cell pools obtained from transfection were designed to express mouse PAH, HPD, HGD and PCBD1 genes at high levels and have increased PAH, HPD, HGD and PCBD1 enzymatic activity. Analysis by RT qPCR (see Example 17), and western hybridization (data not shown) was used to determine changes in PAH, HPD, HGD and PCBD1 gene expression (both endogenous and transgenic) in the newly created transgenic cell pools.

Example 17: Experiment to Probe the Expression of Mouse Transgenes (PAH, HPD, HGD and PCBD1) in the Cell Pools Generated from the Quadruple Transfections Goal An RT qPCR assay was performed to assess relative gene expression levels of mouse transgenes PAH, HPD, HGD, and PCBD1 in 4x-tfxn cell pools derived from parental cell line or CHO cell line B.

Materials and Methods

The RT qPCR assay was performed using an Applied Biosystems 7500 Real Time PCR system (Applied Biosystems) and the PowerUP SYBR Green Master Mix reagent (Life Technologies). The PCR primers were designed using the Primer3 algorithm based on the mouse cDNA sequences from the MGC collection provided by GE Dharmacon. RNA was prepared from the 4x-tfxn cells pools and 4x-control-tfxn cell pools of CHO cell line B or parental cell line using the Qiagen RNeasy Kit (Qiagen), which was in turn used as template for oligo dT primed cDNA synthesis using the SuperScript III First-Strand Synthesis System for RT-PCR (Life Technologies). The $C_T$ values of the mouse PAH, HPD, HGD, and PCBD1 genes were tabulated and compared to the $C_T$ value of a well characterized housekeeping gene, B-Actin. The delta between the $C_T$ of the target gene and the $C_T$ of B-Actin was reported as the $\Delta C_T$. Successful expression of mouse transgenes PAH, HPD, HGD and PCBD1 genes in 4x-tfxn cell pools was identified by reduced $\Delta C_T$ value (and hence, increased gene expression level) when compared to the $\Delta C_T$ value of the transgenes in the negative control pools (4x-control-tfxn) are shown in Table 7. Lower $\Delta C_T$ values were observed for the mouse transgenes in the 4x-tfxn cell pools of CHO cell line B and parental cell line compared to the corresponding negative control cell pools (4x-control-tfxn). This indicates that the gene expression of the targets was higher in 4x-tfxn pools and therefore promotes the channeling of amino acid flux away from the phenyllactate, 3-(4-hydroxyphenyl)lactate and 4-hydroxyphenyllactate inhibitor biosynthesis pathway (see Example 19). The apparent presence of expression of mouse PAH, HPD, HGD and PCBD1 in 4x-control-tfxn cell pools is due in part to high levels of sequence homology between the transgenic (mouse) and endogenous (hamster) PAH, HPD, HGD and PCBD1 genes. This suggests that the data reflect accurately the total level of PAH, HPD, HGD and PCBD1 gene expression inclusive of both transgenic and endogenous genes.

Table 7 shows the expression levels, as assayed by RT-qPCR, of mouse PAH, HPD, HGD and PCBD1 genes in quadruple transfected (4x-tfxn) or negative quadruple transfection control (4x-control-tfxn) cell pools of CHO parental cell line and CHO cell line B.

TABLE 7

| | Average $\Delta C_t$ Compared to B-Actin (Low $\Delta C_t$ value = High Expression) | | | |
|---|---|---|---|---|
| Gene | CHO Parental Cell Line 4x-control-tfxn | CHO Parental Cell Line 4x-tfxn | CHO Cell Line B 4x-control-tfxn | CHO Cell Line B 4x-tfxn |
| PAH | 11.53 | 8.2 | 11.96 | 7.86 |
| HPD | 18.13 | 5.02 | 18.01 | 3.11 |
| HGD | 20.21 | 16.34 | 19.23 | 15.25 |
| PCBD1 | 12.7 | 6.24 | 14.66 | 3.97 |

Example 18: Probing the Ability of Cell Pools that Express the Four Transfected Mouse Genes Including PAH, HPD, HGD and PCBD1 (4x-Tfxn) to Grow in Tyrosine-Free Medium Goal Expression of PAH and PCBD1 enzyme activity conferred the ability to cells to catalyze the synthesis of tyrosine from phenylalanine and therefore to promote the channeling of amino acid flux away from the phenyllactate, 3-(4- hydroxyphenyl)lactate and 4-hydroxyphenyllactate inhibitor biosynthesis pathway (see Example 19). The goal of this experiment was to test if 4x-tfxn cell pools expressing the four mouse genes including PAH, HPD, HGD and PCBD1, derived from CHO cell line B or parental host cell line, have the ability to proliferate in tyrosine-free medium conditions.
Materials and Methods
Cells, Medium and Experiment Setup 4x-tfxn cell pools or 4x-control-tfxn cell pools of CHO cell line B or parental cell line were spun down and cell pellets were inoculated in Medium D (Medium C without tyrosine, but with supplementation of additional amount (2 mM) of phenylalanine). Medium C is approximately a third in concentration of various amino acids of the levels in Medium A. Medium A is a fortified version of insulin-free Medium 9 as disclosed in U.S. Pat. No. 7,294,484, table 14, with slight differences in concentrations of sodium bicarbonate and potassium chloride, and containing Pluronic F68 instead of polyvinyl alcohol. It was fortified by adding 10% glutamine-free Medium 5 (U.S. Pat. No. 7,294,484, table 7), and by further raising the concentrations of eight amino acids (Glu, Tyr, Gly, Phe, Pro, Thr, Trp and Val). The concentrations of amino acids are listed in the Table 8 below.

TABLE 8

Concentration of Amino Acids in Medium A

| Amino Acids | Concentration in Medium A (mM) |
|---|---|
| alanine | 0.4 |
| arginine | 5.3 |
| asparagine•H2O | 21.1 |
| aspartic acid | 2.3 |
| cysteine•HCl•H2O | 0.4 |
| cystine•2HCl | 1.5 |
| glutamic acid | 0 |
| monosodium glutamate | 2.0 |
| glutamine | 0 |
| glycine | 3.6 |
| histidine•HCl•H2O | 2.7 |
| isoleucine | 5.4 |
| leucine | 9.4 |
| lysine•HCl | 8.9 |
| methionine | 3.1 |
| phenylalanine | 4.5 |
| proline | 9.1 |
| serine | 11.8 |
| threonine | 10.8 |
| tryptophan | 2.3 |
| tyrosine•2Na•2H2O | 5.1 |
| valine | 10.3 |

Figures 29A, 29B:
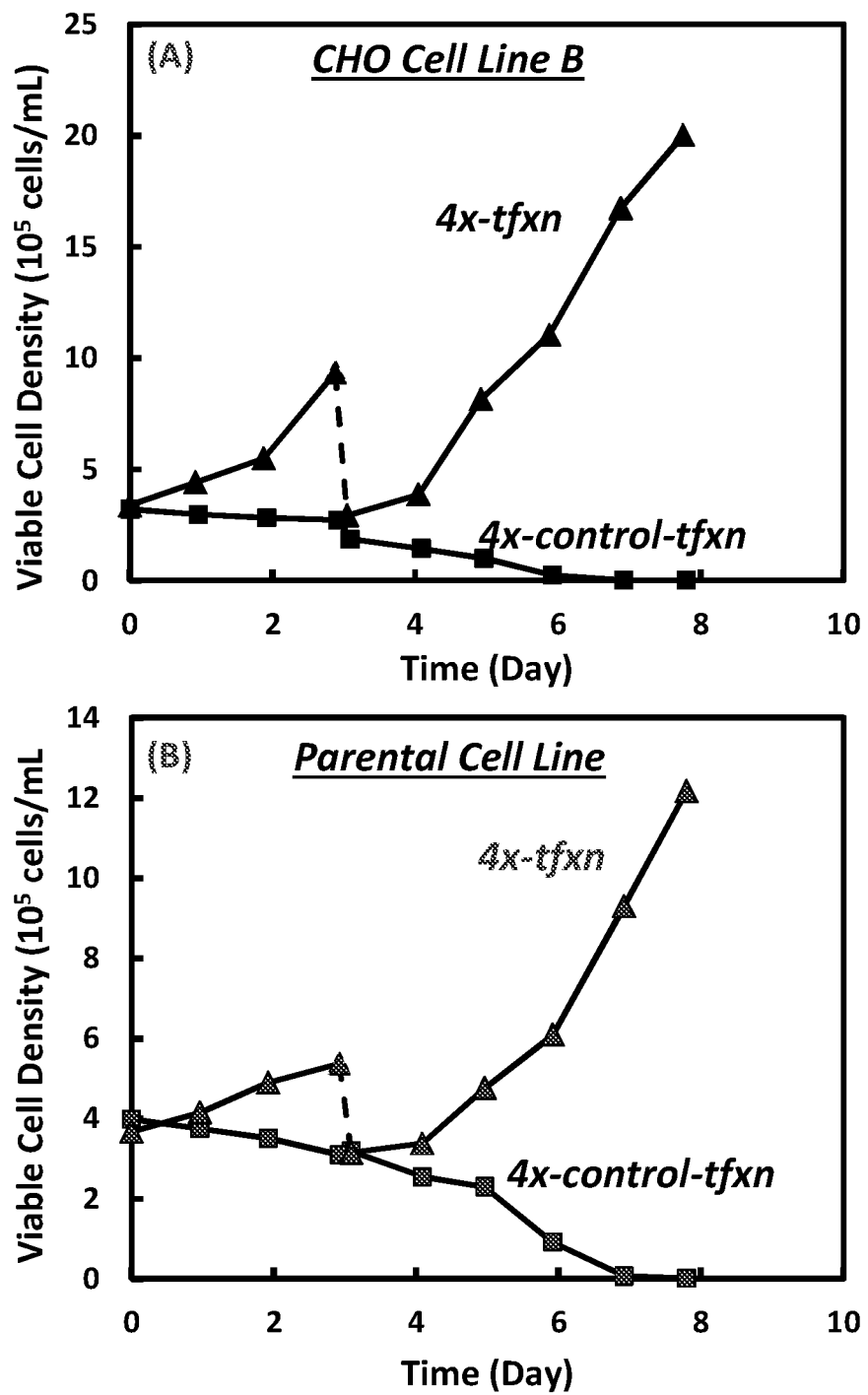
FIG. 29: Growth kinetics of quadruple transfected (4x-tfxn) or negative quadruple transfection control (4x-control-tfxn) cell pools in two subsequent tyrosine-free cell culture passages. Length of the first passage was three days and the length of the second passage was five days. (A) Cell pools derived from CHO cell line B. (B) Cell pools derived from CHO parental cell line. ▲: 4x-tfxn, ■: 4x-control-tfxn.

Cells were inoculated at 0.3E6 cells/mL in 25 mL working volume in 125 mL shake flasks. Shake flasks were incubated on a shaking platform (125 rpm) at 36.5 C and 5% carbon dioxide environment. Cell growth was monitored for 3 days. On day 3, cells were spun down and the cell pellets were re-inoculated into fresh Medium D at 0.3E6 cells/mL and cell growth was monitored for next 5 days.
Results In the first passage, over the course of the three days, both the cell line B and parental cell line derived 4x-tfxn cell pools grew well in tyrosine-free media conditions whereas the 4x-control-tfxn cell pools didn't show any proliferation (FIG. 29). In the second passage, similar to the first round, 4x-tfxn cell pools grew well whereas the 4x-control-tfxn cell pools didn't show any proliferation. This data suggested that 4x-tfxn cell pools were able to synthesize tyrosine from phenylalanine and hence promote the channeling of amino acid flux away from the phenyllactate, 3-(4-hydroxyphenyl) lactate and 4-hydroxyphenyllactate inhibitor biosynthesis pathway (see Example 19).

Further, it was also observed that 3x-tfxn cell pools derived from both the cell line B and parental cell line (with overexpression of PAH, HPD and HGD) were unable to proliferate in tyrosine-free medium (data not shown). This suggested that expression of PCBD1 was critical for cellular ability to biosynthesize tyrosine. It has been previously reported that activity of PAH enzyme is enhanced at high pH (Parniak et al., 1988). Culturing the 4x-tfxn cell pools in tyrosine-free conditions at higher pH (>7.0) further increased the cellular growth rate and viability (data not shown).

Example 19: Demonstrating (i) Similar or Better Growth/Productivity of 4x-tfnx Cell Pools in Tyrosine-Free Fed-Batch Cultures when Compared 4x-Control-tfxn Cell Pools in Tyrosine Supplemented Cultures and, (ii) Reduced Accumulation of 3-(4-hydroxyphenyl)lactate, a Byproduct of Tyrosine Pathway, in 4x-tfxn Cultures Goal The goal of this experiment was to demonstrate that 4x-tfxn cell pools can grow in tyrosine-free HiPDOG cultures at similar or higher growth rates and reach similar or higher peak cell densities and produce similar or higher titers, when compared to 4x-control-tfxn cell pools in typical (tyrosine-supplemented) HiPDOG cultures. Another goal was to establish that the combination of PAH, HPD, HGD and PCBD1 expression along with cultivation in tyrosine-free media suppresses the production of the metabolite byproduct of tyrosine pathway, 3-(4-hydroxyphenyl)lactate.
Materials and Methods:
Cells and Bioreactor Setup 4x-tfxn cells and 4x-control-tfxn cell pools derived from the CHO cell line B, expressing a recombinant antibody, were used in this example. 4x-tfxn cell pools expressed the four mouse enzymes (PAH, HPD, HGD and PCBD1), whereas the 4x-control-tfxn cell pools are the control cells that expressed only the resistance marker for the selection pressure.

Cell line B derived 4x-tfnx cell pools or the 4x-control-tfnx cell pools were inoculated at 1.2E6 cells/mL in HiPDOG fed-batch cultures using tyrosine-free Medium A or original formulation of Medium A (containing tyrosine), respectively (for information on Medium A, see Example 18). To supplement nutrients during the culture, tyrosine-free Feed Medium B was used for 4x-tfxn cell pool fed-batch culture whereas the original composition of Feed Medium B (containing tyrosine) was used for 4x-control-tfxn fed-batch cultures (for information on Medium B, see below). For both the conditions, the culture volume (1 L) and the process parameters including the temperature (36.5 C), pH (until day 2: 7.15-7.20, from day 2 onwards: 7.10-7.15) and the agitation rate (259 rpm) were identical. HiPDOG strategy was employed throughout the run. Viable cell density, glucose, lactate, ammonia and amino acid concentrations were measured on daily basis until day 12. Supernatant samples from both the conditions were analyzed for the levels of the 3-(4-hydroxylphenyl)lactate using the NMR technology described below. Culture amino acid levels were measured using amino acid analysis method described below.

Medium B has the same composition as Medium 5 (U.S. Pat. No. 7,294,484, table 7), but with higher levels of the amino acids (by a factor of 2.5). The concentrations of amino acids in Medium B are shown in Table 9.

TABLE 9

Concentration of Amino Acids in Medium B

| Amino Acids | Concnetration in Medium B (mM) |
|---|---|
| alanine | 6.0 |
| arginine | 32.9 |
| asparagine•H2O | 54.0 |
| aspartic acid | 15.0 |
| cysteine•HCl•H2O | 0.0 |
| cystine•2HCl | 4.7 |
| glutamic acid | 6.0 |
| monosodium glutamate | 0.0 |
| glutamine | 0.0 |
| glycine | 6.0 |
| histidine•HCl•H2O | 10.5 |
| isoleucine | 27.0 |
| leucine | 38.9 |
| lysine•HCl | 30.0 |
| methionine | 12.0 |
| phenylalanine | 15.0 |
| proline | 18.0 |
| serine | 45.2 |
| threonine | 24.0 |
| tryptophan | 4.8 |
| tyrosine•2Na•2H2O | 12.0 |
| valine | 24.0 |

NMR Sample Preparation, Data Acquisition and Processing

1000 μL of each sample was filtered using Nanosep 3K Omega microcentrifuge filter tubes for 60 minutes, and 630 μL of the filtered sample was used for NMR analysis. These filters are preserved with glycerol, and as such some trace amounts of glycerol may appear in the analysis. Internal standard solution was added to each sample solution, and the resulting mixture was vortexed for 30 s. 700 μL of the centrifuged solution was transferred to an NMR tube for data acquisition.

NMR spectra were acquired on a Varian four-channel VNMRS 700 MHz NMR spectrometer equipped with a cryogenically cooled 1H/13C triple resonance biomolecular probe with auto tuning. The pulse sequence used was a 1D-tnnoesy with a 990 ms presaturation on water and a 4 s acquisition time. Spectra were collected with 32 transients and 4 steady-state scans at 298 K.

Spectra were processed and .cnx files were generated using the Processor module in Chenomx NMR Suite 8.0. Compounds were identified and quantified using the Profiler module in Chenomx NMR Suite 8.0 with the Chenomx Compound Library version 9, containing 332 compounds. For reporting purposes, the profiled concentrations have been corrected to reflect the composition of the original sample, instead of the contents of the NMR tube. During sample preparation, each sample is diluted by introducing an internal standard and, where necessary, to increase the analyzed volume of a small sample.

Amino Acid Analysis

10 μL of either a standard amino acid mix solution or a spent media sample (10 times diluted sample) was mixed with 70 μL of AccQ•Tag Ultra borate buffer (Waters UPLC AAA H-Class Applications Kit [176002983]), and 20 μL of AccQ•Tag reagent previously dissolved in 1.0 mL of AccQ•Tag Ultra reagent diluent was added. The reaction was allowed to proceed for 10 min at 55° C. Liquid chromatographic analysis was performed on a Waters Acquity UPLC system, equipped with a binary solvent manager, an autosampler, a column heater and a PDA detector. The separation column was a Waters AccQ•Tag Ultra column (2.1 mm i.d.×100 mm, 1.7 μm particles). The column heater was set at 55° C., and the mobile phase flow rate was maintained at 0.7 mL/min. Eluent A was 10% AccQ•Tag Ultra concentrate solvent A, and eluent B was 100% AccQ•Tag Ultra solvent B. The nonlinear separation gradient was 0-0.54 min (99.9% A), 5.74 min (90.0% A), 7.74 min (78.8% A), 8.04-8.64 min (40.4% A), 8.73-10 min (99.9% A). One microliter of sample was injected for analysis. The PDA detector was set at 260 nm. The previously determined elution times for the amino acids are used to identify the specific amino acid peaks on the chromatogram for each sample. The amino acid concentrations were estimated using the area under the peak and the calibration curve generated using the standard solution (Amino Acids Standard H, Thermo Scientific, PI-20088).

Results

Figures 30A, 30B:
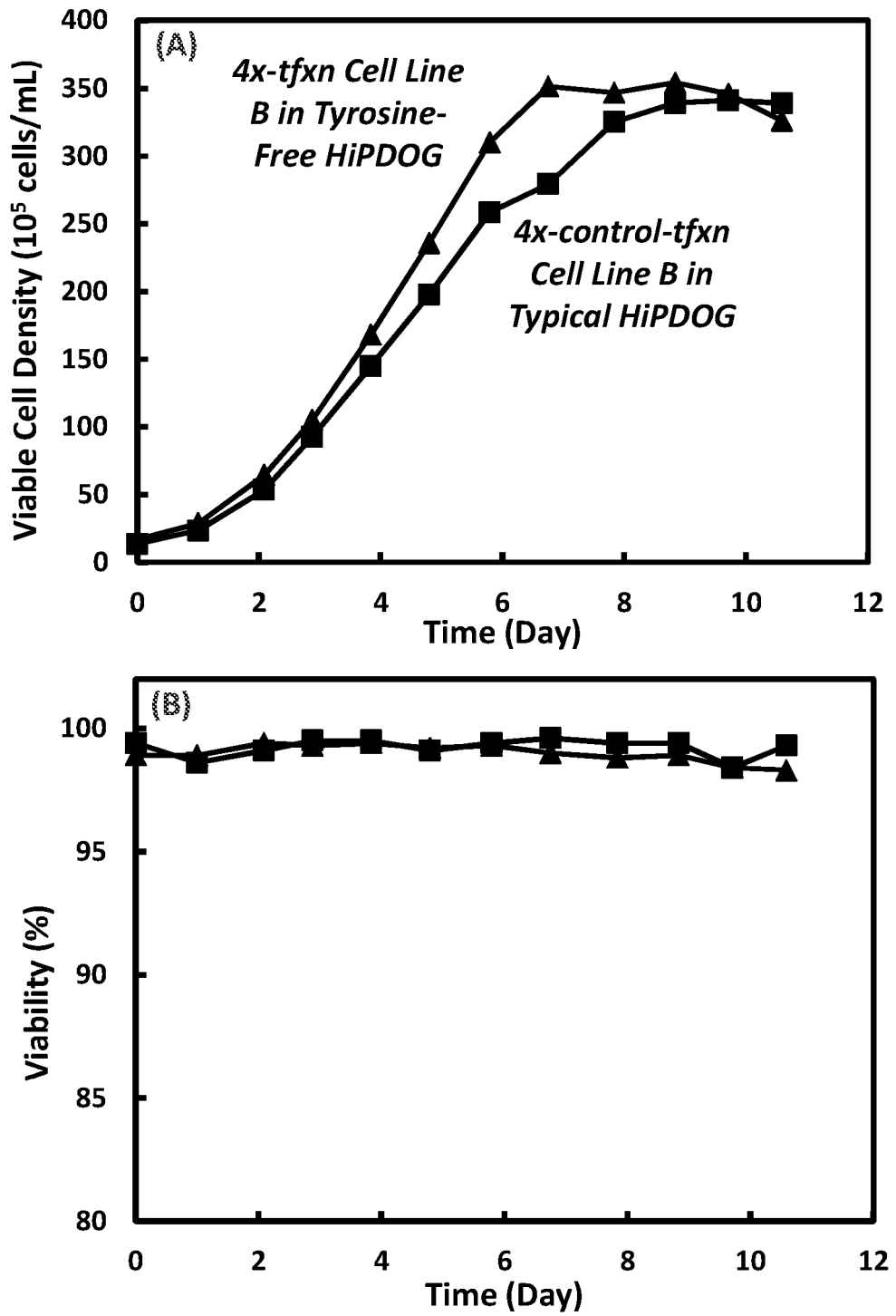
FIG. 30: Comparison of the performance of cell line B derived quadruple transfected (4x-tfxn) cell pools in tyrosine-free HiPDOG fed-batch process as compared to the negative quadruple transfection control (4x-control-tfxn) cell pools in original HiPDOG fed-batch process (tyrosine supplemented). (A) Viable cell density (B) Viability (C) Titer (D) Levels of 3-(4-hydroxyphenyl)lactate ]: 4x-tfxn, ■: 4x-control-tfxn.
Figures 30C, 30D:
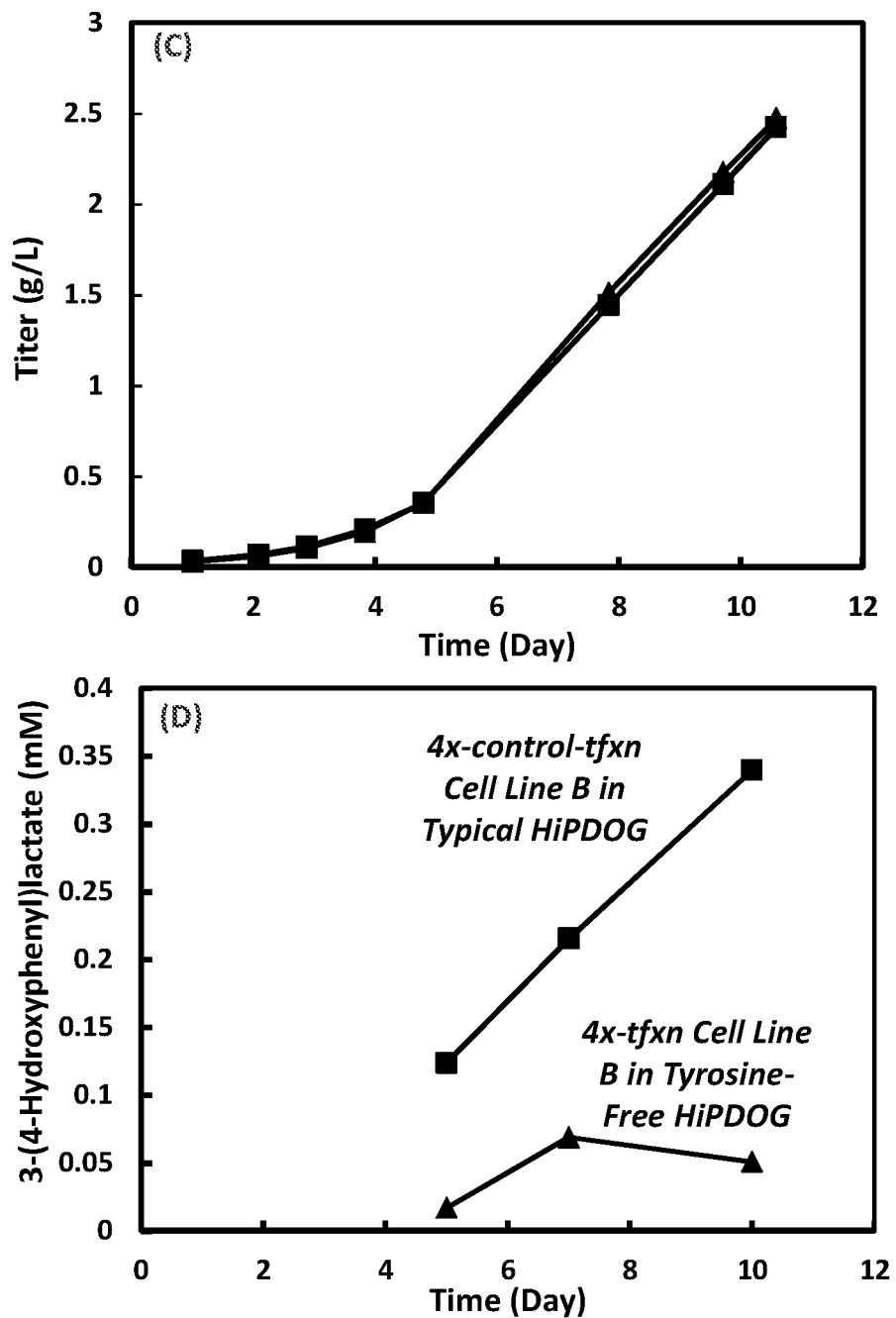

Cell pools in both the cultures grew in an exponential fashion with slightly better growth observed in the 4x-tfxn cell tyrosine-free fed-batch culture as compared to 4x-control-tfxn culture (FIG. 30A). Both cultures attained peak cell densities of 35E6 cells/mL between days 7 and 9 of the cultures. In both the cultures, the cell viabilities were more than 97% through day 12 of the culture (FIG. 30B). Titer profile for both the cultures were very similar with day 11 titer at 2.5 g/L (FIG. 30C). Further, it was observed that 4x-tfxn cells consumed phenylalanine at a faster rate than the 4x-control-tfxn cells (data not shown). Tyrosine accumulation was observed in 4x-tfxn cultures (data not shown). This suggested that 4x-tfxn cells converted phenylalanine to tyrosine to supply the same for their physiological needs (biomass and protein synthesis). Excess tyrosine was secreted into the culture. 4x-control-tfxn culture was supplemented with exogenous tyrosine in inoculation and feed media. The levels of tyrosine decreased over the course of the 4x-control-tfxn culture indicating consumption of tyrosine by these cells (data not shown). In addition, the levels of a byproduct of tyrosine metabolism, 3-(4-hydroxyphenyl) lactate, were significantly lower in 4x-tfxn culture as compared to 4x-control-tfxn culture indicating lower channeling of phenylalanine and/or tyrosine towards byproduct synthesis (FIG. 30D).

Example 20: Probing the Effect of 2-methylbutyrate and Isobutyrate on Growth of CHO Cells Goal:

2-methylbutyrate and isobutyrate are byproducts of isoleucine and valine pathways, which were observed to accumulate in the HiPDOG fed-batch cultures of CHO cell line A. The level of accumulation on day 7 were about 9 mM for 2-methylbutyrate and 2 mM for isobutyrate (data not shown; accumulation for CHO cell line C are in the same order (see Example 21)). This experiment was setup to probe the effect of these two compounds individually on growth of CHO cell line A in the concentration range observed in the HiPDOG fed-batch cultures.

Figures 31A, 31B:
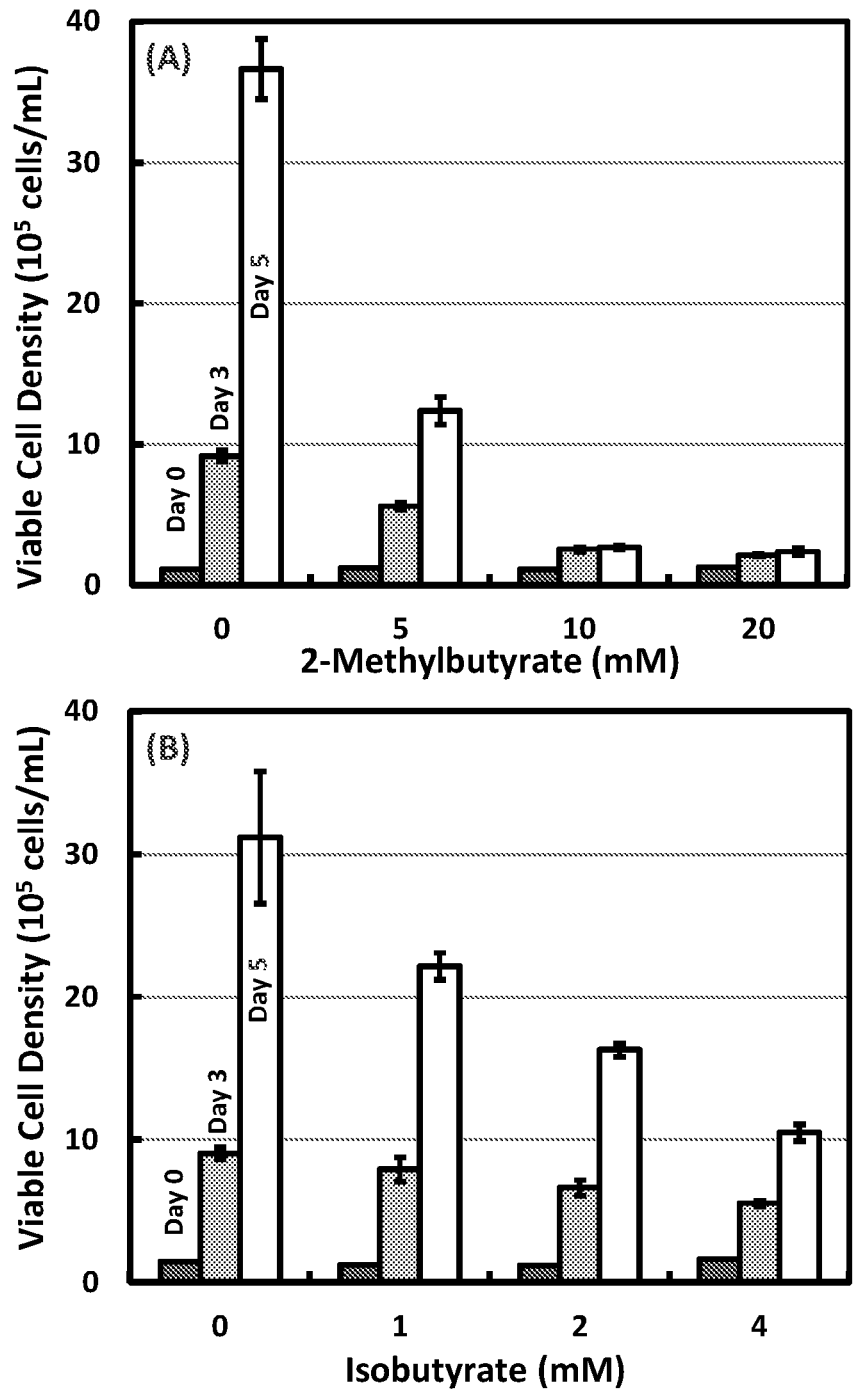
FIG. 31: Effect of different concentrations of 2-methylbutyrate (A) or isobutyrate (B) on growth of CHO cell line A

Materials and Methods:

CHO cell line A producing a recombinant antibody were inoculated at low cell densities (0.1E6 cells/mL) in various conditions in triplicates in 6-well plate cultures. The working volume for each well on day 0 was 4 mL. The conditions tested include fresh Medium A or fresh Medium A supplemented individually with 2-methylbutyrate or isobutyrate at various concentrations. The concentrations tested for 2-methylbutyrate are [0, 5, 10 and 20 mM] and for isobutyrate are [0, 1, 2 and 4 mM]. The 6-well plates were incubated on a shaking platform in 36.5 C and 5% carbon dioxide. Cell growth in all the conditions was monitored for 5 days.
Results:

FIG. 31 shows the independent effect of the 2-methylbutyrate or isobutyrate on growth of the CHO cell line A. Cells cultured in fresh medium grew very well. Cell growth was suppressed when cells were cultured in fresh media supplemented with 2-methylbutyrate (FIG. 31A) or isobutyrate (FIG. 31B) at concentrations higher than 5 mM or 1 mM, respectively. This demonstrates that 2-methylbutyrate and isobutyrate inhibit cell growth. 2-methylbutyrate is a metabolic byproduct of isoleucine metabolism and isobutyrate is a metabolic byproduct of valine metabolism.

Example 21: Demonstrating the Reduction in the Accumulation of 2-methylbutyrate or Isobutyrate Through Limitation of Isoleucine or Valine, Respectively, in Fed-Batch Cultures of CHO Cells (CHO Cell Line C)

Goal

The main goal of this example was to demonstrate reduction in the accumulation of the 2-methylbutyrate or isobutyrate in fed-batch cultures of CHO cells by limiting the supply of the isoleucine or valine, respectively.
Materials and Methods
Cells and Bioreactor Setup The GS-CHO cell line (cell line C) expressing a recombinant antibody was used in this example. Two conditions were tested as part of the this example: A) fed-batch culture with low levels of isoleucine and valine (Low AA), B) fed-batch cultures with normal amino acids concentrations (Control). The experiment was carried out for 12 days.

Figures 32A, 32B, 32C, 32D:
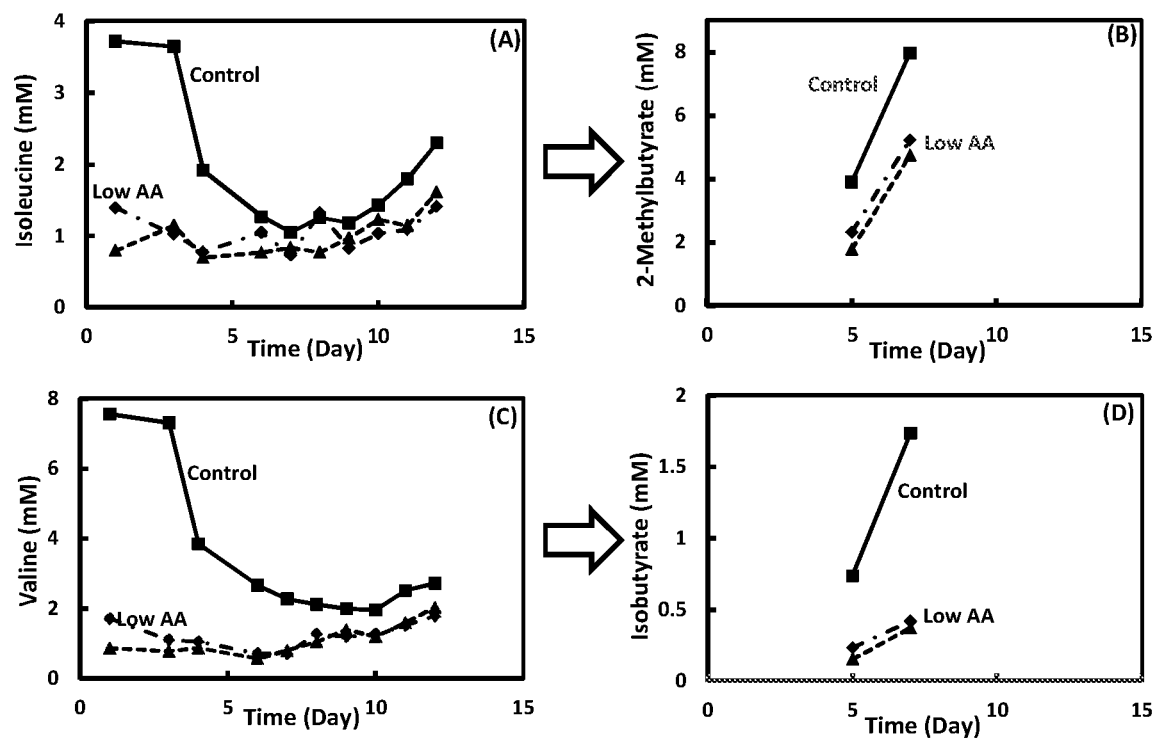
FIG. 32: Suppressing the accumulation of 2-methylbutyrate (B) and isobutyrate (D) by controlling the concentration of isoleucine (A) and valine (C) at low levels in the fed-batch cultures of CHO cell line C. ▲: Low AA, ♦: Low AA, ■: Control
Figure 34A:
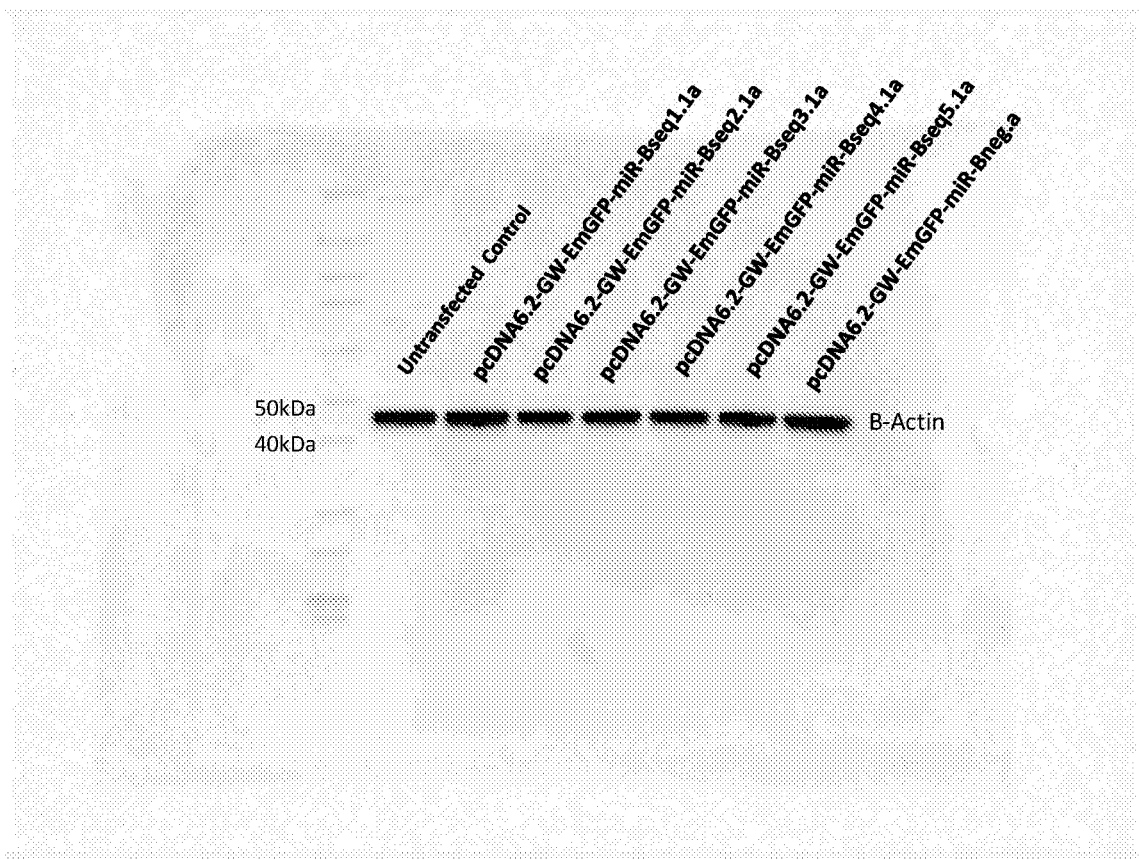
FIG. 34: Western blot for probing the levels of BCAT1 and B-Actin in CHO cells transiently transfected independently with five miRNAs against BCAT1. (A) B-Actin protein levels in untransfected or transfected CHO parental cell line (B) BCAT1 protein levels in untransfected or transfected CHO parental cell line (C) B-Actin protein levels in untransfected or transfected CHO cell line B (D) BCAT1 protein levels in untransfected or transfected CHO cell line B. Gel loading details for all the gels are as follows. Lane 1: protein ladder, lane 2: untrasfected cells, lane 3: cells transfected with BCAT1 miRNA seq1.1a, lane 4: cells transfected with BCAT1 miRNA seq2.1a, lane 5: cells transfected with BCAT1 miRNA seq3.1a, lane 6: cells transfected with miRNA BCAT1 seq4.1a, lane 7: cells transfected with BCAT1 miRNA seq5.1a, lane 8: cells transfected with negative control miRNA. Protein size: 42 kD for B-Actin and 43 kD for BCAT1
Figure 34B:
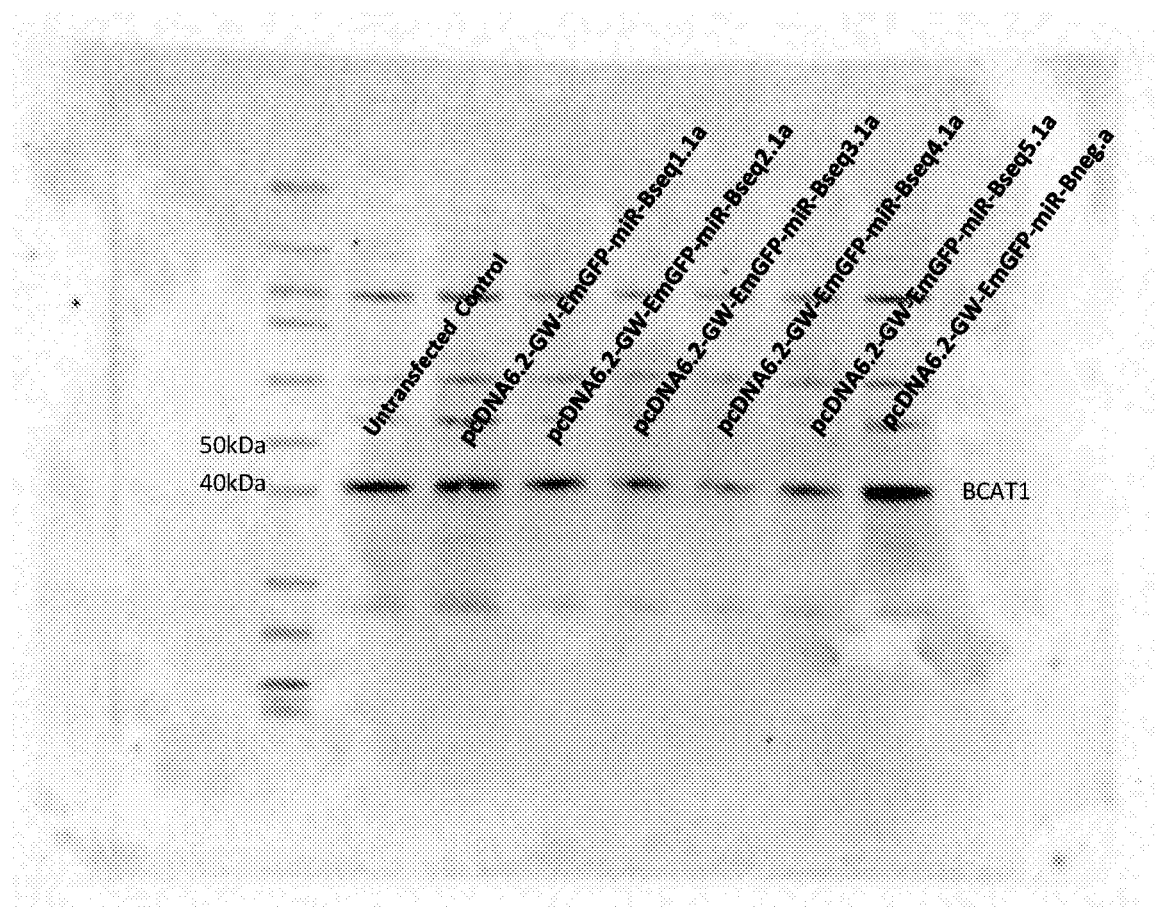
Figure 34C:
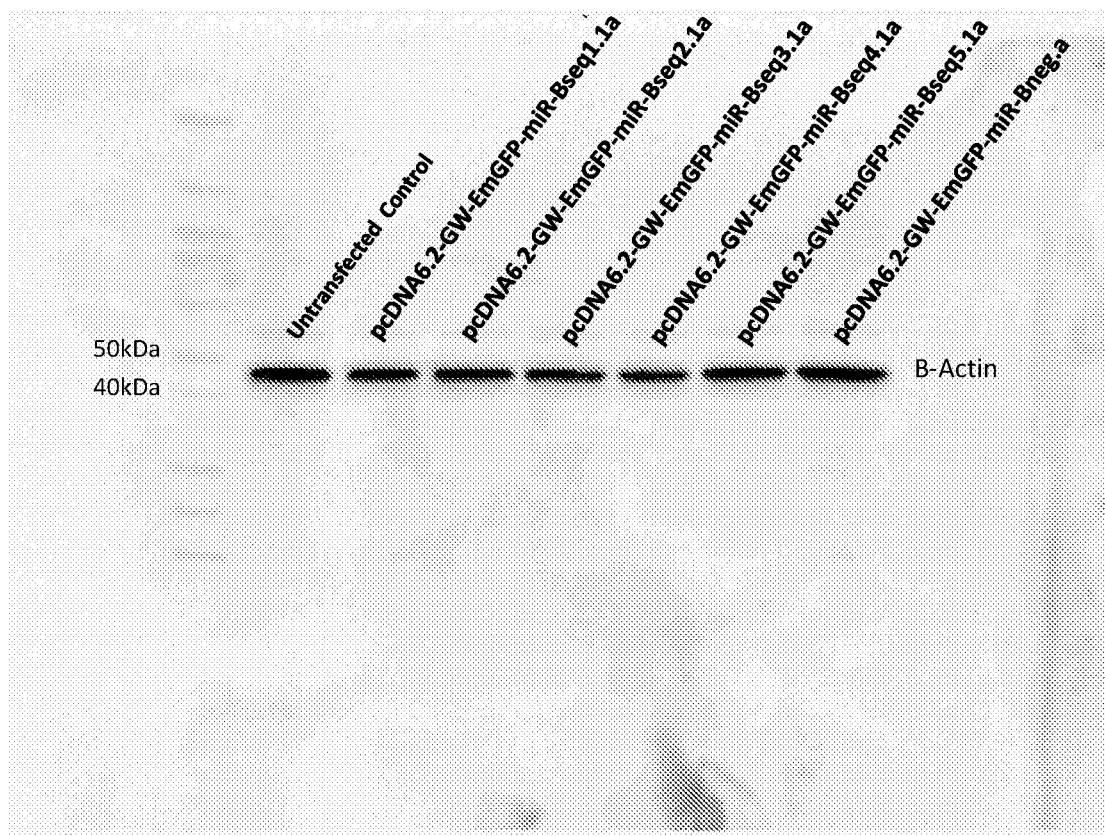
Figure 34D:
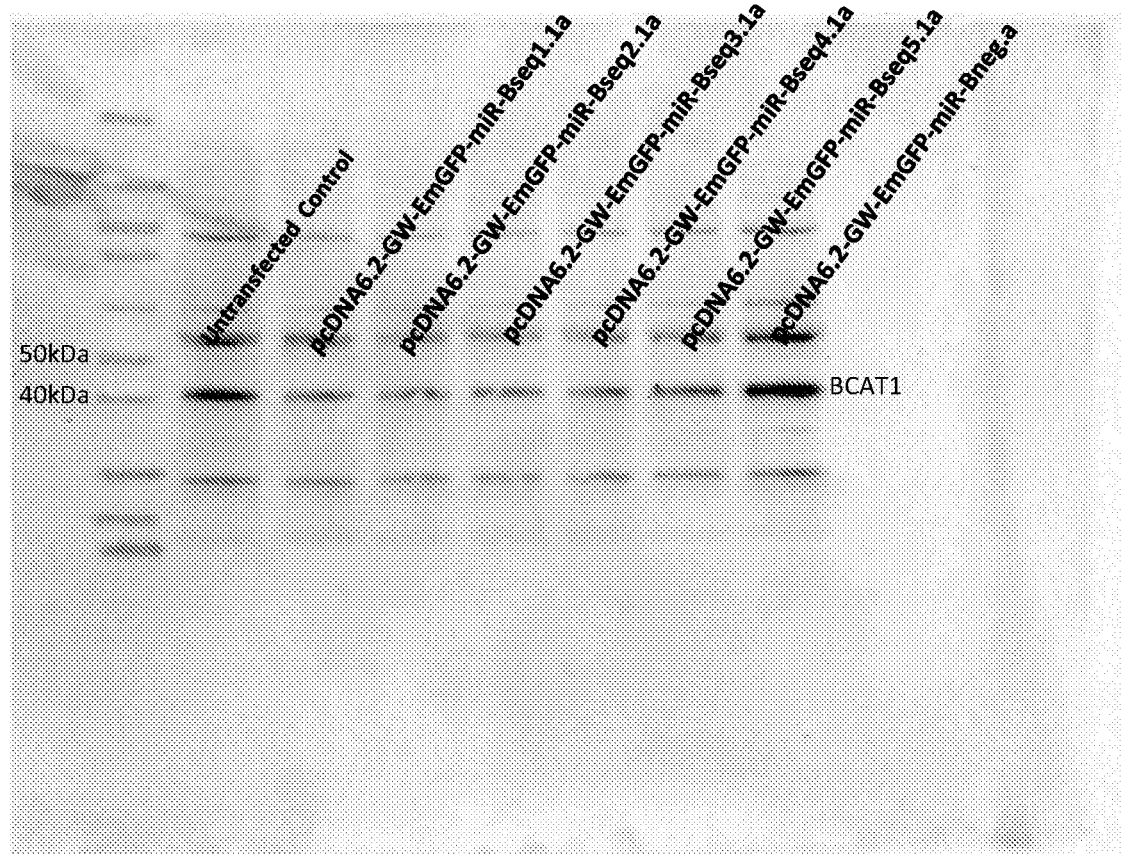

Exponentially growing cells from seed cultures were inoculated at about 4E6 cells/mL into production bioreactors that employed a typical fed-batch process (with typical levels of amino acids) or the low amino acid fed-batch process. In the low amino acid conditions, the concentrations of isoleucine and valine were maintained between 0.5 mM and 1 mM for first seven days of the culture after which they were allowed to increase beyond 1 mM. Viable cell density, glucose, lactate, ammonia and amino acid concentrations were measured on daily basis until day 12. For both the conditions, the culture volume (1 L) and the process parameters including the temperature (36.5 C), pH (6.9-7.2) and the agitation rate (259 rpm) were identical. The base media used in control condition was Medium A and that used in low amino acid conditions was the modified version of Medium A with low concentrations of amino acids, including tyrosine, phenylalanine, methionine, tryptophan, serine, glycine, threonine, leucine, isoleucine and valine. The feed medium used for both the conditions was Medium B. Amino acid levels in Medium B were adjusted such that the amount of amino acid delivered through feeding Medium B, in a semi-continuous fashion, is approximately equal to the amount of amino acid taken up by the culture. The feed rate used was proportional to integral viable cells in the culture. Supernatant samples from both the conditions were analyzed for the levels of the 2-methylbutyrate and isobutyrate using the NMR technology described in example 19. Culture amino acid levels were measured using amino acid analysis method described in example 19.
Results The concentrations of the amino acids, isoleucine and valine, were successfully maintained between 0.5 mM-1 mM in the Low AA condition (FIGS. 32A and 32C). Such limitation of amino acid levels in the Low AA condition resulted in lower accumulation of 2-methylbutyrate (FIG. 32B) and isobutyrate (FIG. 32D).

Example 22: Experiment to Determine the Gene Targets for Metabolic Engineering for Suppressing the Biosynthesis of the Inhibitors (Isovalerate, 2-methylbutyrate and Isobutyrate) Produced from the Branched Chain Amino Acid Pathway Goal This experiment was performed to determine the cause for the biosynthesis of isovalerate, 2-methylbutyrate and isobutyrate, which are byproducts of branched chain amino acid metabolism that accumulated to very high levels in fed-batch cultures of CHO cells. Gene expression of all the enzymes in the branched chain amino acid pathway (BCAA) was probed. Based on the gene expression analysis in BCAA catabolism pathway, gene targets for metabolic engineering of the CHO cells (CHO cell line B and parental cell line) suppressing the biosynthesis of isovalerate, isobutyrate and 2-methylbutyrate were identified.
Results RT qPCR analysis was performed on leucine catabolic pathway genes. The log expression values for the genes in the leucine pathway are shown in FIG. 33A. The gene expression data from the leucine pathway indicate that all enzymes in the pathway were expressed at similar levels. Gene expression for enzymes in isoleucine and valine pathway was also observed to be relatively high in the parental cell line (data not shown). The data did not point towards a clear target in the BCAA pathway that can explain the high rates of isovalerate, isobutyrate and 2-methylbutyrate biosynthesis and secretion. However, the enzymes downstream of the isovalerate, isobutyrate or 2-methylbutyrate nodes might harbor a loss of function mutations, which can explain the channeling of flux towards isovalerate, isobutyrate or 2-methylbutyrate. Since BCAT1 (or BCAT2) and BCK-DHA/BCKDHB enzymes catalyzes the first two steps in all the three branched chain amino acid pathways, knocking-down or knocking-out or inhibiting the activity of any aforementioned enzymes was undertaken with the objective of reducing the biosynthesis of isovalerate, isobutyrate and 2-methylbutyrate (FIG. 33B).

Example 23: Generation of Transient BCAT1 Knockdown CHO Cell Pools to Suppress the Production of BCAA Pathway Inhibitor (Isovalerate, 2-methylbutyrate and Isobutyrate) Biosynthesis Goal This experiment was setup to knockdown BCAT1 gene expression in CHO cell line B and CHO parental cell line in order to limit the production of isovalerate, isobutyrate and 2-methylbutyrate in respective cell cultures.
Materials and Methods miRNA knockdown works by expressing small RNA sequences (approximately 20-25 bases) that are complimentary to a target gene sequence (e.g. BCAT1). The miRNA binds to the messenger RNA (mRNA) of the target gene forming a region of double stranded RNA. This double stranded RNA is targeted for cleavage and degradation by the cell resulting in a net decrease in mRNA to be translated, and hence, protein to be produced. Micro RNA knockdown of BCAT1 was performed using the BLOCK-iT Inducible Pol II miR RNAi Expression Vector Kit with EmGFP (Invitrogen). Five miRNA oligonucleotide pairs (complementary top and bottom strand of BCAT1) were designed using an online tool called Block-iT RNAi Designer and the DNA oligonucleotides were prepared by Integrated DNA technologies. The oligonucleotide pairs were annealed and ligated into the pcDNA™6.2-GW/EmGFP-miR vector. The vectors (five of them) were sequence confirmed by Wyzer-Biosciences (Cambridge, Mass.). The five miRNA vectors or a negative control vector named pcDNA™6.2-GW/EmGFP-miR-neg (provided by Invitrogen with the kit) were transfected into CHO parental cell line or CHO cell line B using the GenePulser XCell eletroporator (BioRad) and were left to recover for two days. After two days, cells were either subjected to selection pressure by antibiotic (blasticidin, 10 ug/mL) for generation of stable cell pools (see Example 24), or cell lysates from the transfected cells (or untransfected cells) were prepared in M-PER protein extraction reagent (Thermo Fisher) supplemented with cOmplete, Mini, EDTA-free Protease Inhibitor Cocktail (Roche). The samples were analyzed by western blot using the Novex NuPage system (Thermo Fisher). The system provides polyacrylamide gels, sample loading buffer, sample reductant, gel running buffer, protein mass standard, nitrocellulose membrane, and chemiluminescence detection reagent. The blots were probed with a rabbit polyclonal anti-BCAT1 antibody (AbCam, Cat # ab110761) or a B-Actin antibody (AbCam, Cat # ab8227). The western blots were imaged using a BioRad ChemiDoc system and analyzed for levels of B-actin and BCAT1.

BCAT1 miRNA Sequences Used:

BCAT1 miRNA Sequences Used:

```
miRNA seq1.1a: TGGGAGAAGCCTCACATTAAA     (SEQ ID NO: 1)

miRNA seq2.1a: TCTGCTGTGAGGACCACTTTG     (SEQ ID NO: 2)

miRNA seq3.1a: AGTGGGCACGATGAATCTGTT     (SEQ ID NO: 3)

miRNA seq4.1a: CACGATGAATCTGTTCCTCTA     (SEQ ID NO: 4)

miRNA seq5.1a: CTTGGGCAAACTGACTGATAT     (SEQ ID NO: 5)
```

Results

FIG. 34 shows western blot for BCAT1 and B-Actin protein levels in transiently transfected cells. B-Actin was included as a house keeping gene (or protein) and was used as an internal comparator of protein expression. Levels of B-Actin were similar across all the five miRNA (transient) transfections, negative miRNA control transfection and untransfected cells (for both CHO cell line B and parental cell line). This indicated even protein loading across all the conditions (FIGS. 34A and 34C). In CHO parental cell line transient transfections, lower level of BCAT1 protein were observed in case of knock-down using miRNA Seq 2.1a, miRNA Seq 3.1a, miRNA Seq 4.1a and miRNA Seq 5.1a. In parental cell line transient transfections, lower level of BCAT1 protein were observed in all the five knock-down conditions tested. Untransfected control and the negative control showed more intense banding pattern indicating higher levels of the BCAT1 proteins.

Example 24: Generation of Stable BCAT1 Knockdown CHO Cell Pools to Suppress the Production of BCAA Pathway Inhibitor (Isovalerate, 2-methylbutyrate and Isobutyrate) Biosynthesis Goal The main goal of this experiment was to develop stable CHO cells pools with reduced levels of BCAT1. The objective was to further demonstrate that these stable pools had reduced capability to produce the BCAA pathway inhibitor metabolites (isovalerate, 2-methylbutyrate and isobutyrate), the reduction of which resulted in better growth and productivity.

Results

Figure 35A:
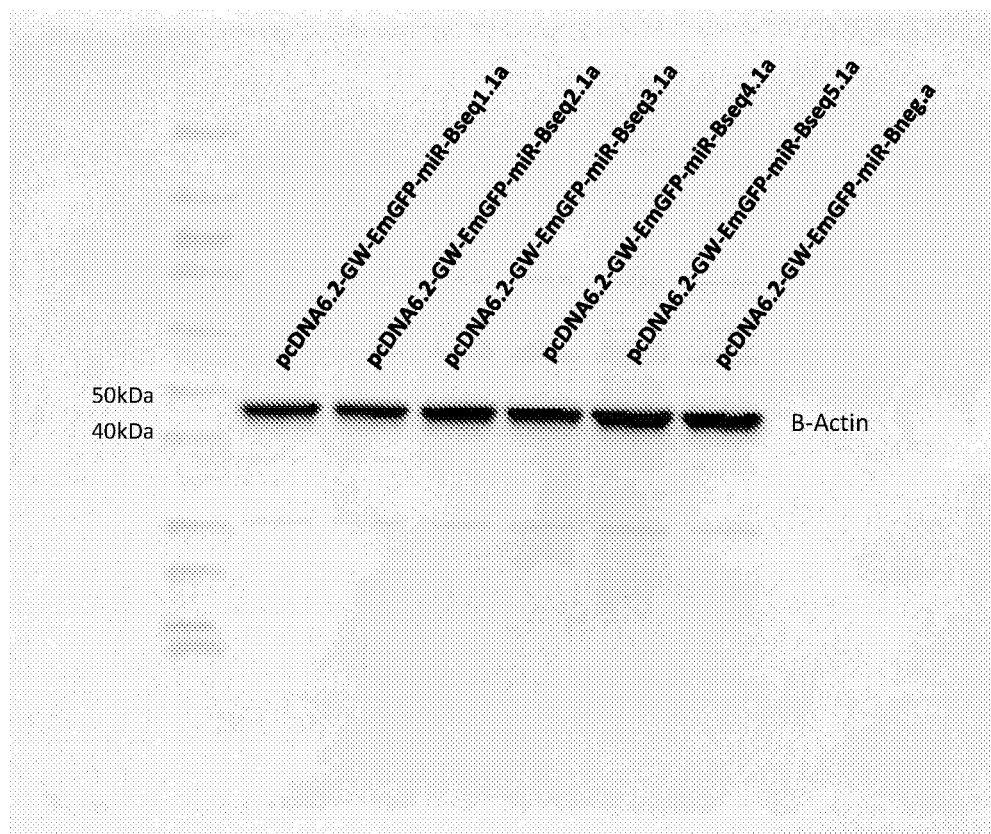
FIG. 35: Western blot for probing the levels of BCAT1 and B-Actin in stable CHO cell pool generated from independent transfections with five miRNAs against BCAT1. (A) B-Actin protein levels in stable pools generated from transfections into CHO parental cell line (B) BCAT1 protein levels in stable pools generated from transfections into CHO parental cell line. Gel loading details for all the gels are as follows. Lane 1: protein ladder, lane 2: cells transfected with BCAT1 miRNA seq1.1a, lane 3: cells transfected with BCAT1 miRNA seq2.1a, lane 4: cells transfected with BCAT1 miRNA seq3.1a, lane 5: cells transfected with miRNA BCAT1 seq4.1a, lane 6: cells transfected with BCAT1 miRNA seq5.1a, lane 7: cells transfected with negative control miRNA. Protein size: 42 kD for B-Actin and 43 kD for BCAT1
Figure 35B:
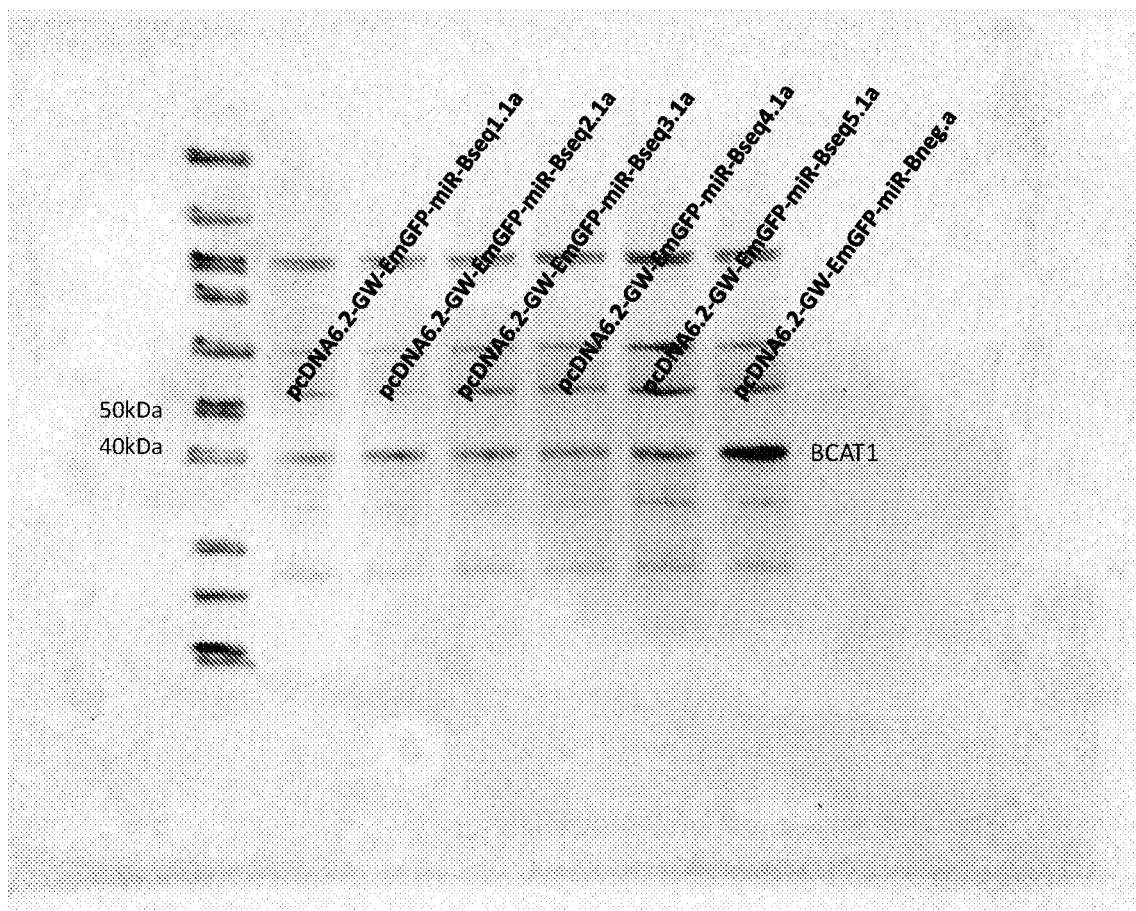

The parental and the CHO cell line B cells transfected with the five BCAT1 miRNA knock-down vectors were selected for stable cell pools. Stable pools were then probed for protein levels of BCAT1. All stable pools of parental cell line, generated from transfections with the five miRNAs, had reduced protein levels of BCAT1, to varying extent, when compared to the stable pools generated from transfection with the negative miRNA sequence control (FIGS. 35A and 35B). This indicated successful generation of stable cell pools with knockdown of BCAT1. Pools with lower protein levels of BCAT1 were selected and tested for production of inhibitors including isovalerate, 2-methylbutyrate and isobutyrate in fed-batch cultures (with and without employing HiPDOG strategy). Cultures producing lower levels of these inhibitory metabolites grew to higher cell densities and yielded higher titers. Equivalent knockdown of iso-enzyme BCAT2 was also performed to demonstrate reduced levels of BCAT2 production for testing for reduced production of inhibitors including isovalerate, 2-methylbutyrate and isobutyrate. BCAT2 is an isoenzyme form of BCAT1, which is catalytically and functionally equivalent to BCAT1 and performs the same function in the leucine, isoleucine and valine pathways depicted in FIG. 33B.

TABLE 10

| Abbreviation | Description |
| --- | --- |
| B-Actin | Actin, beta |
| MIF | Macrophage migration inhibitory factor |
| GOT1 | Glutamic-oxaloacetic transaminase 1, soluble |
| GOT2 | Glutamatic-oxaloacetic transaminase 2, mitochondrial |
| TAT | Tyrosine aminotransferase |
| FAH | Fumarylacetoacetate hydrolase |
| GSTZ1 | Glutathione transferase zeta 1 (maleylacetoacetate isomerase) |
| PAH | Phenylalanine hydroxylase |
| HPD | 4-Hydroxyphenylpyruvic acid dioxygenase |
| HGD | Homogentisate 1,2-dioxygenase |
| DLD | Dihydrolipoamide dehydrogenase |
| IVD | isovaleryl coenzyme A dehydrogenase |
| MCCC1 | Methylcrotonoyl-Coenzyme A carboxylase 1 (alpha) |
| MCCC2 | Methylcrotonoyl-Coenzyme A carboxylase 2 (beta) |
| BCKDHA | Branched chain ketoacid dehydrogenase E1, alpha polypeptide |
| BCKDHB | Branched chain ketoacid dehydrogenase E1, beta polypeptide |
| DBT | Dihydrolipoamide branched chain transacylase E2 |
| BCAT1 | Branched chain aminotransferase 1, cytosolic |
| BCAT2 | Branched chain aminotransferase 2, mitochondrial |
| AUH | AU RNA binding protein/enoyl-coenzyme A hydratase |
| HMGCL | 3-Hydroxy-3-methylglutaryl-Coenzyme A lyase |
| ACADM | Acyl-Coenzyme A dehydrogenase, medium chain |
| GCH1 | GTP cyclohydrolase 1 |
| PTS | 6-Pyruvoyl-tetrahydropterin synthase |

TABLE 10-continued

Abbreviations

| Abbreviation | Description |
| --- | --- |
| SPR | Sepiapterin reductase |
| PCBD1 | Pterin 4 alpha carbinolamine dehydratase/dimerization cofactor of hepatocyte nuclear factor 1 alpha (TCF1) 1 |
| QDPR | Quinoid dihydropteridine reductase |
| $BH_4$ | Tetrahydrobiopterin |
| $BH_4$-4a-carbinolamine | Tetrahydrobiopterin-4 alpha-carbinolamine |
| q-$BH_2$ | Quinoid Dihydrobiopterin |
| $NAD^+$ | Oxidized nicotinamide adenine dinucleotide |
| NADH | Reduced nicotinamide adenine dinucleotide |
| GTP | Guanosine-5'-triphosphate |
| 4x-tfxn | Cell pools transfected with four vectors containing a gene of interest and a resistance marker (PAH & geneticin or, HGD & blasticidin or, HPD & hygromycin or, PCBD1 & puromycin) |
| 4x-control-tfxn | Cell pools transfected with four null vectors containing only a resistance marker (geneticin or, blasticidin or, hygromycin or, puromycin) |
| CoA | Coenzyme A |

REFERENCES

Altamirano C, Illanes A, Becerra S, Cairo J J, Godia F (2006) Considerations on the lactate consumption by CHO cells in the presence of galactose. *Journal of biotechnology* 125: 547-556

Bertoni J M (1981) Competitive inhibition of rat brain hexokinase by 2-deoxyglucose, glucosamine, and metrizamide. *Journal of neurochemistry* 37: 1523-1528

Clem B, Telang S, Clem A, Yalcin A, Meier J, Simmons A, Rasku M A, Arumugam S, Dean W L, Eaton J, Lane A, Trent J O, Chesney J (2008) Small-molecule inhibition of 6-phosphofructo-2-kinase activity suppresses glycolytic flux and tumor growth. *Molecular cancer therapeutics* 7: 110-120

Duvel K, Yecies J L, Menon S, Raman P, Lipovsky A I, Souza A L, Triantafellow E, Ma Q, Gorski R, Cleaver S, Vander Heiden M G, MacKeigan J P, Finan P M, Clish C B, Murphy L O, Manning B D (2010) Activation of a metabolic gene regulatory network downstream of mTOR complex 1. *Molecular cell* 39: 171-183

Gagnon M, Hiller G, Luan Y T, Kittredge A, DeFelice J, Drapeau D (2011) High-end pH-controlled delivery of glucose effectively suppresses lactate accumulation in CHO fed-batch cultures. *Biotechnology and bioengineering* 108: 1328-1337

Kim S H, Lee G M (2007a) Down-regulation of lactate dehydrogenase-A by siRNAs for reduced lactic acid formation of Chinese hamster ovary cells producing thrombopoietin. *Applied microbiology and biotechnology* 74: 152-159

Kim S H, Lee G M (2007b) Functional expression of human pyruvate carboxylase for reduced lactic acid formation of Chinese hamster ovary cells (DG44). *Applied microbiology and biotechnology* 76: 659-665

Lee H L T, Boccazzi P, Gorret N, Ram R J, Sinskey A J (2004) In situ bioprocess monitoring of *Escherichia coli* bioreactions using Raman spectroscopy. *Vibrational Spectroscopy* 35: 131-137

Lee J S, Lee G M (2012) Rapamycin treatment inhibits CHO cell death in a serum-free suspension culture by autophagy induction. *Biotechnology and bioengineering* 109: 3093-3102

Li B, Ryan P W, Ray B H, Leister K J, Sirimuthu N M, Ryder A G (2010) Rapid characterization and quality control of complex cell culture media solutions using raman spectroscopy and chemometrics. *Biotechnology and bioengineering* 107: 290-301

Morgan H P, O'Reilly F J, Wear M A, O'Neill J R, Fothergill-Gilmore L A, Hupp T, Walkinshaw M D (2013) M2 pyruvate kinase provides a mechanism for nutrient sensing and regulation of cell proliferation. *Proceedings of the National Academy of Sciences of the United States of America* 110: 5881-5886

Mulukutla B C, Gramer M, Hu W S (2012) On metabolic shift to lactate consumption in fed-batch culture of mammalian cells. *Metabolic engineering* 14: 138-149

Whelan J, Craven S, Glennon B (2012) In situ Raman spectroscopy for simultaneous monitoring of multiple process parameters in mammalian cell culture bioreactors. *Biotechnology progress* 28: 1355-1362

Whitehouse S, Cooper R H, Randle P J (1974) Mechanism of activation of pyruvate dehydrogenase by dichloroacetate and other halogenated carboxylic acids. *The Biochemical journal* 141: 761-774

Wlaschin K F, Hu W S (2007) Engineering cell metabolism for high-density cell culture via manipulation of sugar transport. *Journal of biotechnology* 131: 168-176

Yi W, Clark P M, Mason D E, Keenan M C, Hill C, Goddard W A, 3rd, Peters E C, Driggers E M, Hsieh-Wilson L C (2012) Phosphofructokinase 1 glycosylation regulates cell growth and metabolism. *Science* 337: 975-980

Zhou M, Crawford Y, Ng D, Tung J, Pynn A F, Meier A, Yuk I H, Vijayasankaran N, Leach K, Joly J, Snedecor B, Shen A (2011) Decreasing lactate level and increasing antibody production in Chinese Hamster Ovary cells (CHO) by reducing the expression of lactate dehydrogenase and pyruvate dehydrogenase kinases. *Journal of biotechnology* 153: 27-34

Zhu G, Zhu X, Fan Q, Wan X (2011) Raman spectra of amino acids and their aqueous solutions. *Spectrochimica acta Part A, Molecular and biomolecular spectroscopy* 78: 1187-1195

Parniak, M. A., Davis, M. D., and Kaufman, S. (1988) Effect of alkaline pH on the activity of rat liver phenylalanine hydroxylase. *The Journal of biological chemistry* 263, 1223-1230.

The invention claimed is:

1. A cell comprising a modified gene which reduces the level of synthesis of growth and/or productivity inhibitors by the cell, wherein the modified gene is Bcat1,
wherein the modification decreases Bcat1 gene expression, and wherein the cell expresses a heterologous recombinant protein.

2. The cell of claim 1, wherein the modification of the Bcat1 gene comprises one or more of deletion, disruption, substitution, point mutation, multiple point mutation, insertion mutation, or frameshift mutation as applied to the Bcat1 gene.

3. The cell of claim 1, wherein Bcat1 gene expression is less than or equal to 50 percent level of Bcat1 expression compared to unmodified cells.

4. The cell of claim 1, wherein Bcat1 gene expression is less than or equal to 10 percent level of Bcat1 expression compared to unmodified cells.

5. The cell of claim 1, wherein the cell is a CHO cell.

6. The cell of claim 1, wherein the cell is a human embryonic kidney cell.

7. The cell of claim 1, wherein the recombinant protein is an antibody.

8. The cell of claim 1, wherein the cell is in a large scale bioreactor of at least 10 liters.

9. A cell comprising a knockdown of Bcat1 that decreases Bcat1 gene expression, wherein the cell is a CHO cell.

10. The cell of claim 9, wherein the cell expresses a heterologous recombinant protein.

11. A cell comprising a knockdown of Bcat1 that decreases Bcat1 gene expression, wherein the cell is a human embryonic kidney cell.

12. The cell of claim 11, wherein the cell expresses a heterologous recombinant protein.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Cricetulus griseus

<400> SEQUENCE: 1

```
tgggagaagc ctcacattaa a                                              21

<210> SEQ ID NO 2
<211> LENGTH: 21
<212> TYPE: DNA
<213> ORGANISM: Cricetulus griseus

<400> SEQUENCE: 2
tctgctgtga ggaccacttt g                                              21

<210> SEQ ID NO 3
<211> LENGTH: 21
<212> TYPE: DNA
<213> ORGANISM: Cricetulus griseus

<400> SEQUENCE: 3
agtgggcacg atgaatctgt t                                              21

<210> SEQ ID NO 4
<211> LENGTH: 21
<212> TYPE: DNA
<213> ORGANISM: Cricetulus griseus

<400> SEQUENCE: 4
cacgatgaat ctgttcctct a                                              21

<210> SEQ ID NO 5
<211> LENGTH: 21
<212> TYPE: DNA
<213> ORGANISM: Cricetulus griseus

<400> SEQUENCE: 5
cttgggcaaa ctgactgata t                                              21
```